(12) United States Patent
Chavez et al.

(10) Patent No.: US 11,629,342 B2
(45) Date of Patent: Apr. 18, 2023

(54) CAS9-BASED TRANSCRIPTION MODULATION SYSTEMS

(71) Applicant: President and Fellows of Harvard College, Cambridge, MA (US)

(72) Inventors: Alejandro Chavez, New York, NY (US); Nan Cher Yeo, Johor Bahru (MY)

(73) Assignee: President and Fellows of Harvard College, Cambridge, MA (US)

( * ) Notice: Subject to any disclaimer, the term of this patent is extended or adjusted under 35 U.S.C. 154(b) by 317 days.

(21) Appl. No.: 16/756,995

(22) PCT Filed: Oct. 17, 2018

(86) PCT No.: PCT/US2018/056301
§ 371 (c)(1),
(2) Date: Apr. 17, 2020

(87) PCT Pub. No.: WO2019/079462
PCT Pub. Date: Apr. 25, 2019

(65) Prior Publication Data
US 2021/0123034 A1    Apr. 29, 2021

Related U.S. Application Data

(60) Provisional application No. 62/573,320, filed on Oct. 17, 2017.

(51) Int. Cl.
| | |
|---|---|
| *C12N 9/22* | (2006.01) |
| *C12N 15/11* | (2006.01) |
| *C12N 15/86* | (2006.01) |
| *C07K 14/47* | (2006.01) |
| *C12N 15/85* | (2006.01) |
| *A61K 38/00* | (2006.01) |

(52) U.S. Cl.
CPC .............. *C12N 9/22* (2013.01); *C12N 15/11* (2013.01); *C12N 15/86* (2013.01); *C07K 14/4703* (2013.01); *C07K 2319/00* (2013.01); *C07K 2319/70* (2013.01); *C07K 2319/80* (2013.01); *C12N 15/8509* (2013.01); *C12N 2310/20* (2017.05); *C12N 2740/15043* (2013.01)

(58) Field of Classification Search
None
See application file for complete search history.

(56) References Cited

U.S. PATENT DOCUMENTS

| 8,551,708 B2 | 10/2013 | Bernitz et al. |
|---|---|---|
| 2002/0115080 A1 | 8/2002 | Skouv et al. |
| 2004/0204345 A1 | 10/2004 | Case et al. |
| 2009/0233856 A1 | 9/2009 | Laccone |
| 2014/0273230 A1 | 9/2014 | Chen et al. |
| 2015/0191744 A1* | 7/2015 | Wolfe .................... C12N 15/63 435/456 |
| 2016/0024555 A1 | 1/2016 | Church et al. |
| 2016/0304952 A1 | 10/2016 | Boyden et al. |

FOREIGN PATENT DOCUMENTS

| WO | 2016063264 A1 | 4/2016 |
|---|---|---|
| WO | WO2016205613 | * 12/2016 |

OTHER PUBLICATIONS

Chen et al. "Nanoscale Imaging of RNA with Expansion Microscopy," Nature Methods, Jul. 4, 2016 (Jul. 4, 2016), vol. 13, No. 8, pp. 679-684. entire document.
International Search Report and Written Opinion issued based on PCT/US2018/036415, dated Oct. 16, 2018.
Yao, Nan Cher et al., An Enhanced CRISPR Repressor for Targeted Mammalian Gene Regulation, Nature Methods. Jul. 16, 2018, vol. 15, pp. 611-616; entire document; doi: 10.1038/s41592-018-0048-5.
International Search Report & Written Opinion issued for PCT/US2018/056301 dated Dec. 21, 2018.

* cited by examiner

*Primary Examiner* — Suzanne M Noakes
*Assistant Examiner* — Jae W Lee
(74) *Attorney, Agent, or Firm* — Banner & Witcoff, Ltd.

(57) ABSTRACT

The present disclosure provides methods and compositions of modulating expression of a target nucleic acid in a eukaryotic cell. The methods include providing to the cell a guide RNA complementary to the target nucleic acid sequence, providing to the cell a fusion protein, wherein the fusion protein comprises a nuclease null Cas9 protein and a transcriptional effector domain, wherein the nuclease null Cas9 protein interacts with the guide RNA and binds to the target nucleic acid sequence in a site specific manner and wherein the transcriptional effector domain modulates expression of the target nucleic acid.

9 Claims, 26 Drawing Sheets
Specification includes a Sequence Listing.

FIG. 12D d

|        | dCas9 | dCas9-KRAB | dCas9-KRAB-MeCP2 |
|--------|-------|------------|------------------|
| Up     | 13    | 35         | 17               |
| No FC  | 13645 | 13623      | 13641            |
| Down   | 0     | 0          | 0                |

CAS9-BASED TRANSCRIPTION MODULATION SYSTEMS

RELATED APPLICATION DATA

This application is a National Stage Application under 35 U.S.C. 371 of co-pending PCT application PCT/US2018/056301 designating the United States and filed Oct. 17, 2018; which claims the benefit of U.S. provisional application No. 62/573,320 filed on Oct. 17, 2017 each of which are hereby incorporated by reference in their entireties.

STATEMENT OF GOVERNMENT INTERESTS

This invention was made with government support under CA009216 and HG008525 and HG005550 awarded by National Institutes of Health (NIH). The government has certain rights in the invention.

SEQUENCE LISTING

The instant application contains a Sequence Listing which has been submitted electronically in ASCII format and is hereby incorporated by reference in its entirety. Said ASCII copy, created on Nov. 13, 2018, is named 010498_01139_WO_SL.txt and is 26,413 bytes in size.

BACKGROUND

Methods of modulating expression of a target gene in a cell are known. RNA interference (RNAi) is a useful method for targeted gene knockdown and has been widely used for large-scale library screens. RNAi, however, has several limitations—in particular, RNAi-based knockdown suffers from broad off-target effects along with incomplete knockdown (Jackson A L, Bartz S R, Schelter J, Kobayashi S V, Burchard J, Mao M, Li B, Cavet G, Linsley P S, "Expression profiling reveals off-target gene regulation by RNAi," Nat Biotechnol. 2003 June; 21(6):635-7, Epub 2003 May 18; Sigoillot F D, Lyman S, Huckins J F, Adamson B, Chung E, Quattrochi B, King R W, "A bioinformatics method identifies prominent off-targeted transcripts in RNAi screens," Nat Methods. 2012 February 19; 9(4):363-6; Krueger U, Bergauer T, Kaufmann B, Wolter I, Pilk S, Heider-Fabian M, Kirch S, Artz-Oppitz C, Isselhorst M, Konrad J, "Insights into effective RNAi gained from large-scale siRNA validation screening," Oligonucleotides, 1 Jan. 2007, 17(2):237-250). Custom DNA binding proteins such as zinc finger proteins or transcription activator-like effectors (TALEs) fused to transcriptional repressor domains, while able to mediate selective gene suppression, suffer from issues of scale due to the fact that each desired target gene necessitates the generation of a new protein (Gaj T, Gersbach C A, Barbas C F 3rd., "ZFN, TALEN, and CRISPR/Cas-based methods for genome engineering," Trends Biotechnol. 2013 July; 31(7):397-405, Epub 2013 May 9; Joung J K, Sander J D, "TALENs: a widely applicable technology for targeted genome editing," Nat Rev Mol Cell Biol. 2013 January; 14(1):49-55, Epub 2012 Nov. 21; Margolin J F[1], Friedman J R, Meyer W K, Vissing H, Thiesen H J, Rauscher F J 3rd., "Krüppel-associated boxes are potent transcriptional repression domains," Proc Natl Acad Sci USA. 1994 May 10; 91(10):4509-13).

The CRISPR/Cas9 system, which mediates adaptive immunity within bacteria and archaea, has emerged as a powerful tool for genome engineering (Cho S W, Kim S, Kim J M, Kim J S, "Targeted genome engineering in human cells with the Cas9 RNA-guided endonuclease," Nat Biotechnol. 2013 March; 31(3):230-2, Epub 2013 Jan. 29; Cong L, Ran F A, Cox D, Lin S, Barretto R, Habib N, Hsu P D, Wu X, Jiang W, Marraffini L A, Zhang F, "Multiplex genome engineering using CRISPR/Cas systems," Science. 2013 Feb. 15; 339(6121):819-23, Epub 2013 Jan. 3; Mali P, Yang L, Esvelt K M, Aach J, Guell M, DiCarlo J E, Norville J E, Church G M, "RNA-guided human genome engineering via Cas9," Science. 2013 Feb. 15; 339(6121):823-6, Epub 2013 Jan. 3; Jinek M, Chylinski K, Fonfara I, Hauer M, Doudna J A, Charpentier E, "A programmable dual-RNA-guided DNA endonuclease in adaptive bacterial immunity," Science. 2012 Aug. 17; 337(6096):816-21, Epub 2012 Jun. 28; DiCarlo J E, Norville J E, Mali P, Rios X, Aach J, Church G M, "Genome engineering in Saccharomyces cerevisiae using CRISPR-Cas systems," Nucleic Acids Res. 2013 April; 41(7):4336-43, Epub 2013 Mar. 4; Hwang W Y, Fu Y, Reyon D, Maeder M L, Tsai S Q, Sander J D, Peterson R T, Yeh J R, Joung J K, "Efficient genome editing in zebrafish using a CRISPR-Cas system," Nat Biotechnol. 2013 March; 31(3):227-9, Epub 2013 Jan. 29; Wang H, Yang H, Shivalila C S, Dawlaty M M, Cheng A W, Zhang F, Jaenisch R, "One-step generation of mice carrying mutations in multiple genes by CRISPR/Cas-mediated genome engineering," Cell. 2013 May 9; 153(4):910-8, Epub 2013 May 2). Cas9 is an RNA-guided endonuclease that can be directed to specific DNA sequences through complementarity between the Cas9-associated single guide RNA (sgRNA) and the target locus, provided that a protospacer-adjacent motif (PAM) is proximal to the target. Because changing the target gene Cas9 cuts only requires that a user alter the delivered sgRNA, Cas9 has been quickly adopted for target gene ablation and for performing unbiased genome-wide screens (Zhou Y, Zhu S, Cai C, Yuan P, Li C, Huang Y, Wei W, "High-throughput screening of a CRISPR/Cas9 library for functional genomics in human cells," Nature. 2014 May 22; 509(7501):487-91, Epub 2014 Apr. 9; Shalem O, Sanjana N E, Hartenian E, Shi X, Scott D A, Mikkelson T, Heckl D, Ebert B L, Root D E, Doench J G, Zhang F, "Genome-scale CRISPR-Cas9 knockout screening in human cells," Science. 2014 Jan. 3; 343(6166):84-87, Epub 2013 Dec. 12; Wang T, Wei J J, Sabatini D M, Lander E S, "Genetic screens in human cells using the CRISPR-Cas9 system," Science. 2014 Jan. 3; 343(6166):80-4, Epub 2013 Dec. 12; Koike-Yusa H, Li Y, Tan E P, Velasco-Herrera Mdel C, Yusa K, "Genome-wide recessive genetic screening in mammalian cells with a lentiviral CRISPR-guide RNA library," Nat Biotechnol. 2014 March; 32(3):267-73, Epub 2013 Dec. 23). However, using Cas9 to cut a gene in order to disable it can lead to cellular toxicity due to the formation of double-stranded DNA breaks (Mandegar M A, Huebsch N, Frolov E B, Shin E, Truong A, Olvera M P, Chan A H, Miyaoka Y, Holmes K, Spencer C I, Judge L M, Gordon D E, Eskildsen T V, Villalta J E, Horlbeck M A, Gilbert L A, Krogan N J, Sheikh S P, Weissman J S, Qi L S, So P L, Conklin B R, "CRISPR Interference Efficiently Induces Specific and Reversible Gene Silencing in Human iPSCs," Cell Stem Cell. 2016 Apr. 7; 18(4):541-53, Epub 2016 Mar. 10), a lack a reversibility for the Cas9-generated indels, and difficulties in perturbing noncoding RNAs (Goyal A, Myacheva K, Groß M, Klingenberg M, Duran Arqué B, Diederichs S, "Challenges of CRISPR/Cas9 applications for long non-coding RNA genes," Nucleic Acids Res. 2017 Feb. 17; 45(3):e12).

Within Cas9, the amino acids critical for DNA catalysis can be mutated to generate a nuclease null Cas9 (dCas9) variant that remains competent for DNA binding but lacks endonuclease activity (Qi L S, Larson M H, Gilbert L A, Doudna J A, Weissman J S, Arkin A P, Lim W A, "Repurposing CRISPR as an RNA-guided platform for sequence-specific control of gene expression," Cell. 2013 Feb. 28; 152(5):1173-83). Previous work has shown that by fusing several transcriptional activators to dCas9 in tandem, a synergistic increase in regulation can be achieved (Chavez A, Scheiman J, Vora S, Pruitt B W, Tuttle M, P R Iyer E, Lin S, Kiani S, Guzman C D, Wiegand D J, Ter-Ovanesyan D, Braff J L, Davidsohn N, Housden B E, Perrimon N, Weiss R, Aach J, Collins J J, Church G M, "Highly efficient Cas9-mediated transcriptional programming," Nat Methods. 2015 April; 12(4):326-8, Epub 2015 Mar. 2; Konermann S, Brigham M D, Trevino A E, Joung J, Abudayyeh O O, Barcena C, Hsu P D, Habib N, Gootenberg J S, Nishimasu H, Nureki O, Zhang F, "Genome-scale transcriptional activation by an engineered CRISPR-Cas9 complex," Nature. 2015 Jan. 29; 517(7536):583-8, Epub 2014 Dec. 10; Zalatan J G, Lee M E, Almeida R, Gilbert L A, Whitehead E H, La Russa M, Tsai J C, Weissman J S, Dueber J E, Qi L S, Lim W A, "Engineering complex synthetic transcriptional programs with CRISPR RNA scaffolds," Cell. 2015 Jan. 15; 160(1-2):339-50, Epub 2014 Dec. 18; Tanenbaum M E, Gilbert L A, Qi L S, Weissman J S, Vale R D, "A protein-tagging system for signal amplification in gene expression and fluorescence imaging," Cell. 2014 Oct. 23; 159(3):635-46, Epub 2014 Oct. 9). When directed towards the transcriptional start site of a gene, dCas9 can physically block RNA polymerase passage, thereby leading to gene silencing (Qi L S, Larson M H, Gilbert L A, Doudna J A, Weissman J S, Arkin A P, Lim W A, "Repurposing CRISPR as an RNA-guided platform for sequence-specific control of gene expression," Cell. 2013 Feb. 28; 152(5):1173-83). Further improvement in transcriptional inhibition has been achieved by addition of the Krüppel-associated box (KRAB) repression domain to dCas9 for dCas9-based repression studies (Gilbert L A, Larson M H, Morsut L, Liu Z, Brar G A, Torres S E, Stern-Ginossar N, Brandman O, Whitehead E H, Doudna J A, Lim W A, Weissman J S, Qi L S, "CRISPR-mediated modular RNA-guided regulation of transcription in eukaryotes," Cell. 2013 Jul. 18; 154(2):442-51, Epub 2013 Jul. 11; Gilbert L A, Horlbeck M A, Adamson B, Villalta J E, Chen Y, Whitehead E H, Guimaraes C, Panning B, Ploegh H L, Bassik M C, Qi L S, Kampmann M, Weissman J S, "Genome-Scale CRISPR-Mediated Control of Gene Repression and Activation," Cell. 2014 Oct. 23; 159(3):647-61, Epub 2014 Oct. 9; Thakore P I, Black J B, Hilton I B, Gersbach C A, "Editing the epigenome: technologies for programmable transcription and epigenetic modulation," Nat Methods. 2016 February; 13(2):127-37). There is a continuing need in the art for a more robust dCas9-based repressor for effective regulation of target gene expression in a cell.

SUMMARY

Aspects of the present disclosure are directed to compositions and methods of modulating expression of a target nucleic acid in a cell. According to one aspect, the methods include providing to the cell a guide RNA complementary to the target nucleic acid sequence and a fusion protein. According to another aspect, the fusion protein includes a nuclease null Cas9 (dCas9) fused to an effector domain, wherein the effector domain includes transcriptional regulators or epigenetic modifiers, or their respective functional domains. In certain embodiments, the effector domain includes various fusions of multiple transcriptional repressor domains. In certain embodiments, the effector domain includes a fusion of two, three, or more transcriptional repressor domains including Krüppel-associated box (KRAB), MeCP2, SIN3A, HDT1, MBD2B, NIPP1, and HP1A. In one embodiment, the effector domain comprises a bipartite fusion of KRAB-MeCP2. In one embodiment, the fusion protein comprises a fusion of dCas9-KRAB-MeCP2.

According to another aspect, the present disclosure provides nucleic acids encoding the guide RNA and the dCas9 fusion protein. In some embodiments, the nucleic acids encoding the guide RNA and the dCas9 fusion protein are present on a single vector or on separate vectors, such as engineered DNA plasmid vectors or viral vectors. The guide RNA comprises a portion that is complementary to a sequence of a target site and guides the dCas9 fusion protein to the target site, wherein the dCas9 fusion protein modulate the target gene expression. In one embodiments, the transcriptional regulator is a transcriptional repressor. In some embodiments, the transcriptional repressor includes a fusion of multiple repressor domains. In an exemplary embodiment, the vector is a lentiviral expression plasmid vector which can be packaged into a recombinant lentiviral vector according to methods known to those of skill in the art.

In one embodiment, the method of modulating expression of a target nucleic acid in a eukaryotic cell includes providing to the cell a guide RNA complementary to the target nucleic acid sequence, providing to the cell a fusion protein, wherein the fusion protein comprises a nuclease null Cas9 protein (dCas9) and an effector domain, wherein the effector domain comprises a fusion of transcriptional repressor domains including Krüppel-associated box (KRAB), MeCP2, SIN3A, HDT1, MBD2B, NIPP1, and HP1A, and wherein the nuclease null Cas9 protein interacts with the guide RNA and binds to the target nucleic acid sequence in a site specific manner and wherein the effector domain modulates expression of the target nucleic acid.

In another embodiment, the guide RNA and/or the fusion protein is provided to the cell by introducing to the cell a nucleic acid encoding the guide RNA and/or the fusion protein, and the cell expresses the guide RNA and the fusion protein.

In one embodiment, the cell is a eukaryotic cell. In another embodiment, the eukaryotic cell is a yeast cell, a plant cell, a mammalian cell or a human cell.

In one embodiment, the effector domain comprises a fusion of two transcriptional repressor domains including Krüppel-associated box (KRAB), MeCP2, SIN3A, HDT1, MBD2B, NIPP1, and HP1A. In another embodiment, the effector domain comprises a fusion of three transcriptional repressor domains including Krüppel-associated box (KRAB), MeCP2, SIN3A, HDT1, MBD2B, NIPP1, and HP1A. In one embodiment, the effector domain comprises a fusion of multiple transcriptional repressor domains including Krüppel-associated box (KRAB), MeCP2, SIN3A, HDT1, MBD2B, NIPP1, and HP1A. In another embodiment, the effector domain comprises a bipartite fusion of KRAB-MeCP2. In one embodiment, the fusion protein comprises a fusion of dCas9-KRAB-MeCP2. In another embodiment, the dCas9-KRAB-MeCP2 fusion exhibited at least two fold stronger repression of target gene expression compared to nuclease null Cas9 or nuclease null Cas9 fused to KRAB.

Further features and advantages of certain embodiments of the present invention will become more fully apparent in the following description of embodiments and drawings thereof, and from the claims.

BRIEF DESCRIPTION OF THE DRAWINGS

The foregoing and other features and advantages of the present embodiments will be more fully understood from the following detailed description of illustrative embodiments taken in conjunction with the accompanying drawings in which:

FIG. 1A shows schematic of the EYFP fluorescent reporter construct used in the targeted screen. A protospacer sequence followed by TGG PAM (SEQ ID NO: 1) is placed within the minimal CMV (minCMV) promoter upstream of the EYFP reporter gene. The EYFP reporter is driven upon binding of a GAL4-VP16 protein to the UAS sequences present upstream of the minCMV promoter. FIG. 1B shows that the fluorescent reporter and minCMV-targeting sgRNA were co-transfected with the indicated repressors into HEK293T cells. At 2 d post transfection, EYFP fluorescence levels were measured to quantify the amount of repression from the various dCas9 fusion proteins. The name of the protein from which the transcriptional regulatory domain was isolated is listed on the x-axis. All domains were fused to the C-terminus of the dCas9 protein. The six top-performing domains (marked in blue) were used for subsequent engineering. n=two independent transfections. Data are presented as median fluorescence±s.e.m. * indicates $p<0.005$ vs. dCas9.

FIG. 3A shows schematic of dCAS9-KRAB and dCas9-KRAB-MeCP2 repressors. NLS=nuclear localization signal. FIG. 3B shows results of single gene repression. Each sample was transfected with an sgRNA against the indicated gene along with the labeled repressors. Negative (Neg.) control was transfected with the sgRNA alone. All samples were treated with puromycin to select for transfected cells, and RNA levels were examined at 3 d post transfection. FIG. 3C shows RNA expression during three separate multiplex repression studies. In each experiment, guides targeting the indicated genes were transfected simultaneously. Data are shown as mean±s.e.m. (n=2 independent transfections). # indicates $p<0.05$ vs. negative control, * indicates $p<0.05$ vs. dCas9-KRAB.

FIG. 7A shows single gene targets in addition to those shown in FIG. 3B. FIG. 7B shows that a new group of sgRNAs were designed against the same set of target genes shown in FIG. 3C and performed another round of multiplex repression experiments. With this new group of sgRNAs, dCas9-KRAB-MeCP2 still showed improved activity for the majority of targets tested. n=two independent transfections. Data are presented as mean±s.e.m. # indicates $p<0.05$ vs. negative control. * indicates $p<0.05$ vs. dCas9-KRAB.

FIG. 8A shows nine sgRNAs were designed to tile along the CANX promoter and 5' UTR on either the template (T) or non-template (NT) strands. Significant improvements in repression by dCas9-KRAB-MeCP2 as compared to dCas9-KRAB was observed even when the sgRNA was positioned outside of the optimal targeting window (from −50 to 200 bp relative to TSS) identified for the previous technologies. FIG. 8B shows that similarly to FIG. 8A the effect of an array of sgRNAs tiling along the promoter and 5' UTR sequence of SYVN1 was examined. Only a subset of the tested sgRNAs are shown. See FIG. 9 for activity of the full panel of 16 sgRNAs. Combining multiple sgRNAs did not further improve gene repression for either dCas9-KRAB or dCas9-KRAB-MeCP2. FIG. 8C shows RNA expression of the indicated target genes using one or two sgRNAs. Combining two sgRNAs did not improve repression of the examined target gene. Data are shown as mean±s.e.m. (n=2 independent transfections)*$p<0.05$ vs. dCas9-KRAB.

FIG. 10A shows HEK293T cells were transfected with a guide targeting the SYVN1 gene along with the indicated dCas9 repressor. Expression of the target gene SYVN1 and its surrounding genes that are kilobases away were examined. Data are shown as mean±s.e.m. * $p<0.05$ vs. dCas9-KRAB. FIG. 10B shows RNA-seq analysis of HEK293T cells transfected with an sgRNA targeting CXCR4 along with dCas9, dCas9-KRAB or dCas9-KRAB-MeCP2 repressors. Data are normalized and $Log_2$-transformed counts per million (CPM) values plotted for each repressor (y-axis) versus a negative control population of cells transfected with the CXCR4 sgRNA alone (x-axis). Pearson's and Spearman's correlation coefficients are provided for each dCas9-repressor. The data are representative of the average of two independent transfections.

FIG. 11A shows that expression of the target gene CXCR4 and its surrounding genes that are kilobases away were examined. Black and red bars represent cells transfected with dCas9-KRAB and dCas9-KRAB-MeCP2, respectively. Data are shown as mean±s.e.m. * p<0.05 v.s. dCas9-KRAB. FIG. 11B depicts RNA-seq analysis of HEK293T cells transfected with an sgRNA targeting CXCR4 along with dCas9, dCas9-KRAB or dCas9-KRAB-MeCP2 repressors. Shown are density plots indicating the fold changes in gene expression from dCas9, dCas9-KRAB, or dCas9-KRAB-MeCP2. CXCR4 expression is indicated with green, blue, or red dot in each sample and control is indicated with black dot. The data are representative of the average of two independent biological replicates.

FIGS. 12A-12D depict results of differential expression (DE) of RNA-seq experiment. FIGS. 12A-12C show $Log_2$ fold change versus average $log_2$ CPM for dCas9, dCas9-KRAB and dCAS9-KRAB-MeCP2 relative to control sample for two biological replicates. Genes with no fold change are given in black, differentially expressed genes are given in grey, and differentially expressed genes above a threshold of $Log_2(1.5)$ are given in red. Positive $Log_2(FC)$ represents transcriptional activation while negative values indicate repression. FIG. 12D shows a summary of DE gene numbers for dCas9, dCas9-KRAB and dCAS9-KRAB-MeCP2 systems.

FIG. 13A shows a heatmap representing distances between each gene pair is calculated based on Euclidean distance and $(1-R)^2/2$ represents the Pearson's correlation of those two genes. Normalized $Log_2(CPM)$ values represent large negative (colored in blue) and positive (colored in red) correlations, where genes with large positive correlations correspond to small Euclidean distances and cluster together. FIGS. 13B-13C show venn diagrams comparing gene offsets among all repressors for (B) downregulated and (C) upregulated genes.

FIG. 14A shows HAP1 cells stably expressing dCas9 repressors were generated. Shown is the expression level of dCas9 repressors in the different stable cell lines. # indicates p<0.05 vs. dCas9-expressing cell line. FIG. 14B shows stable cells were transduced with lentiviruses containing an sgRNA targeting the indicated genes. dCas9-KRAB-MeCP2-containing cell line induced stronger suppression of most target genes. n=two independent transfections. Data are presented as mean±s.e.m. * indicates p<0.05 vs. dCas9-KRAB.

DETAILED DESCRIPTION

Figure 1A:
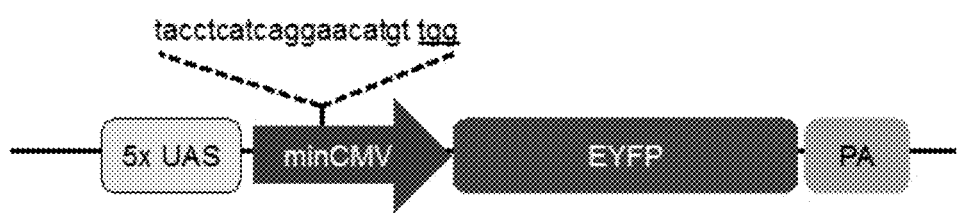
FIGS. 1A-1B depict targeted screen that identifies repression domains that function with dCas9.

Aspects of the present disclosure are directed to methods of modulating expression of a target nucleic acid in a cell. The methods include providing to the cell a guide RNA complementary to the target nucleic acid sequence and a fusion protein. The fusion protein includes a nuclease null Cas9 (dCas9) and an effector domain. According to one aspect, the effector domain includes transcriptional regulators or epigenetic modifiers. According to another aspect, the present disclosure provides nucleic acids encoding the guide RNA and the dCas9 fusion protein. In some embodiments, the nucleic acids encoding the guide RNA and the dCas9 fusion protein are present on a single vector or on separate vectors, such as engineered DNA plasmid vectors or viral vectors. The vector is then used to deliver the nucleic acids encoding the guide RNA and the dCas9 fusion protein into the desired cells or tissues. Once delivered into the cell, the dCas9 fusion protein and the guide RNA are expressed. The guide RNA comprises portion that is complementary to a sequence of a target site and guides the dCas9 fusion protein to the target site. In this manner, expression of the target nucleic acid sequence is modulated depending on the specific transcriptional regulator or epigenetic modifier fused with the dCas9. In one embodiments, the transcriptional regulator is a transcriptional repressor. In some embodiments, the transcriptional repressor includes a fusion of multiple repressor domains. In an exemplary embodiment, the vector is a lentiviral expression plasmid vector which can be packaged into a recombinant lentiviral vector according to methods known to those of skill in the art.

Cas9 Description

Embodiments of the present disclosure are directed to CRISPR/Cas based transcriptional regulators. RNA guided DNA binding proteins are readily known to those of skill in the art to bind to DNA for various purposes. Such DNA binding proteins may be naturally occurring. DNA binding proteins having nuclease activity are known to those of skill in the art, and include naturally occurring DNA binding proteins having nuclease activity, such as Cas9 proteins present, for example, in Type II CRISPR systems. Such Cas9 proteins and Type II CRISPR systems are well documented in the art. See Makarova et al., *Nature Reviews, Microbiology*, Vol. 9, June 2011, pp. 467-477 including all supplementary information hereby incorporated by reference in its entirety.

In general, bacterial and archaeal CRISPR-Cas systems rely on short guide RNAs in complex with Cas proteins to direct degradation of complementary sequences present within invading foreign nucleic acid. See Deltcheva, E. et al. CRISPR RNA maturation by trans-encoded small RNA and host factor RNase III. *Nature* 471, 602-607 (2011); Gasiunas, G., Barrangou, R., Horvath, P. & Siksnys, V. Cas9-crRNA ribonucleoprotein complex mediates specific DNA cleavage for adaptive immunity in bacteria. *Proceedings of the National Academy of Sciences of the United States of America* 109, E2579-2586 (2012); Jinek, M. et al. A programmable dual-RNA-guided DNA endonuclease in adaptive bacterial immunity. *Science* 337, 816-821 (2012); Sapranauskas, R. et al. The *Streptococcus thermophilus* CRISPR/Cas system provides immunity in *Escherichia coli*. *Nucleic acids research* 39, 9275-9282 (2011); and Bhaya, D., Davison, M. & Barrangou, R. CRISPR-Cas systems in bacteria and archaea: versatile small RNAs for adaptive defense and regulation. *Annual review of genetics* 45, 273-297 (2011). A recent in vitro reconstitution of the *S. pyogenes* type II CRISPR system demonstrated that crRNA ("CRISPR RNA") fused to a normally trans-encoded tracrRNA ("trans-activating CRISPR RNA") is sufficient to direct Cas9 protein to sequence-specifically cleave target DNA sequences matching the crRNA. Expressing a gRNA homologous to a target site results in Cas9 recruitment and degradation of the target DNA. See H. Deveau et al., Phage response to CRISPR-encoded resistance in *Streptococcus thermophilus*. *Journal of Bacteriology* 190, 1390 (February, 2008).

Three classes of CRISPR systems are generally known and are referred to as Type I, Type II or Type III). According to one aspect, a particular useful enzyme according to the present disclosure to cleave dsDNA is the single effector enzyme, Cas9, common to Type II. See K. S. Makarova et al., Evolution and classification of the CRISPR-Cas systems. *Nature reviews. Microbiology* 9, 467 (June, 2011) hereby incorporated by reference in its entirety. Within bacteria, the Type II effector system consists of a long pre-crRNA transcribed from the spacer-containing CRISPR locus, the multifunctional Cas9 protein, and a tracrRNA important for gRNA processing. The tracrRNAs hybridize to the repeat regions separating the spacers of the pre-crRNA, initiating dsRNA cleavage by endogenous RNase III, which is followed by a second cleavage event within each spacer by Cas9, producing mature crRNAs that remain associated with the tracrRNA and Cas9. TracrRNA-crRNA fusions are contemplated for use in the present methods.

According to one aspect, the enzyme of the present disclosure, such as Cas9 unwinds the DNA duplex and searches for sequences matching the crRNA to cleave. Target recognition occurs upon detection of complementarity between a "protospacer" sequence in the target DNA and the remaining spacer sequence in the crRNA. Importantly, Cas9 cuts the DNA only if a correct protospacer-adjacent motif (PAM) is also present at the 3' end. According to certain aspects, different protospacer-adjacent motif can be utilized. For example, the *S. pyogenes* system requires an NGG sequence, where N can be any nucleotide. *S. thermophilus* Type II systems require NGGNG (see P. Horvath, R. Barrangou, CRISPR/Cas, the immune system of bacteria and archaea. *Science* 327, 167 (Jan. 8, 2010) hereby incorporated by reference in its entirety and NNAGAAW (see H. Deveau et al., Phage response to CRISPR-encoded resistance in *Streptococcus thermophilus*. *Journal of bacteriology* 190, 1390 (February, 2008) hereby incorporated by reference in its entirety), respectively, while different *S. mutans* systems tolerate NGG or NAAR (see J. R. van der Ploeg, Analysis of CRISPR in *Streptococcus mutans* suggests frequent occurrence of acquired immunity against infection by M102-like bacteriophages. *Microbiology* 155, 1966 (June, 2009) hereby incorporated by reference in its entirety. Bioinformatic analyses have generated extensive databases of CRISPR loci in a variety of bacteria that may serve to identify additional useful PAMs and expand the set of CRISPR-targetable sequences (see M. Rho, Y. W. Wu, H. Tang, T. G. Doak, Y. Ye, Diverse CRISPRs evolving in human microbiomes. *PLoS genetics* 8, e1002441 (2012) and D. T. Pride et al., Analysis of streptococcal CRISPRs from human saliva reveals substantial sequence diversity within and between subjects over time. *Genome research* 21, 126 (January, 2011) each of which are hereby incorporated by reference in their entireties.

In *S. pyogenes*, Cas9 generates a blunt-ended double-stranded break 3 bp upstream of the protospacer-adjacent motif (PAM) via a process mediated by two catalytic domains in the protein: an HNH domain that cleaves the complementary strand of the DNA and a RuvC-like domain that cleaves the non-complementary strand. See Jinek et al., *Science* 337, 816-821 (2012) hereby incorporated by reference in its entirety. Cas9 proteins are known to exist in many Type II CRISPR systems including the following as identified in the supplementary information to Makarova et al., Nature Reviews, Microbiology, Vol. 9, June 2011, pp. 467-

477; *Methanococcus maripaludis* C7; *Corynebacterium diphtheriae*; *Corynebacterium efficiens* YS-314; *Corynebacterium glutamicum* ATCC 13032 Kitasato; *Corynebacterium glutamicum* ATCC 13032 Bielefeld; *Corynebacterium glutamicum* R; *Corynebacterium kroppenstedtii* DSM 44385; *Mycobacterium abscessus* ATCC 19977; *Nocardia farcinica* IFM10152; *Rhodococcus erythropolis* PR4; *Rhodococcus jostii* RHA1; *Rhodococcus opacus* B4 uid36573; *Acidothermus cellulolyticus* 11B; *Arthrobacter chlorophenolicus* A6; *Kribbella flavida* DSM 17836 uid43465; *Thermomonospora curvata* DSM 43183; *Bifidobacterium dentium* Bd1; *Bifidobacterium longum* DJO10A; *Slackia heliotrinireducens* DSM 20476; *Persephonella marina* EX H1; *Bacteroides fragilis* NCTC 9434; *Capnocytophaga ochracea* DSM 7271; *Flavobacterium psychrophilum* JIP02 86; *Akkermansia muciniphila* ATCC BAA 835; *Roseiflexus castenholzii* DSM 13941; *Roseiflexus* RS1; *Synechocystis* PCC6803; *Elusimicrobium minutum* Pei191; uncultured Termite group 1 bacterium phylotype Rs D17; *Fibrobacter succinogenes* S85; *Bacillus cereus* ATCC 10987; *Listeria innocua*; *Lactobacillus casei*; *Lactobacillus rhamnosus* GG; *Lactobacillus salivarius* UCC118; *Streptococcus agalactiae* A909; *Streptococcus agalactiae* NEM316; *Streptococcus agalactiae* 2603; *Streptococcus dysgalactiae equisimilis* GGS 124; *Streptococcus equi zooepidemicus* MGCS10565; *Streptococcus gallolyticus* UCN34 uid46061; *Streptococcus gordonii* Challis subst CH1; *Streptococcus mutans* NN2025 uid46353; *Streptococcus mutans*; *Streptococcus pyogenes* M1 GAS; *Streptococcus pyogenes* MGAS5005; *Streptococcus pyogenes* MGAS2096; *Streptococcus pyogenes* MGAS9429; *Streptococcus pyogenes* MGAS10270; *Streptococcus pyogenes* MGAS6180; *Streptococcus pyogenes* MGAS315; *Streptococcus pyogenes* SSI-1; *Streptococcus pyogenes* MGAS10750; *Streptococcus pyogenes* NZ131; *Streptococcus thermophiles* CNRZ1066; *Streptococcus thermophiles* LMD-9; *Streptococcus thermophiles* LMG 18311; *Clostridium botulinum* A3 Loch Maree; *Clostridium botulinum* B Eklund 17B; *Clostridium botulinum* Ba4 657; *Clostridium botulinum* F Langeland; *Clostridium cellulolyticum* H10; *Finegoldia magna* ATCC 29328; *Eubacterium rectale* ATCC 33656; *Mycoplasma gallisepticum*; *Mycoplasma* mobile 163K; *Mycoplasma penetrans*; *Mycoplasma synoviae* 53; *Streptobacillus moniliformis* DSM 12112; *Bradyrhizobium* BTAi1; *Nitrobacter hamburgensis* X14; *Rhodopseudomonas palustris* BisB18; *Rhodopseudomonas palustris* BisB5; *Parvibaculum lavamentivorans* DS-1; *Dinoroseobacter shibae* DFL 12; *Gluconacetobacter diazotrophicus* Pal 5 FAPERJ; *Gluconacetobacter diazotrophicus* Pal 5 JGI; *Azospirillum* B510 uid46085; *Rhodospirillum rubrum* ATCC 11170; *Diaphorobacter* TPSY uid29975; *Verminephrobacter eiseniae* EF01-2; *Neisseria meningitides* 053442; *Neisseria meningitides* alpha14; *Neisseria meningitides* Z2491; *Desulfovibrio salexigens* DSM 2638; *Campylobacter jejuni* doylei 269 97; *Campylobacter jejuni* 81116; *Campylobacter jejuni*; *Campylobacter lari* RM2100; *Helicobacter hepaticus*; *Wolinella succinogenes*; *Tolumonas auensis* DSM 9187; *Pseudoalteromonas atlantica* T6c; *Shewanella pealeana* ATCC 700345; *Legionella pneumophila* Paris; *Actinobacillus succinogenes* 130Z; *Pasteurella multocida*; *Francisella tularensis novicida* U112; *Francisella tularensis* holarctica; *Francisella tularensis* FSC 198; *Francisella tularensis tularensis*; *Francisella tularensis* WY96-3418; and *Treponema denticola* ATCC 35405. The Cas9 protein may be referred by one of skill in the art in the literature as Csn1. An exemplary *S. pyogenes* Cas9 protein sequence is provided in Deltcheva et al., *Nature* 471, 602-607 (2011) hereby incorporated by reference in its entirety.

Modification to the Cas9 protein is contemplated by the present disclosure. CRISPR systems useful in the present disclosure are described in R. Barrangou, P. Horvath, CRISPR: new horizons in phage resistance and strain identification. *Annual review of food science and technology* 3, 143 (2012) and B. Wiedenheft, S. H. Sternberg, J. A. Doudna, RNA-guided genetic silencing systems in bacteria and archaea. *Nature* 482, 331 (Feb. 16, 2012) each of which are hereby incorporated by reference in their entireties.

According to certain aspects, the DNA binding protein is altered or otherwise modified to inactivate the nuclease activity. Such alteration or modification includes altering one or more amino acids to inactivate the nuclease activity or the nuclease domain. Such modification includes removing the polypeptide sequence or polypeptide sequences exhibiting nuclease activity, i.e. the nuclease domain, such that the polypeptide sequence or polypeptide sequences exhibiting nuclease activity, i.e. nuclease domain, are absent from the DNA binding protein. Other modifications to inactivate nuclease activity will be readily apparent to one of skill in the art based on the present disclosure. Accordingly, a nuclease-null DNA binding protein includes polypeptide sequences modified to inactivate nuclease activity or removal of a polypeptide sequence or sequences to inactivate nuclease activity. The nuclease-null DNA binding protein retains the ability to bind to DNA even though the nuclease activity has been inactivated. Accordingly, the DNA binding protein includes the polypeptide sequence or sequences required for DNA binding but may lack the one or more or all of the nuclease sequences exhibiting nuclease activity. Accordingly, the DNA binding protein includes the polypeptide sequence or sequences required for DNA binding but may have one or more or all of the nuclease sequences exhibiting nuclease activity inactivated.

According to one aspect, a DNA binding protein having two or more nuclease domains may be modified or altered to inactivate all but one of the nuclease domains. Such a modified or altered DNA binding protein is referred to as a DNA binding protein nickase, to the extent that the DNA binding protein cuts or nicks only one strand of double stranded DNA. When guided by RNA to DNA, the DNA binding protein nickase is referred to as an RNA guided DNA binding protein nickase. An exemplary DNA binding protein is an RNA guided DNA binding protein nuclease of a Type II CRISPR System, such as a Cas9 protein or modified Cas9 or homolog of Cas9. An exemplary DNA binding protein is a Cas9 protein nickase. An exemplary DNA binding protein is an RNA guided DNA binding protein of a Type II CRISPR System which lacks nuclease activity. An exemplary DNA binding protein is a nuclease-null or nuclease deficient Cas9 protein.

According to an additional aspect, nuclease-null Cas9 proteins are provided where one or more amino acids in Cas9 are altered or otherwise removed to provide nuclease-null Cas9 proteins. According to one aspect, the amino acids include D10 and H840. See Jinek et al., *Science* 337, 816-821 (2012). According to an additional aspect, the amino acids include D839 and N863. According to one aspect, one or more or all of D10, H840, D839 and H863 are substituted with an amino acid which reduces, substantially eliminates or eliminates nuclease activity. According to one aspect, one or more or all of D10, H840, D839 and H863 are substituted with alanine. According to one aspect, a Cas9 protein having one or more or all of D10, H840, D839 and H863 substituted with an amino acid which reduces, substantially eliminates or eliminates nuclease activity, such as alanine, is referred to as a nuclease-null Cas9 ("Cas9Nuc")

and exhibits reduced or eliminated nuclease activity, or nuclease activity is absent or substantially absent within levels of detection. According to this aspect, nuclease activity for a Cas9Nuc may be undetectable using known assays, i.e. below the level of detection of known assays.

According to one aspect, the Cas9 protein, Cas9 protein nickase or nuclease null Cas9 includes homologs and orthologs thereof which retain the ability of the protein to bind to the DNA and be guided by the RNA. According to one aspect, the Cas9 protein includes the sequence as set forth for naturally occurring Cas9 from S. thermophiles, S. aureus or S. pyogenes and protein sequences having at least 20%, 30%, 40%, 50%, 60%, 70%, 80%, 90%, 95%, 98% or 99% homology thereto and being a DNA binding protein, such as an RNA guided DNA binding protein.

An exemplary CRISPR system includes the S. thermophiles or S. aureus Cas9 nuclease (ST1 Cas9, Sa Cas9) (see Esvelt K M, et al., Orthogonal Cas9 proteins for RNA-guided gene regulation and editing, Nature Methods., (2013) hereby incorporated by reference in its entirety). An exemplary CRISPR system includes the S. pyogenes Cas9 nuclease (Sp. Cas9), an extremely high-affinity (see Sternberg, S. H., Redding, S., Jinek, M., Greene, E. C. & Doudna, J. A. DNA interrogation by the CRISPR RNA-guided endonuclease Cas9. Nature 507, 62-67 (2014) hereby incorporated by reference in its entirety), programmable DNA-binding protein isolated from a type II CRISPR-associated system (see Garneau, J. E. et al. The CRISPR/Cas bacterial immune system cleaves bacteriophage and plasmid DNA. Nature 468, 67-71 (2010) and Jinek, M. et al. A programmable dual-RNA-guided DNA endonuclease in adaptive bacterial immunity. Science 337, 816-821 (2012) each of which are hereby incorporated by reference in its entirety). According to certain aspects, a nuclease null or nuclease deficient Cas9 can be used in the methods described herein. Such nuclease null or nuclease deficient Cas9 proteins are described in Gilbert, L. A. et al. CRISPR-mediated modular RNA-guided regulation of transcription in eukaryotes. Cell 154, 442-451 (2013); Mali, P. et al. CAS9 transcriptional activators for target specificity screening and paired nickases for cooperative genome engineering. Nature biotechnology 31, 833-838 (2013); Maeder, M. L. et al. CRISPR RNA-guided activation of endogenous human genes. Nature methods 10, 977-979 (2013); and Perez-Pinera, P. et al. RNA-guided gene activation by CRISPR-Cas9-based transcription factors. Nature methods 10, 973-976 (2013) each of which are hereby incorporated by reference in its entirety. The DNA locus targeted by Cas9 (and by its nuclease-deficient mutant, "dCas9" precedes a three nucleotide (nt) 5 '-NGG-3' "PAM" sequence, and matches a 15-22-nt guide or spacer sequence within a Cas9-bound RNA cofactor, referred to herein and in the art as a guide RNA. Altering this guide RNA is sufficient to target Cas9 or a nuclease deficient Cas9 to a target nucleic acid. In a multitude of CRISPR-based biotechnology applications (see Mali, P., Esvelt, K. M. & Church, G. M. Cas9 as a versatile tool for engineering biology. Nature methods 10, 957-963 (2013); Hsu, P. D., Lander, E. S. & Zhang, F. Development and Applications of CRISPR-Cas9 for Genome Engineering. Cell 157, 1262-1278 (2014); Chen, B. et al. Dynamic imaging of genomic loci in living human cells by an optimized CRISPR/Cas system. Cell 155, 1479-1491 (2013); Shalem, O. et al. Genome-scale CRISPR-Cas9 knockout screening in human cells. Science 343, 84-87 (2014); Wang, T., Wei, J. J., Sabatini, D. M. & Lander, E. S. Genetic screens in human cells using the CRISPR-Cas9 system. Science 343, 80-84 (2014); Nissim, L., Perli, S. D., Fridkin, A., Perez-Pinera, P. & Lu, T. K. Multiplexed and Programmable Regulation of Gene Networks with an Integrated RNA and CRISPR/Cas Toolkit in Human Cells. Molecular cell 54, 698-710 (2014); Ryan, O. W. et al. Selection of chromosomal DNA libraries using a multiplex CRISPR system. eLife 3 (2014); Gilbert, L. A. et al. Genome-Scale CRISPR-Mediated Control of Gene Repression and Activation. Cell (2014); and Citorik, R. J., Mimee, M. & Lu, T. K. Sequence-specific antimicrobials using efficiently delivered RNA-guided nucleases. Nature biotechnology (2014) each of which are hereby incorporated by reference in its entirety), the guide is often presented in a so-called sgRNA (single guide RNA), wherein the two natural Cas9 RNA cofactors (gRNA and tracrRNA) are fused via an engineered loop or linker.

According to one aspect, the Cas9 protein is an enzymatically active Cas9 protein, a Cas9 protein wild-type protein, a Cas9 protein nickase or a nuclease null or nuclease deficient Cas9 protein. Additional exemplary Cas9 proteins include Cas9 proteins attached to, bound to or fused with effector domains such as transcriptional regulators or epigenetic modifiers, such as transcriptional repressors as described herein.

According to certain aspects, the dCas9 protein or dCas9 and effector domain fusion protein may be delivered directly to a cell by methods known to those of skill in the art, including injection or lipofection, or as translated from its cognate mRNA, or transcribed from its cognate DNA into mRNA (and thereafter translated into protein). dCas9 or dCas9 fusion DNA and mRNA may be themselves introduced into cells through electroporation, transient and stable transfection (including lipofection) and viral transduction or other methods known to those of skill in the art. In exemplary embodiments, dCas9 or dCas9 fusion coding DNA sequence is packaged into recombinant lentiviral vectors and delivered to cells in vivo or in vitro.

Guide RNA Description

Embodiments of the present disclosure are directed to the use of a CRISPR/Cas system and, in particular, a guide RNA which may include one or more of a spacer sequence, a tracr mate sequence and a tracr sequence. The term spacer sequence is understood by those of skill in the art and may include any polynucleotide having sufficient complementarity with a target nucleic acid sequence to hybridize with the target nucleic acid sequence and direct sequence-specific binding of a CRISPR complex to the target sequence. The guide RNA may be formed from a spacer sequence covalently connected to a tracr mate sequence (which may be referred to as a crRNA) and a separate tracr sequence, wherein the tracr mate sequence is hybridized to a portion of the tracr sequence. According to certain aspects, the tracr mate sequence and the tracr sequence are connected or linked such as by covalent bonds by a linker sequence, which construct may be referred to as a fusion of the tracr mate sequence and the tracr sequence. The linker sequence referred to herein is a sequence of nucleotides, referred to herein as a nucleic acid sequence, which connect the tracr mate sequence and the tracr sequence. Accordingly, a guide RNA may be a two component species (i.e., separate crRNA and tracr RNA which hybridize together) or a unimolecular species (i.e., a crRNA-tracr RNA fusion, often termed an sgRNA).

According to certain aspects, the guide RNA is between about 10 to about 500 nucleotides. According to one aspect, the guide RNA is between about 20 to about 100 nucleotides. According to certain aspects, the spacer sequence is between about 10 and about 500 nucleotides in length. According to certain aspects, the tracr mate sequence is between about 10 and about 500 nucleotides in length. According to certain aspects, the tracr sequence is between about 10 and about 100 nucleotides in length. According to certain aspects, the linker nucleic acid sequence is between about 10 and about 100 nucleotides in length.

According to one aspect, embodiments described herein include guide RNA having a length including the sum of the lengths of a spacer sequence, tracr mate sequence, tracr sequence, and linker sequence (if present). Accordingly, such a guide RNA may be described by its total length which is a sum of its spacer sequence, tracr mate sequence, tracr sequence, and linker sequence (if present). According to this aspect, all of the ranges for the spacer sequence, tracr mate sequence, tracr sequence, and linker sequence (if present) are incorporated herein by reference and need not be repeated. A guide RNA as described herein may have a total length based on summing values provided by the ranges described herein. Aspects of the present disclosure are directed to methods of making such guide RNAs as described herein by expressing constructs encoding such guide RNA using promoters and terminators and optionally other genetic elements as described herein.

According to certain aspects, the guide RNA may be delivered directly to a cell as a native species by methods known to those of skill in the art, including injection or lipofection, or as transcribed from its cognate DNA, with the cognate DNA introduced into cells through electroporation, transient and stable transfection (including lipofection) and viral transduction. In exemplary embodiments, guide RNA coding sequence is packaged into recombinant lentiviral vectors and delivered to cells in vivo or in vitro.

Transcription Regulator Description

According to one aspect, an engineered Cas9-gRNA system is provided which enables RNA-guided DNA regulation in cells by tethering transcriptional repression domains to a nuclease-null Cas9 (dCas9). According to one aspect of the present disclosure, one or more transcriptional regulatory proteins or effector domains (such terms are used interchangeably) are joined or otherwise connected to a nuclease-null Cas9. The dCas9 and the effector domains correspond to targeted loci. Accordingly, aspects of the present disclosure include methods and materials for localizing effector domains to targeted loci by fusing, connecting or joining such domains to dCas9.

Cells

Cells according to the present disclosure include any cell into which the disclosed nucleic acids can be introduced and expressed as described herein. It is to be understood that the basic concepts of the present disclosure described herein are not limited by cell type. In some embodiments, the cell is from an embryo. The cell can be a stem cell, zygote, or a germ line cell. In embodiments where the cell is a stem cell, the stem cell is an embryonic stem cell or pluripotent stem cell. In other embodiments, the cell is a somatic cell. In embodiments, where the cell is a somatic cell, the somatic cell is a eukaryotic cell or prokaryotic cell. The eukaryotic cell can be an animal cell, such as from a pig, mouse, rat, rabbit, dog, horse, cow, non-human primate, human.

Vectors

Vectors are contemplated for use with the methods and constructs described herein. The term "vector" includes a nucleic acid molecule capable of transporting another nucleic acid to which it has been linked. Vectors used to deliver the nucleic acids to cells as described herein include vectors known to those of skill in the art and used for such purposes. Certain exemplary vectors may be plasmids, lentiviruses or adeno-associated viruses known to those of skill in the art. Vectors include, but are not limited to, nucleic acid molecules that are single-stranded, doublestranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, lentiviruses, replication defective retroviruses, adenoviruses, replication defective adenoviruses, and adeno-associated viruses). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." Common expression vectors of utility in recombinant DNA techniques are often in the form of plasmids. Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell).

Methods of non-viral delivery of nucleic acids or native DNA binding protein, native guide RNA or other native species include lipofection, microinjection, biolistics, virosomes, liposomes, immunoliposomes, polycation or lipid: nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424; WO 91/16024. Delivery can be to cells (e.g. in vitro or ex vivo administration) or target tissues (e.g. in vivo administration). The term native includes the protein, enzyme or guide RNA species itself and not the nucleic acid encoding the species.

Regulatory Elements and Terminators and Tags

Regulatory elements are contemplated for use with the methods and constructs described herein. The term "regulatory element" is intended to include promoters, enhancers, internal ribosomal entry sites (IRES), and other expression control elements (e.g. transcription termination signals, such as polyadenylation signals and poly-U sequences). Such regulatory elements are described, for example, in Goeddel, GENE EXPRESSION TECHNOLOGY: METHODS IN ENZYMOLOGY 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g. liver, pancreas), or particular cell types (e.g. lymphocytes). Regulatory elements may also direct expression in a temporal-dependent manner, such as in a cell-cycle dependent or developmental stage-dependent manner, which may or may not also be tissue or cell-type specific. In some embodiments, a vector may comprise one or more pol III promoter (e.g. 1, 2, 3, 4, 5, or more pol III promoters), one or more pol II promoters (e.g. 1, 2, 3, 4, 5, or more pol II promoters), one or more pol I promoters (e.g. 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter and Pol II promoters described herein. Also encompassed by the term "regulatory element" are enhancer elements, such as WPRE; CMV enhancers; the R-U5' segment in LTR of HTLV-I (Mol. Cell. Biol., Vol. 8(1), p. 466-472, 1988); SV40 enhancer; and the intron sequence between exons 2 and 3 of rabbit β-globin (Proc. Natl. Acad. Sci. USA., Vol. 78(3), p. 1527-31, 1981). It will be appreciated by those skilled in the art that the design of the expression vector can depend on such factors as the choice of the host cell to be transformed, the level of expression desired, etc. A vector can be introduced into host cells to thereby produce transcripts, proteins, or peptides, including fusion proteins or peptides, encoded by nucleic acids as described herein (e.g., clustered regularly interspersed short palindromic repeats (CRISPR) transcripts, proteins, enzymes, mutant forms thereof, fusion proteins thereof, etc.).

Aspects of the methods described herein may make use of terminator sequences. A terminator sequence includes a section of nucleic acid sequence that marks the end of a gene or operon in genomic DNA during transcription. This sequence mediates transcriptional termination by providing signals in the newly synthesized mRNA that trigger processes which release the mRNA from the transcriptional complex. These processes include the direct interaction of the mRNA secondary structure with the complex and/or the indirect activities of recruited termination factors. Release of the transcriptional complex frees RNA polymerase and related transcriptional machinery to begin transcription of new mRNAs. Terminator sequences include those known in the art and identified and described herein.

Aspects of the methods described herein may make use of epitope tags and reporter gene sequences. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporter genes include, but are not limited to, glutathione-S-transferase (GST), horseradish peroxidase (HRP), chloramphenicol acetyltransferase (CAT) beta-galactosidase, betaglucuronidase, luciferase, green fluorescent protein (GFP), HcRed, DsRed, cyan fluorescent protein (CFP), yellow fluorescent protein (YFP), and autofluorescent proteins including blue fluorescent protein (BFP).

Fusion Constructs

The RNA-guided endonuclease Cas9 can be converted into a programmable transcriptional repressor, yet inefficiencies in target gene silencing have limited its utility. Embodiments of the present disclosure are directed to methods and compositions for an improved dCas9 based transcriptional repressor. In some embodiments, the improved dCas9 based transcriptional repressor includes a fusion of dCas9 protein or functional fragments thereof and an effector domain. In one embodiment, the effector domain comprises a transcriptional repressor domain. In another embodiment, the effector domain comprises multiple transcriptional repressor domains fused together. Transcriptional repressor domains are known to those of skill in the art. In certain embodiments, the present disclosure contemplates fusions of multiple same or different transcriptional domains to the C and/or N ends of a dCas9 protein. According to certain aspects, the present disclosure provides the screening of a large number of repressor domains in combination with rational design to engineer a more potent dCas9 based repressor. The repressor domains that were screened are indicated in the figures and tables herein. In exemplary embodiments, the improved Cas9 based repressor is based on the C-terminal fusion of a rationally designed bipartite repressor KRAB-MeCP2 to nuclease-null Cas9 (dCas9). In one embodiment, a highly effective transcriptional repressor is a dCas9-KRAB-MeCP2 transcriptional repressor. Characterization of this novel repressor proved its superiority to previous CRISPR repressor technology for both single and multiplex gene targeting and in silencing coding and non-coding genes. Compared to previous dCas9 repressor or dCas9 KRAB repressor, this novel dCas9-KRAB-MeCP2 repressor demonstrated transcriptional repression of target genes by more than 2, 3, 4, 5, 6, 7, 8, 9 and 10 folds. In a series of guide RNA screens, it is demonstrated that the improved dCas9-KRAB-MeCP2 repressor is capable of delivering richer datasets improving the results of gRNA library screens.

EXAMPLES

The following examples are set forth as being representative of the present disclosure. These examples are not to be construed as limiting the scope of the present disclosure as these and other equivalent embodiments will be apparent in view of the present disclosure, figures and accompanying claims.

Example I

Identification of dCas9-KRAB-MeCP2

Figure 1B:
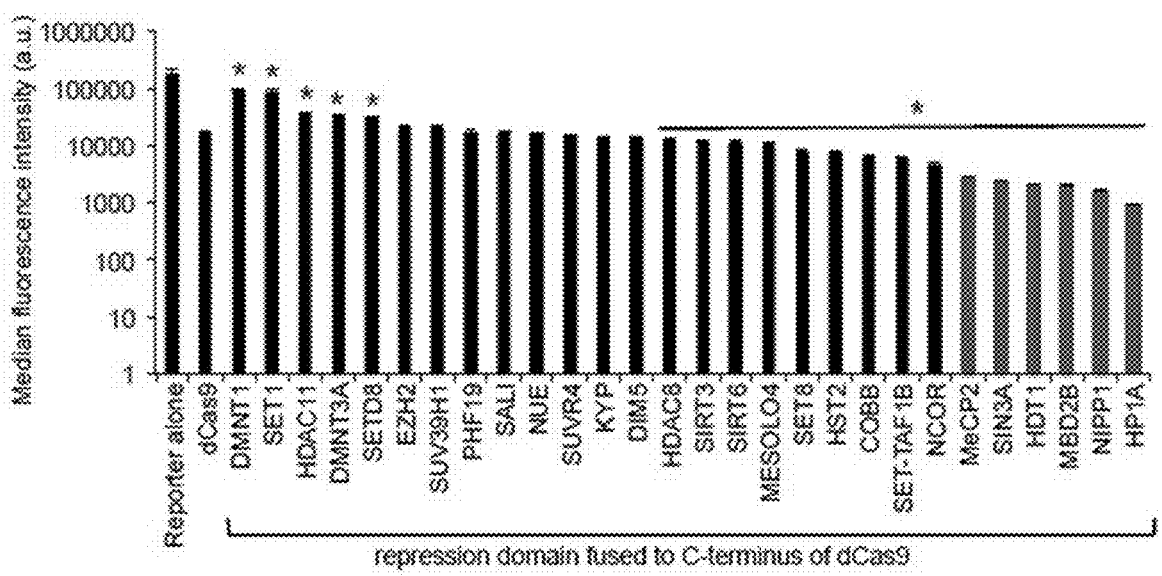
Figure 2:
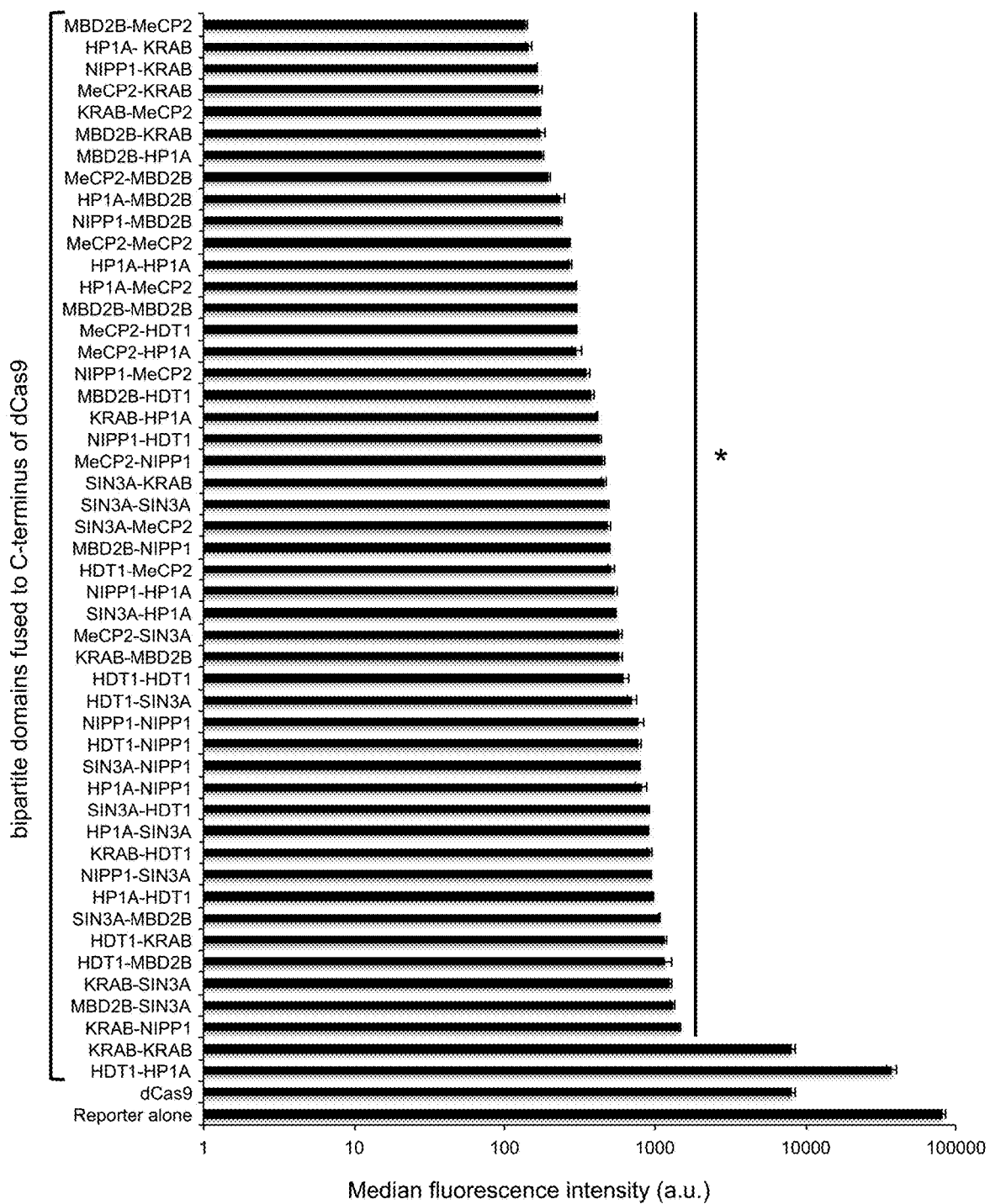
FIG. 2 depicts results of reporter screen of 49 dCas9 bipartite repressors. A series of all pairwise repeating and non-repeating bipartite repressors were generated using KRAB and the six top-performing domains identified from the initial screen (MeCP2, SIN3A, HDT1, MBD2B, NIPP1, and HP1a). Each repressor was tested using the same fluorescent reporter assay as in FIGS. 1A-1B. n=two independent transfections. Data are presented as median fluorescence±s.e.m. * indicates $p<0.005$ vs. dCas9.

To begin to design a more potent Cas9 repressor, >20 different effector domains known to play a role in transcriptional regulation and gene silencing were separately fused to the C-terminus of dCas9. The resulting dCas9 fusion proteins were then transfected into HEK293T cells along with an sgRNA targeting the promoter of an enhanced yellow fluorescent protein (EYFP) reporter gene. It was found that the majority of dCas9 fusions were able to repress EYFP expression, with a few exhibiting greater repression (up to 8-fold) compared to dCas9 (FIGS. 1A & 1B). Previous work from several groups including our own has shown that recruitment of multiple transcriptional effector domains to a single locus allows for a synergistic increase in dCas9-mediated gene activation (Chavez A, Scheiman J, Vora S, Pruitt B W, Tuttle M, P R Iyer E, Lin S, Kiani S, Guzman C D, Wiegand D J, Ter-Ovanesyan D, Braff J L, Davidsohn N, Housden B E, Perrimon N, Weiss R, Aach J, Collins J J, Church G M, "Highly efficient Cas9-mediated transcriptional programming," Nat Methods. 2015 April; 12(4):326-8, Epub 2015 Mar. 2; Konermann S, Brigham M D, Trevino A E, Joung J, Abudayyeh O O, Barcena C, Hsu P D, Habib N, Gootenberg J S, Nishimasu H, Nureki O, Zhang F, "Genome-scale transcriptional activation by an engineered CRISPR-Cas9 complex," Nature. 2015 Jan. 29; 517(7536): 583-8, Epub 2014 Dec. 10; Zalatan J G, Lee M E, Almeida R, Gilbert L A, Whitehead E H, La Russa M, Tsai J C, Weissman J S, Dueber J E, Qi L S, Lim W A, "Engineering complex synthetic transcriptional programs with CRISPR RNA scaffolds," Cell. 2015 Jan. 15; 160(1-2):339-50, Epub 2014 Dec. 18; Tanenbaum M E, Gilbert L A, Qi L S, Weissman J S, Vale R D, "A protein-tagging system for signal amplification in gene expression and fluorescence imaging," Cell. 2014 Oct. 23; 159(3):635-46, Epub 2014 Oct. 9). To determine whether dCas9-mediated transcriptional repression could similarly benefit from recruitment of multiple effector domains, a library of dCas9 bipartite repressors consisting of the commonly used KRAB repressor and the six top-performing domains from our initial screen (MeCP2, SIN3A, HDT1, MBD2B, NIPP1, and HP1A) were generated. The library contained all pairwise repeating and non-repeating combinations of the seven selected domains. As expected, many bipartite fusion proteins showed significant improvement, ranging from 5- to 60-fold greater repression of EYFP compared to dCas9 (FIG. 2).

Figure 3A:
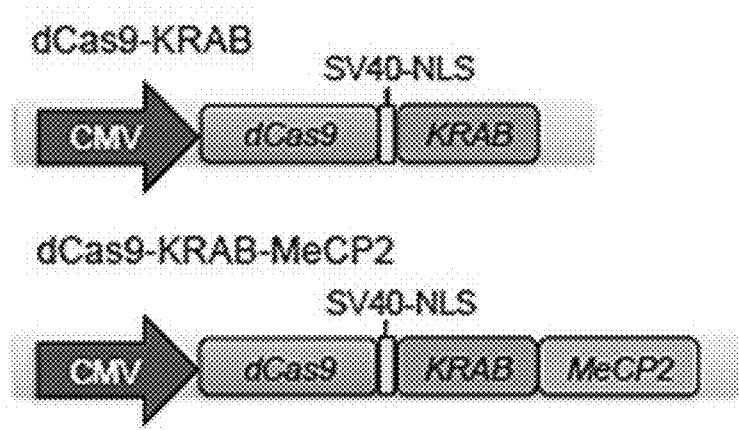
FIGS. 3A-3C depict repression of endogenous genes using dCas9-KRAB-MeCP2.
Figure 4:
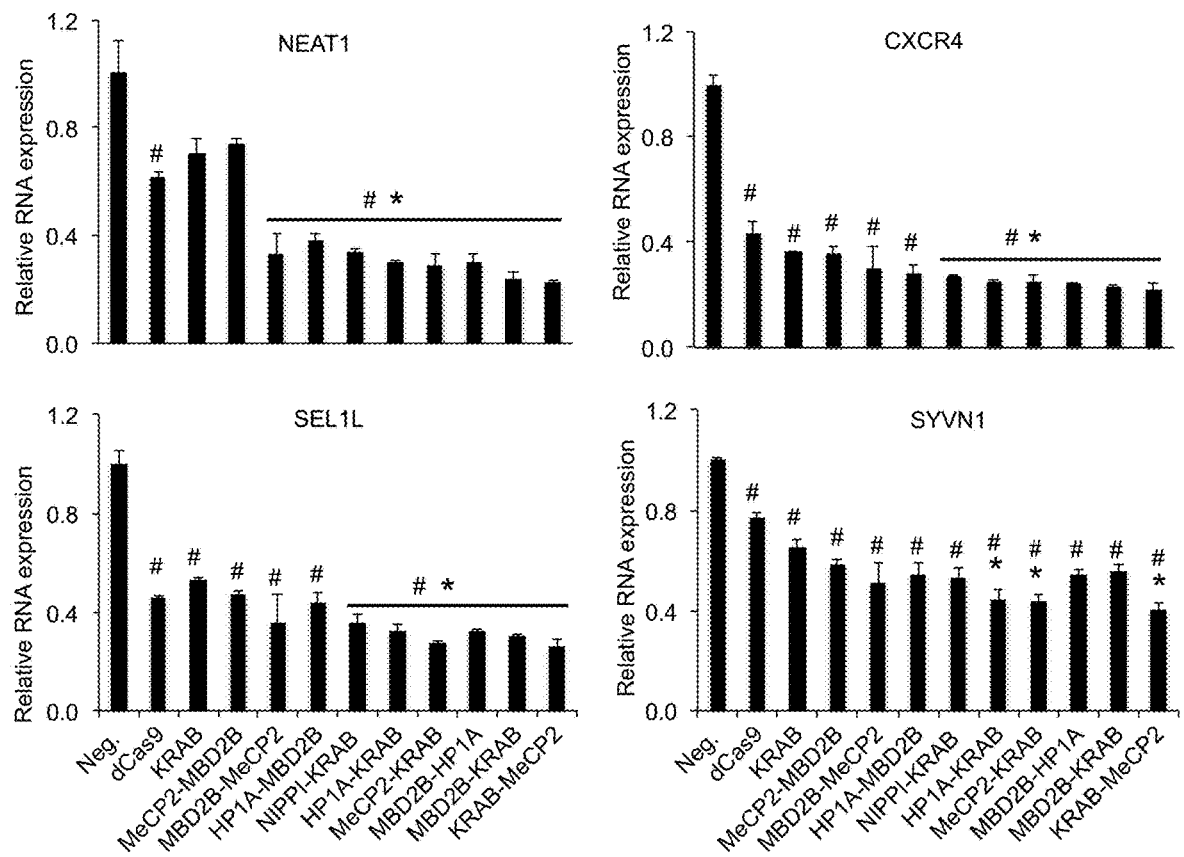
FIG. 4 depicts results of repression of endogenous genes using top bipartite fusions. HEK293T cells were co-transfected with sgRNAs against the indicated four genes simultaneously with the labeled repressors, and samples were collected for RNA extraction at 4 days post transfection. The expression levels of targeted genes were measured by RT-qPCR. A dCas9 protein fused to KRAB-MeCP2 domains consistently showed stronger level of repression compared to other constructs tested. n=two independent transfections. Data are presented as mean±s.e.m. # indicates $p<0.05$ vs. negative control. * indicates $p<0.05$ vs. dCas9-KRAB.
Figure 5:
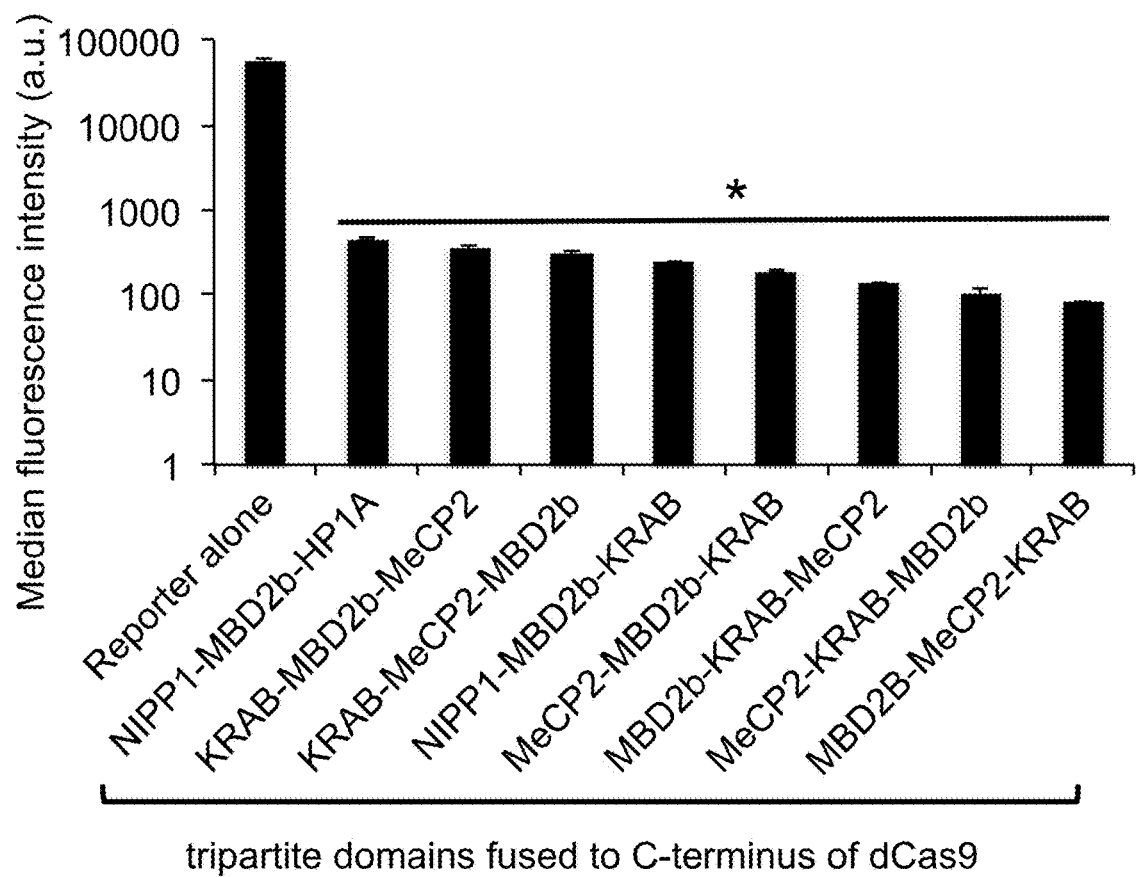
FIG. 5 depicts results of reporter screen of 8 dCas9 tripartite repressors. A series of rationally designed tripartite repressors were generated based on the top-performing bipartite repression domains to test whether the strength of repression could be improved by appending additional domains. Each repressor was tested using the same fluorescent reporter assay as in FIG. 1B. n=two independent transfections. Data are presented as median fluorescence±s.e.m. * indicates $p<0.005$ vs. reporter alone.
Figure 6:
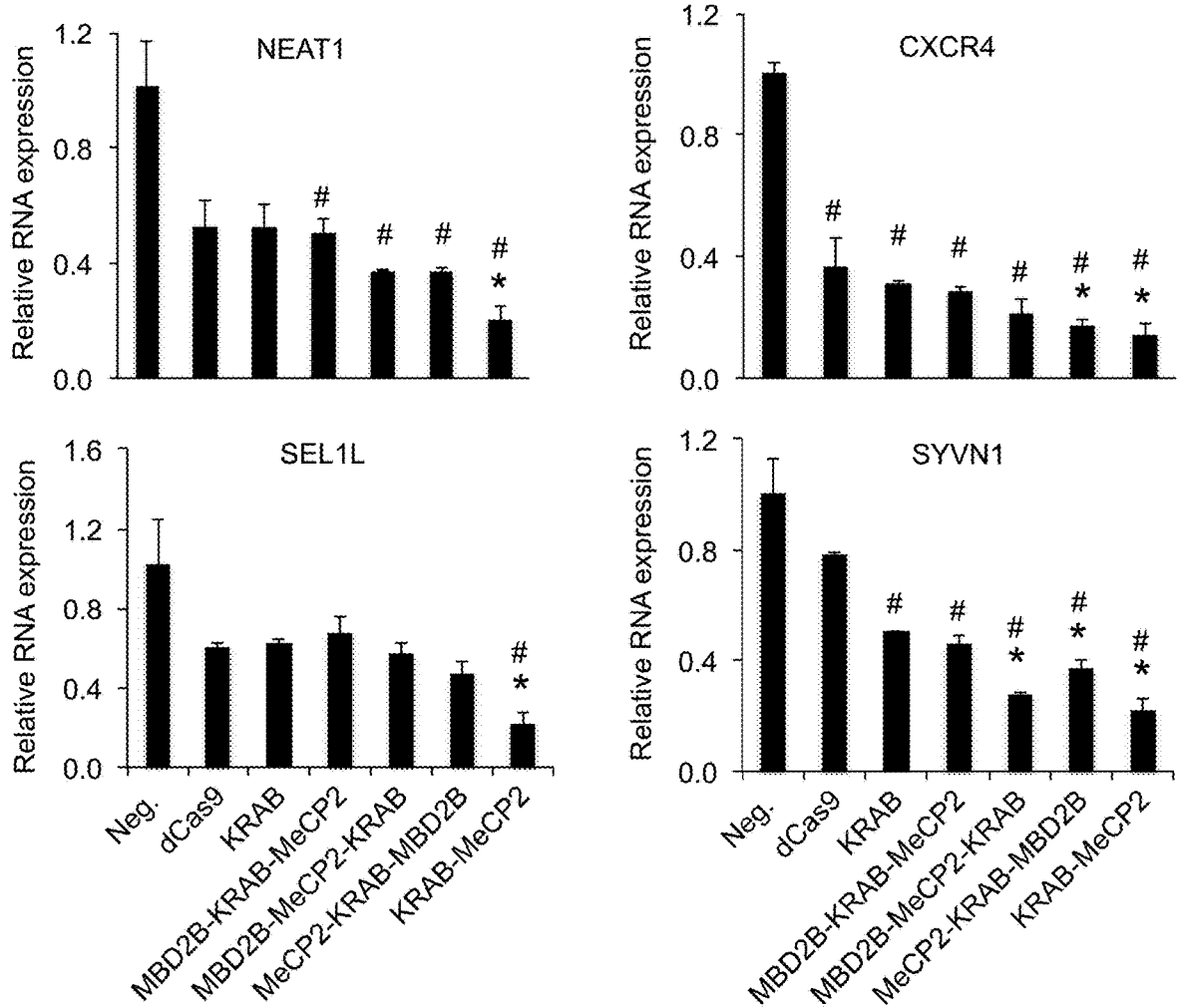
FIG. 6 depicts results of repression of endogenous genes using top tripartite fusions as compared to the bipartite KRAB-MeCP2 repressor. The three best performing tripartite repressors based on the reporter screen were selected and tested against a series of endogenous loci, along with dCas9-KRAB-MeCP2. RNA levels of the four indicated genes from a multiplexed repression experiment were measured using RT-qPCR. dCas9-KRAB-MeCP2 consistently achieved stronger repression of all tested genes as compared to other dCas9 fusion proteins. n=two independent transfections. Data are presented as mean±s.e.m. # indicates $p<0.05$ vs. negative control. * indicates $p<0.05$ vs. dCas9-KRAB.

Having done the initial studies with a synthetic reporter gene, it was next determined whether the most potent repressors could also downregulate endogenous target genes. Nine bipartite repressors for further characterization were selected. Each of the dCas9 variants were co-transfected into HEK293T cells along with a set of sgRNAs targeting four different endogenous genes. While varying degrees of gene repression were observed depending upon the target gene, the dCas9 repressor consisting of KRAB and the TRD domain of MeCP2, named dCas9-KRAB-MeCP2 (FIG. 3A and Table 1), was the most potent across all targets (FIG. 4). A series of tripartite fusion proteins were also generated to test if further improvements in repression could be achieved by employing three different effector domains. No significant improvement in gene silencing was obtained using any of the designed tripartite repressors as compared to the dCas9-KRAB-MeCP2 protein (FIGS. 4 and 5).

Example II

Improved Repression Using dCas9-KRAB-MeCP2

Figure 3B:
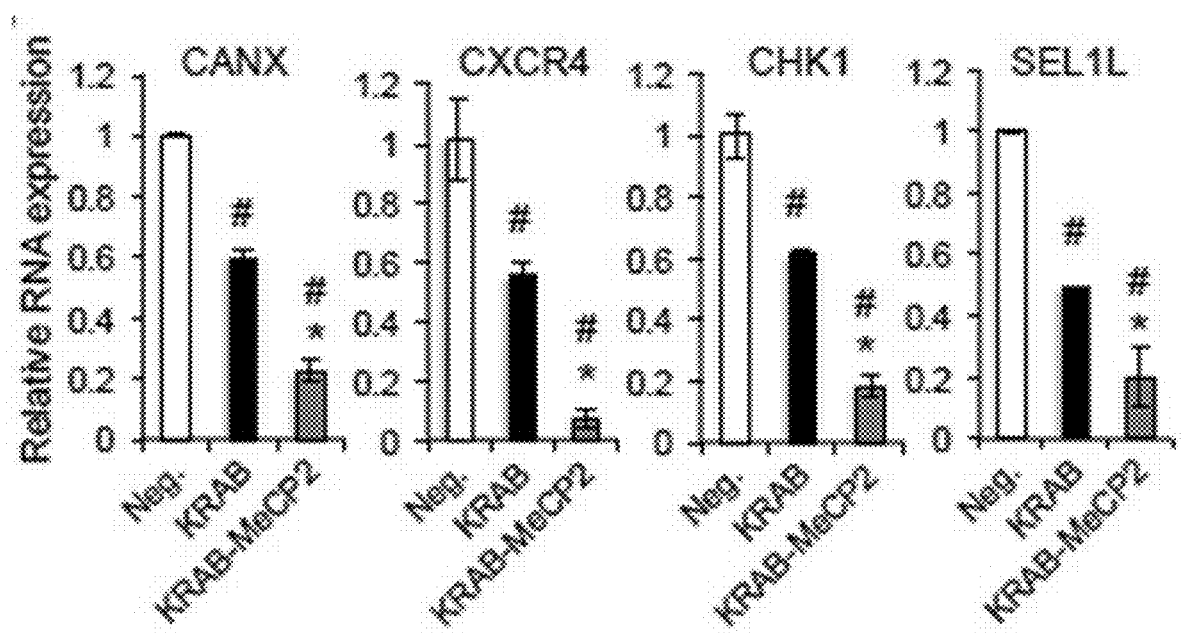
Figure 3C:
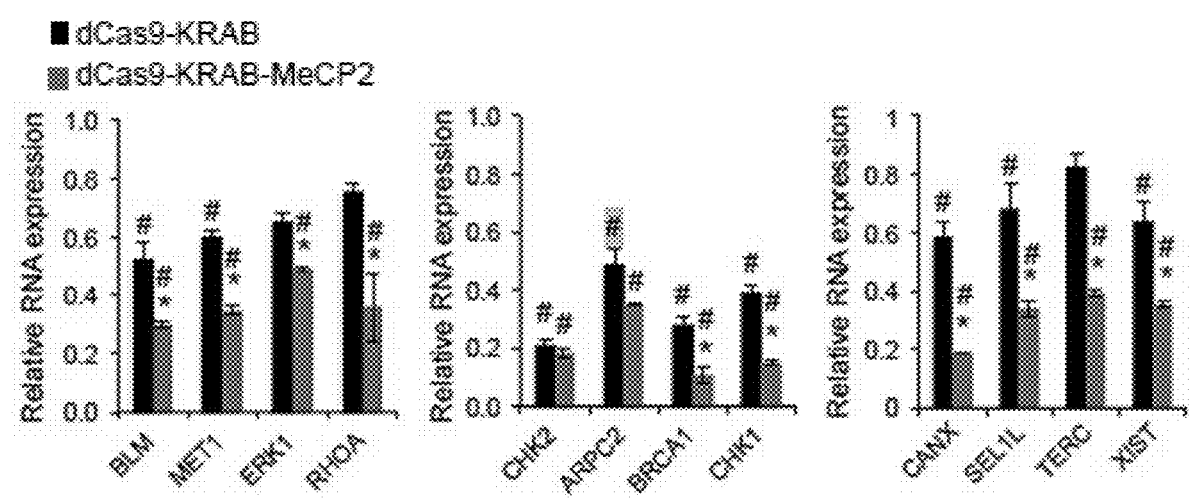
Figure 7A:
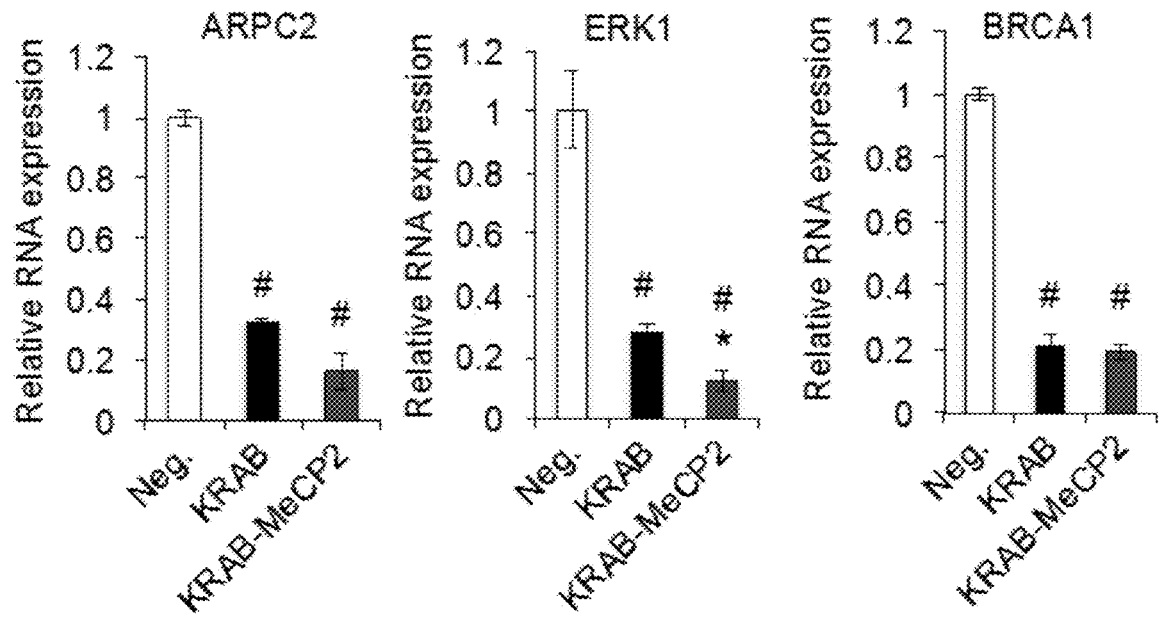
FIGS. 7A-7B depict results of repression of endogenous genes using dCas9-KRAB and dCas9-KRAB-MeCP2.
Figure 7B:
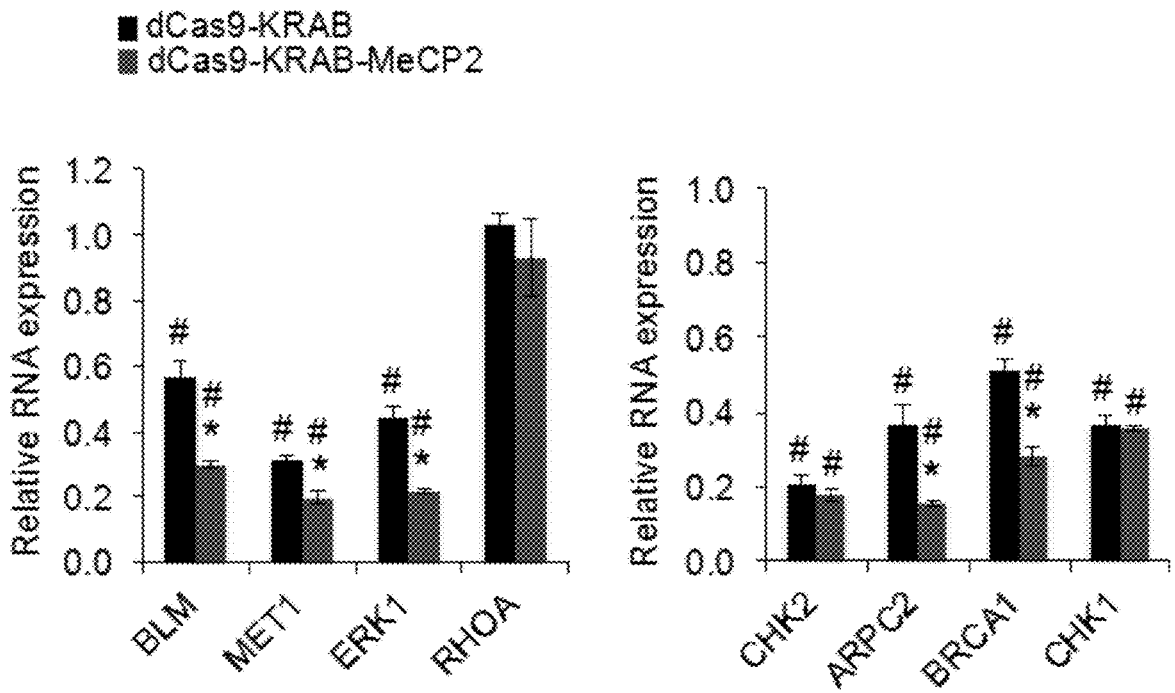

It was next systematically compared the activity of dCas9-KRAB-MeCP2 to that of the current gold-standard dCas9-KRAB repressor by individually targeting a wide range of endogenous loci in HEK293T cells. For the majority of genes tested dCas9-KRAB-MeCP2 showed improved repression on average decreasing gene expression by 80% as compared to 55% with dCas9-KRAB (FIG. 3B and FIG. 7A). A significant advantage afforded by CRISPR-based regulators is their ability to perform multiplexed gene regulation by simultaneously introducing multiple sgRNAs (Cong L, Ran F A, Cox D, Lin S, Barretto R, Habib N, Hsu P D, Wu X, Jiang W, Marraffini L A, Zhang F, "Multiplex genome engineering using CRISPR/Cas systems," Science. 2013 Feb. 15; 339(6121):819-23, Epub 2013 Jan. 3; Mali P, Yang L, Esvelt K M, Aach J, Guell M, DiCarlo J E, Norville J E, Church G M, "RNA-guided human genome engineering via Cas9," Science. 2013 Feb. 15; 339(6121):823-6, Epub 2013 Jan. 3). To test whether dCas9-KRAB-MeCP2 could more effectively down-regulate the expression of multiple genes, four sgRNAs each targeting a different locus were co-transfected into HEK293T cells (FIG. 3C). dCas9-KRAB-MeCP2 showed significantly improved multiplex repression for all genes tested except for two where it showed similar activity to dCas9-KRAB. To ensure that the effects observed were not unique to the sgRNAs selected, a new group of sgRNAs against the same set of target genes were designed and another round of multiplex repression experiments were performed. With this new group of sgRNAs, dCas9-KRAB-MeCP2 again showed improved activity for the majority of targets tested (FIG. 7B).

Figure 8A:
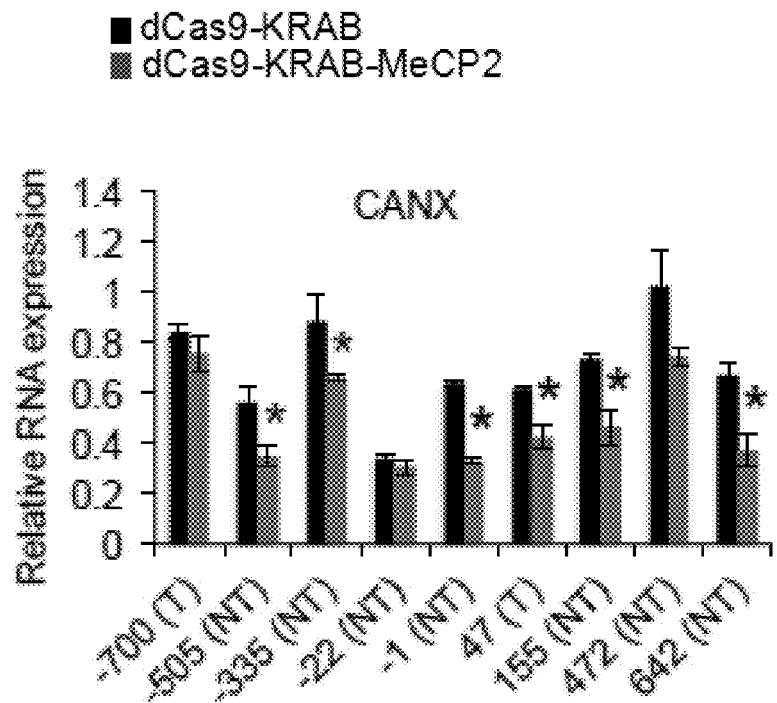
FIGS. 8A-8C depict results of characterizing the dCas9-KRAB-MeCP2 targeting window and examining the effects of sgRNA selection.
Figure 8B:
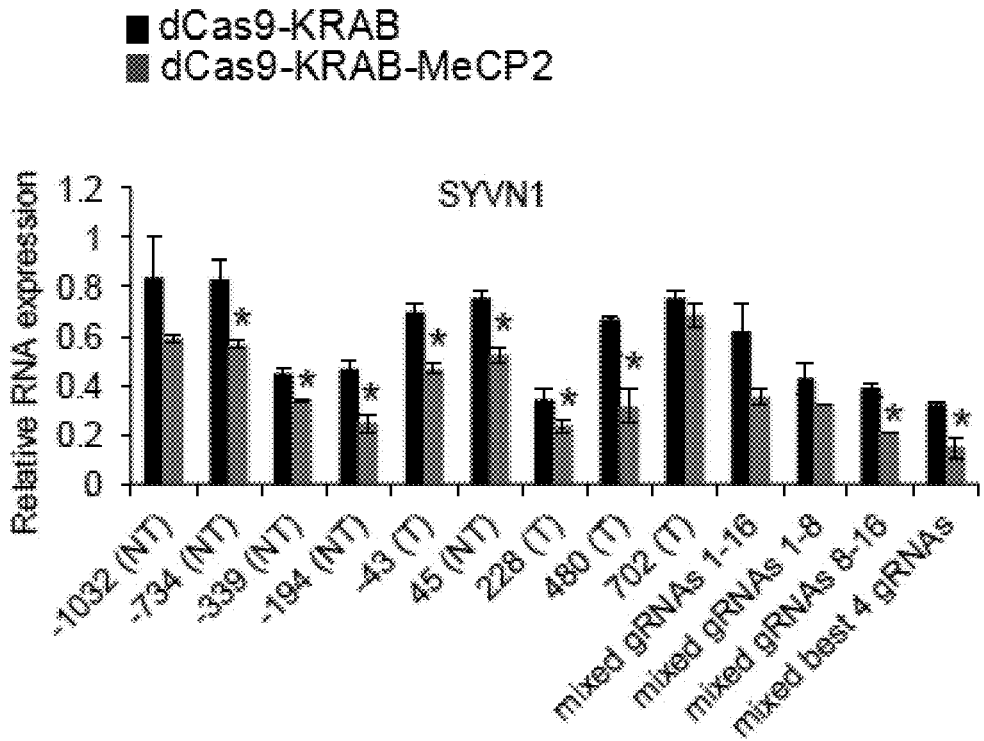
Figure 8C:
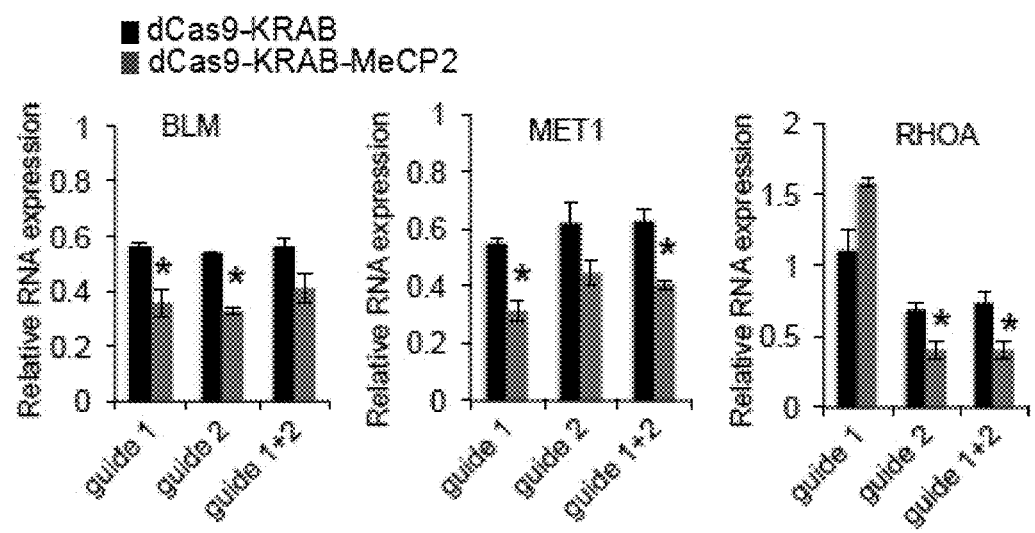
Figure 9:
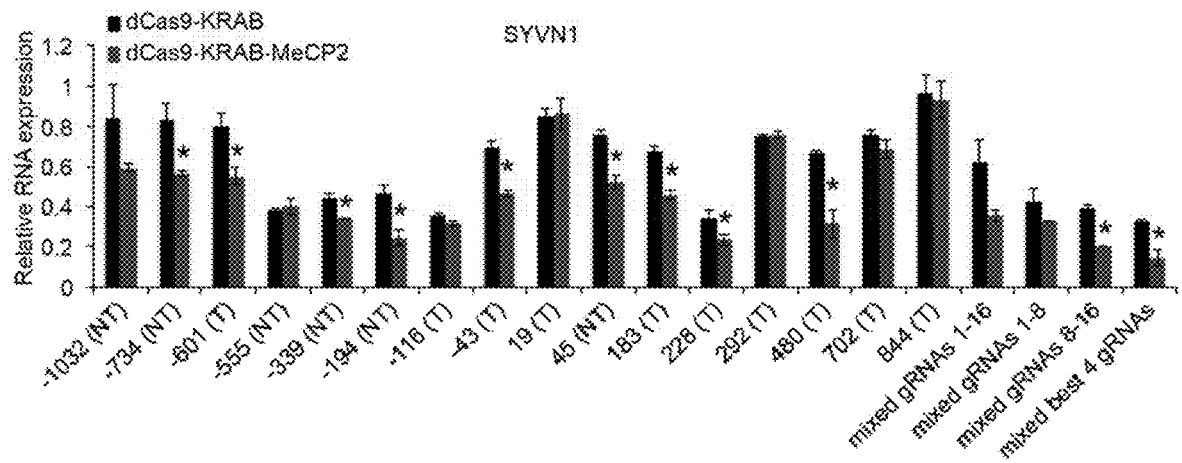
FIG. 9 depicts the effect of an array of sgRNAs tiling along the regulatory sequence (promoter and untranslated region) of SYVN1 in combination with either dCas9-KRAB or dCas9-KRAB-MeCP2. n=two independent transfections. Data are presented as mean±s.e.m. * indicates $p<0.05$ vs. dCas9-KRAB.

Previous characterization of dCas9-KRAB has shown that for optimal performance, the sgRNA with which it is complexed must be directed to a region in close proximity (−50 to +200 bp) to the transcriptional start site (TSS) of the target gene (Gilbert L A, Horlbeck M A, Adamson B, Villalta J E, Chen Y, Whitehead E H, Guimaraes C, Panning B, Ploegh H L, Bassik M C, Qi L S, Kampmann M, Weissman J S, "Genome-Scale CRISPR-Mediated Control of Gene Repression and Activation," Cell. 2014 Oct. 23; 159(3):647-61, Epub 2014 Oct. 9). To examine if similar constraints apply to dCas9-KRAB-MeCP2, an array of sgRNAs targeting the template and non-template strands within a range of 1 kb upstream and downstream of the TSS for two different genes (CANX and SYVN1) were designed. With none of the tested sgRNAs did dCas9-KRAB exhibit improved repression compared to dCas9-KRAB-MeCP2. In contrast, 15 out of 25 sgRNAs tested showed significantly improved repression with dCas9-KRAB-MeCP2. These results were independent of the DNA strand targeted and whether or not the sgRNA was directed outside of the previously described optimal targeting window (FIGS. 8A & 8B and FIG. 9). These data suggest that the relatively constrained targeting parameters exhibited by dCas9-KRAB can be considerably expanded by utilizing dCas9-KRAB-MeCP2, a particular benefit for genes and genomes that are poorly annotated. Initial studies with CRISPR-repressors suggested that using multiple sgRNAs targeting the same locus led to marked improvement in gene knockdown (Qi L S, Larson M H, Gilbert L A, Doudna J A, Weissman J S, Arkin A P, Lim W A, "Repurposing CRISPR as an RNA-guided platform for sequence-specific control of gene expression," Cell. 2013 Feb. 28; 152(5): 1173-8). In contrast to these results, neither dCas9-KRAB nor dCas9-KRAB-MeCP2 showed improved repression when multiple guides against the same target were used; rather, they exhibited an activity that appeared to be dictated by the most potent guide within the set tested, consistent with recent observations (Shipeng Shao, Lei Chang, Yuao Sun, Yingping Hou, Xiaoying Fan, and Yujie Sun, "Multiplexed sgRNA Expression Allows Versatile Single Nonrepetitive DNA Labeling and Endogenous Gene Regulation," ACS Synth. Biol., 2018, 7 (1), pp 176-186) (FIGS. 8B & 8C).

Example III

The Effect of dCas9-KRAB-MeCP2 is Highly Specific

Figure 10A:
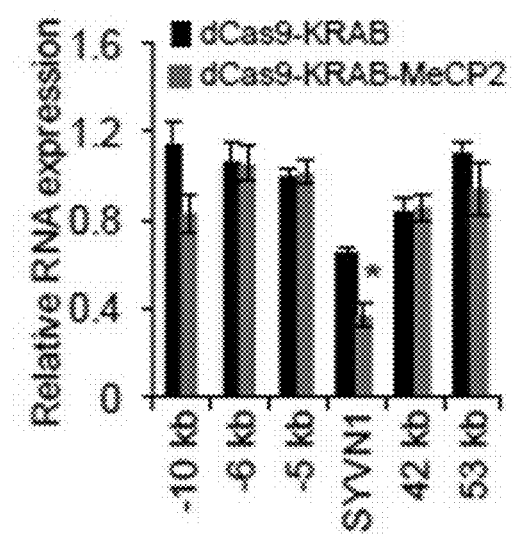
FIGS. 10A-10B depict that dCas9-KRAB-MeCP2-mediated repression is highly specific in human cells.
Figure 11A:
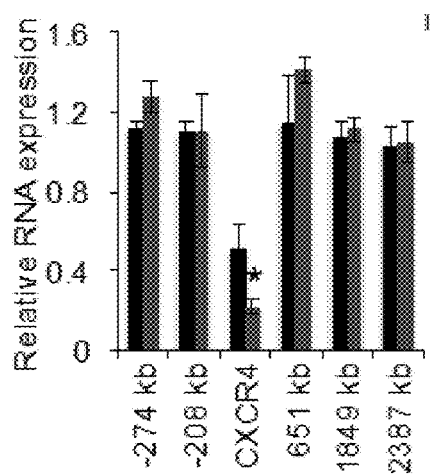
FIGS. 11A-11B depict that dCas9-KRAB-MeCP2-mediated repression is highly specific in human cells.

Having determined that our dCas9-KRAB-MeCP2 repressor was more potent than previous tools, its targeting specificity was next examined. Because effector domains that recruit chromatin modifiers can cause widespread epigenetic changes over large regions of DNA (Stolzenburg S, Beltran A S, Swift-Scanlan T, Rivenbark A G, Rashwan R, Blancafort P, "Stable oncogenic silencing in vivo by programmable and targeted de novo DNA methylation in breast cancer," Oncogene. 2015 October; 34(43):5427-35, Epub 2015 Feb. 16; Li F, Papworth M, Minczuk M, Rohde C, Zhang Y, Ragozin S, Jeltsch A, "Chimeric DNA methyltransferases target DNA methylation to specific DNA sequences and repress expression of target genes," Nucleic Acids Res. 2007; 35(1):100-12. Epub 2006 Dec. 6; Stepper P, Kungulovski G, Jurkowska R Z, Chandra T, Krueger F, Reinhardt R, Reik W, Jeltsch A, Jurkowski T P, "Efficient targeted DNA methylation with chimeric dCas9-Dnmt3a-Dnmt3L methyltransferase," Nucleic Acids Res. 2017 Feb. 28; 45(4):1703-1713), off-target effects were assayed for by probing the expression of neighboring genes when either SYVN1 or CXCR4 was targeted (FIG. 10A and FIG. 11A). No significant off-target effect was observed on the neighboring genes that were examined.

Figure 10B:
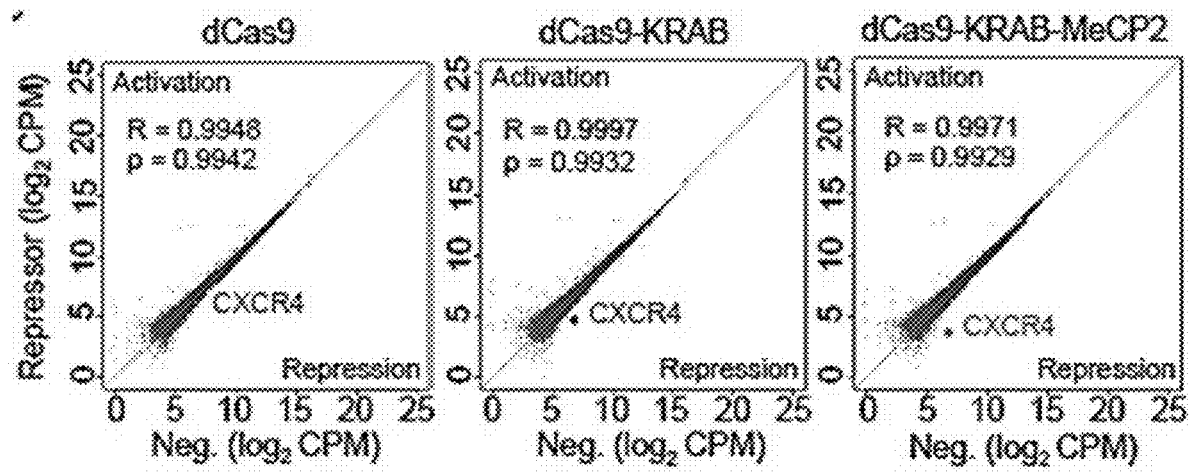
Figure 11B:
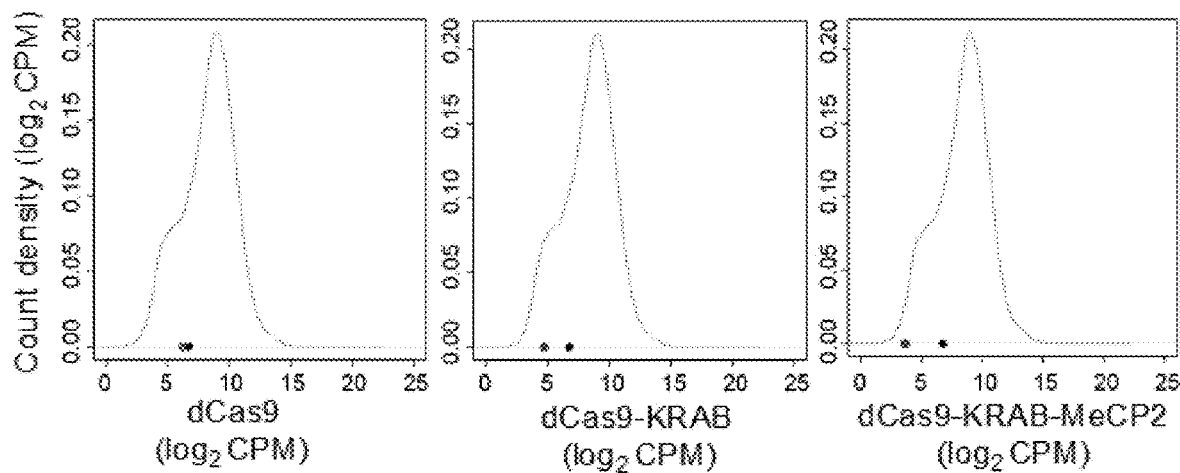

To evaluate the specificity of our dCas9-KRAB-MeCP2 repressor on a genome-wide scale, the CXCR4 gene was targeted and whole-transcriptome sequencing (RNA-seq) was performed. These results were then compared to those obtained from cells transfected with either dCas9 or dCas9-KRAB. It was found that all dCas9-repressors were highly-correlated with the negative control, cells transfected with sgRNA only, indicating that the presence of repressors did not lead to global perturbations in gene expression (FIG. 10B). The target gene, CXCR4 was downregulated to a different degree by all analyzed dCas9-repressors, with the strongest repression signal achieved by dCas9-KRAB-MeCP2 (FIG. 10B and FIG. 11B). In differential expression analysis of dCas9, dCas9-KRAB and dCas9-KRAB-MeCP2 relative to the negative control, a small overlapping set of genes with changes in expression were noted (FIGS. 12A-12D and FIGS. 13A-13C and Table 2). When examined further, none of these genes showed a near sequence match to the CXCR4 targeting sgRNA, suggesting that these changes did not result from inappropriate targeting of dCas9 to each of the loci with altered expression.

Figure 14A:
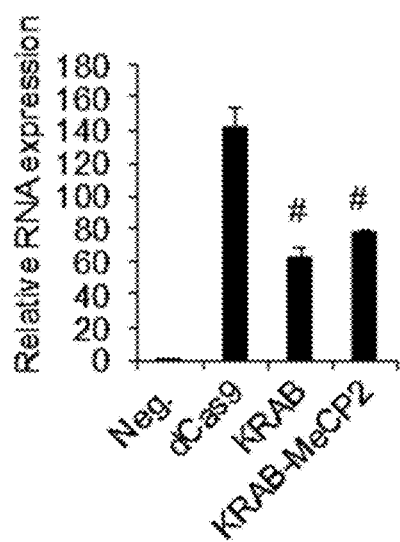
FIGS. 14A-14B depict results of target gene expression.
Figure 14B:
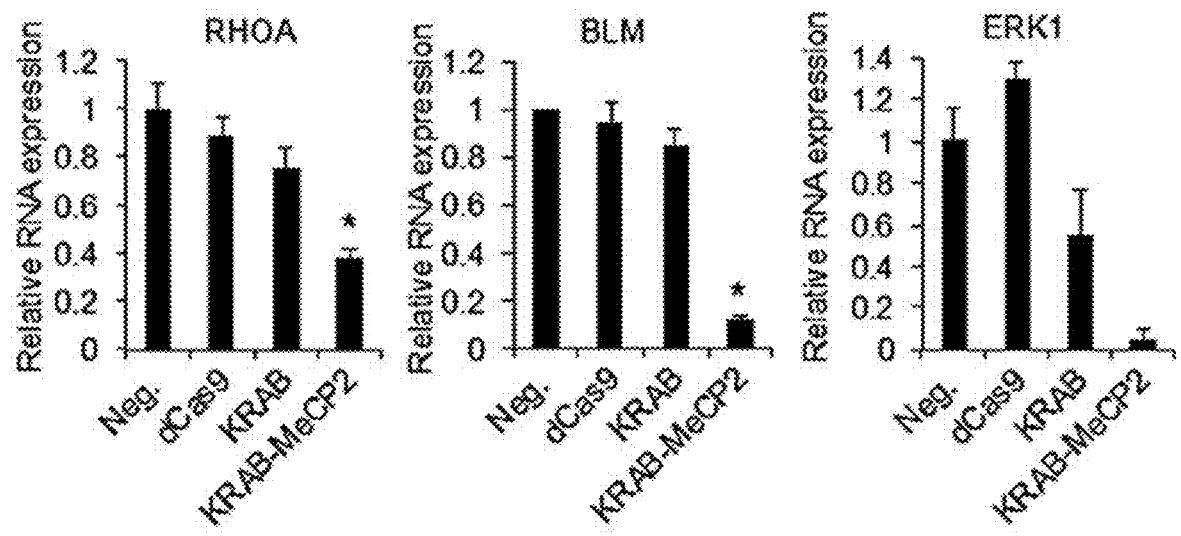

Example IV dCas9-KRAB-MeCP2 Efficiently Suppresses Genes when Used at Library Scales One of the most powerful uses of CRISPR-Cas9 technology is to enable facile genome-wide screens. To determine whether our enhanced repressor was amenable to such screening, the near-haploid human cell line HAP1 was used to generate heterogenous populations of cell lines expressing either dCas9, dCas9-KRAB, or dCas9-KRAB-MeCP2. All lines showed similar levels of dCas9 expression along with the expected repression behavior (FIGS. 14A and 14B).

Figure 15:
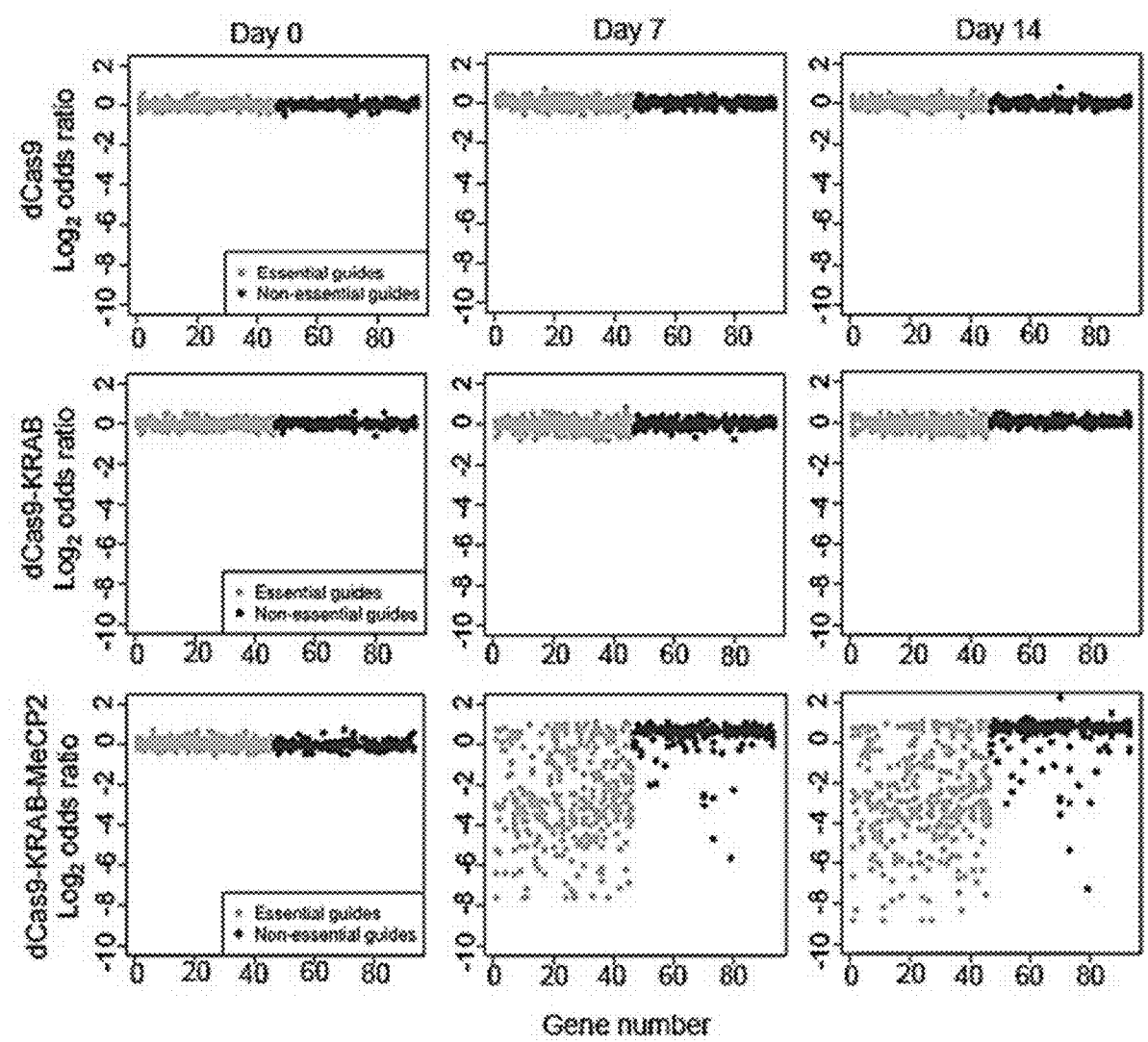
FIG. 15 depicts dCas9-KRAB-MeCP2 outperforms previous tools in a CRISPR repressor screen. HAP1 cells expressing the indicated repressor were infected with a lentiviral sgRNA library and treated with puromycin at 2 d after infection. Cells were collected for DNA extraction immediately after puromycin selection (day 0), and passaged 2 times per week with aliquots taken for sequencing on day 7 and day 14. Shown are $Log_2$ odd ratios of all sgRNA constructs as compared to the HAP1 wild-type cells at days 0, 7, and 14. sgRNAs targeting essential genes are marked in yellow, sgRNAs targeting non-essential genes are marked in blue.
Figure 16:
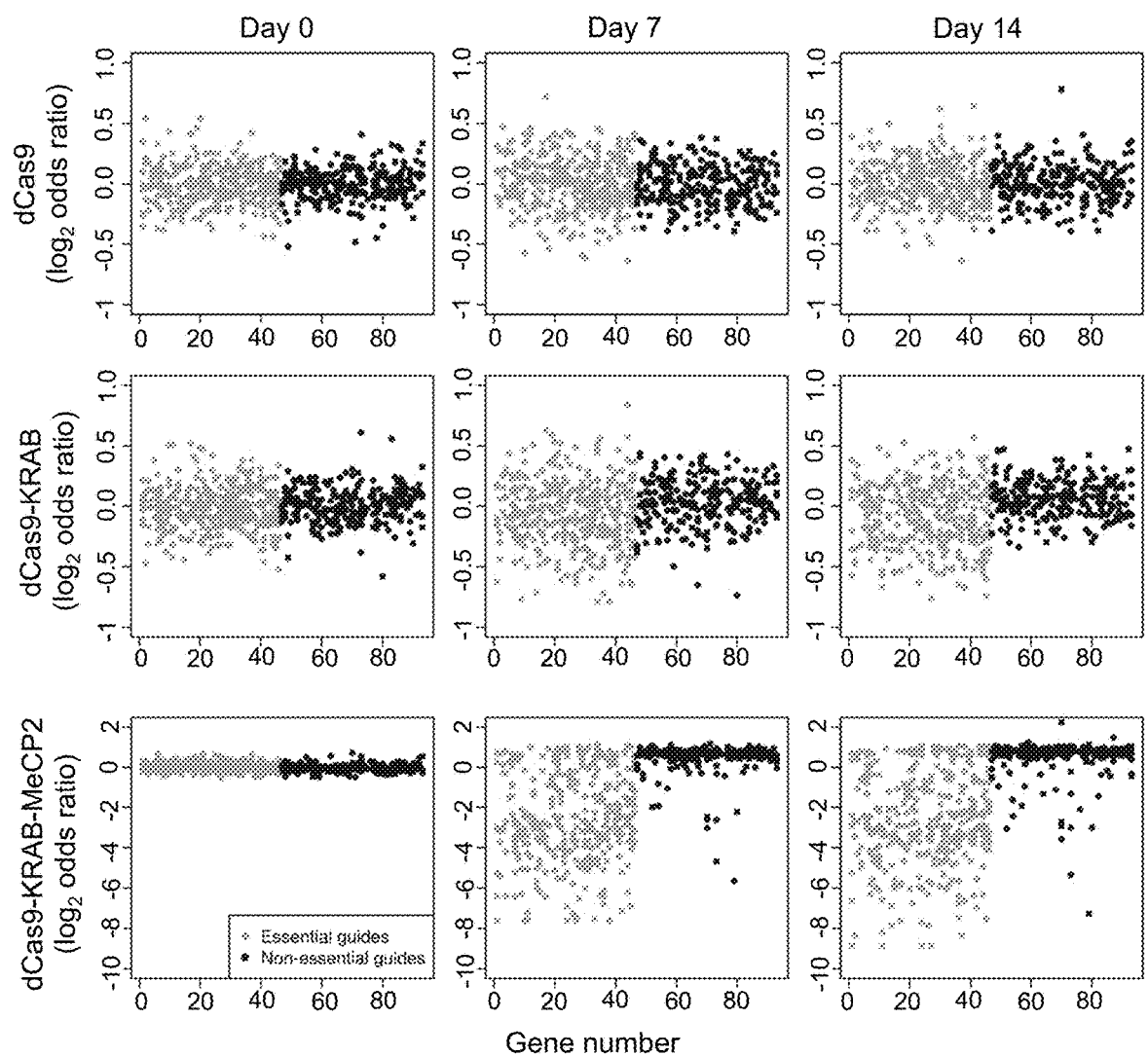
FIG. 16 depicts a repressor screen identifying essential genes in HAP1 cells as shown in FIG. 15. The y-axis scales were adjusted between the different dCas9 constructs to provide a clearer view of the performance of dCas9 and dCas9-KRAB. Using dCas9-KRAB-MeCP2 strong depletion signals of essential gene-targeting sgRNA constructs (up to 256-fold depletion) was detected as early as day 7, compared to the mostly weak signals detected with dCas9-KRAB (up to 2-fold depletion).
Figure 17:
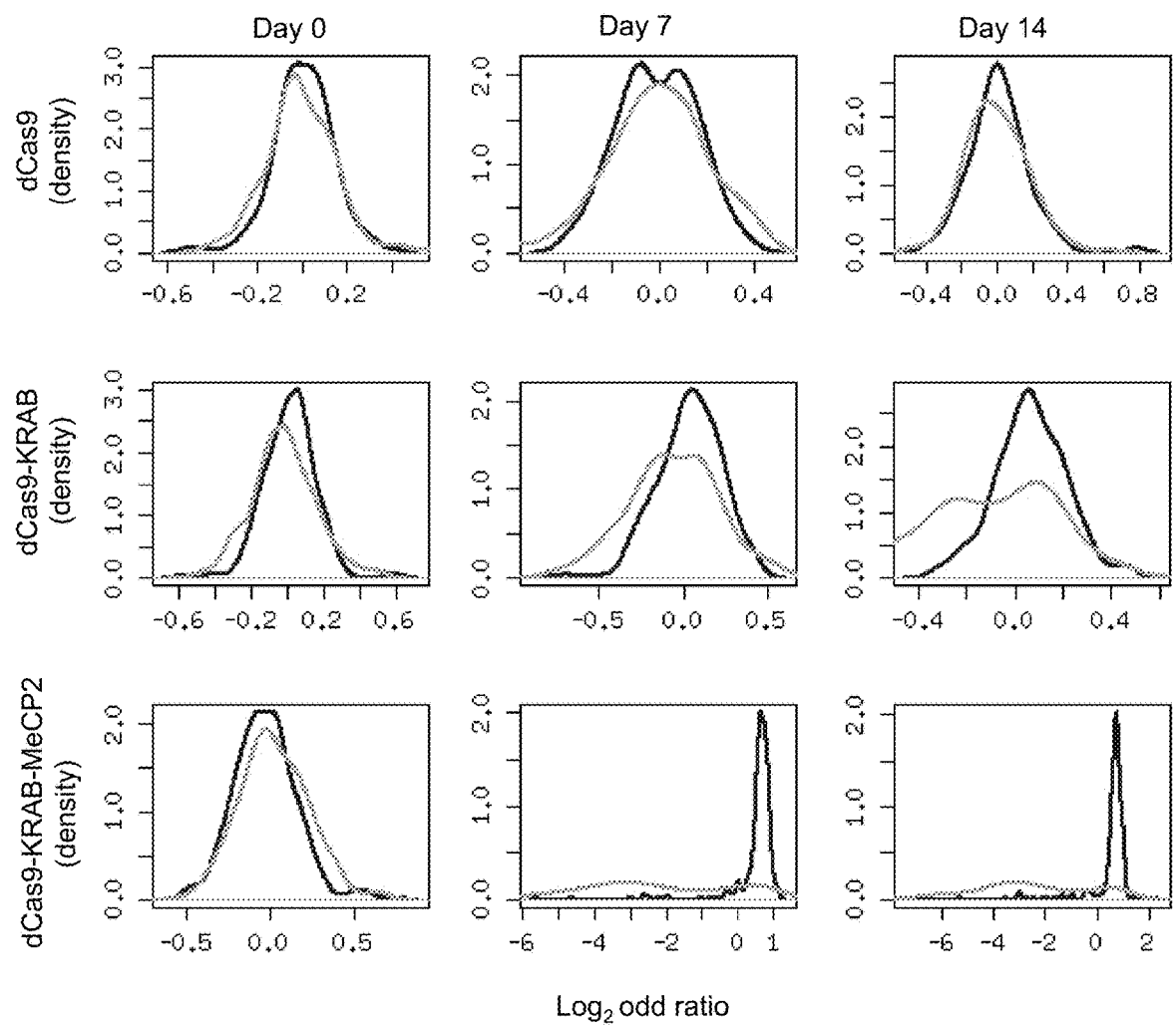
FIG. 17 depicts a histogram of sgRNAs targeting essential genes (yellow) and non-essential genes (blue) in HAP1 lethality screen. At day 7 and day 14-post drug selection, dCas9-KRAB-MeCP2-containing cells showed a greater depletion of sgRNAs targeting essential genes and an overall greater separation between essential and non-essential gene-targeting sgRNAs compared to other dCas9 repressors (p=3.52×10-80 using dCas9-KRAB-MeCP2 vs. 5.41×10-19 using dCas9-KRAB at day 14). Please note x-axis scales vary between different dCas9 constructs to aid in clarity.
Figure 18:
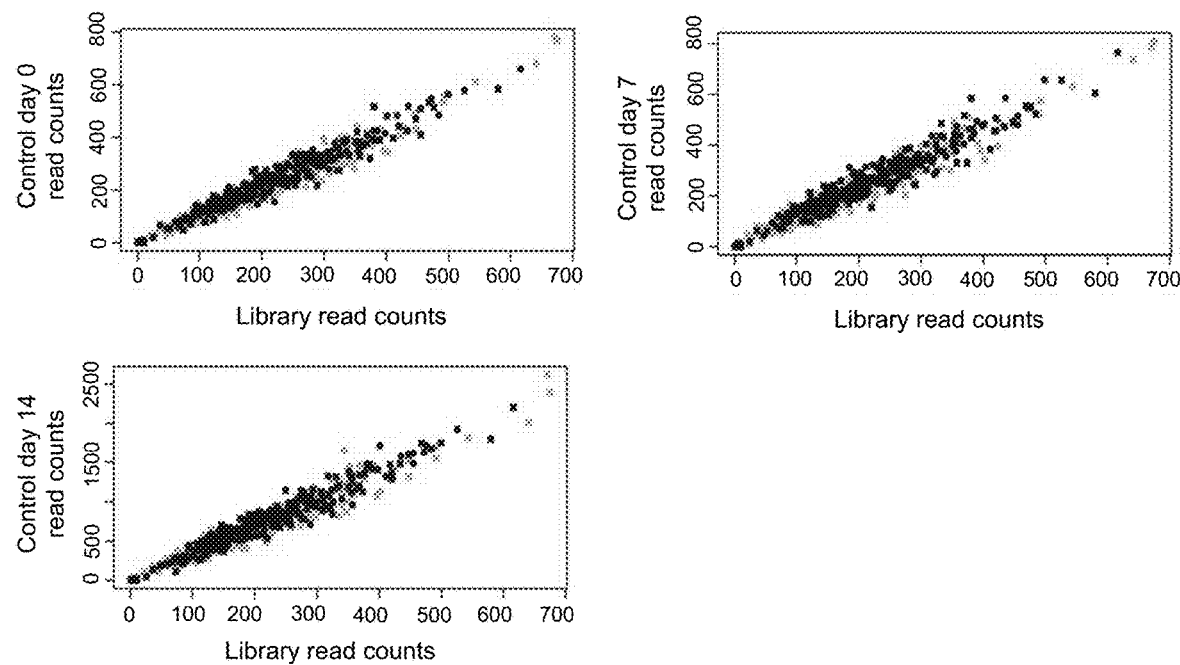
FIG. 18 depicts analyses of sgRNA constructs transduced into HAP1 control samples. Over the course of the experiment the library distribution obtained from HAP1 wild-type cells at day 0, 7, and 14 post-drug selection remained similar to that of the initial DNA library used to generate lentivirus. In the plots, sgRNA read counts in control samples were plotted on y-axis against sgRNA read counts in the library plasmids on x-axis. Blue squares represent non-essential gene-targeting constructs and orange squares represent essential gene-targeting construct.

Genes that are essential for cellular function serve as a useful set of targets for comparing the relative performance of different screening platforms (Evers B, Jastrzebski K, Heijmans J P, _Grernrum W, Beijersbergen R L, Bernards R, "CRISPR knockout screening outperforms shRNA and CRISPRi in identifying essential genes," Nature Biotechnology, 25 Apr. 2016, 34(6):631-633). Consequently, each of our dCas9-expressing lines were infected, as well as wild-type HAP1 cells, with a lentiviral sgRNA library targeting an assortment of essential and non-essential genes. The cells were then passaged over a period of 14 days and quantified the extent to which the various sgRNAs were depleted over time. Cells expressing dCas9-KRAB and dCas9-KRAB-MeCP2 (but not cells expressing dCas9) showed the expected levels of depletion for guides targeting essential genes (Table 3). In the screen using dCas9-KRAB-MeCP2, it was found that all of the targeted essential genes have at least one functional guide showing significant depletion at day 14, in sharp contrast to the screen using dCas9-KRAB for which 16 of the 46 essential genes do not have a guide that significantly deplete over time. In addition, the dCas9-KRAB-MeCP2-containing line yielded a much stronger relative separation between essential and non-essential genes compared to dCas9-KRAB ($p=3.52 \times 10^{-80}$ using dCas9-KRAB-MeCP2 vs. $5.41 \times 10^{-19}$ using dCas9-KRAB at day 14) (FIGS. 15-17, and Table 3). Furthermore, using the more potent repressor, strong depletion signals (up to 256-fold depletion) as early as day 7 were detected, compared to the mostly weak signals that were detected with dCas9-KRAB (up to 2-fold depletion). No decrease in sgRNAs targeting essential genes was observed for wild-type HAP1 cells at any of the study time points, indicating that our results were not a result of bottlenecks during passaging or other technical artifacts (FIG. 18).

Figure 19:
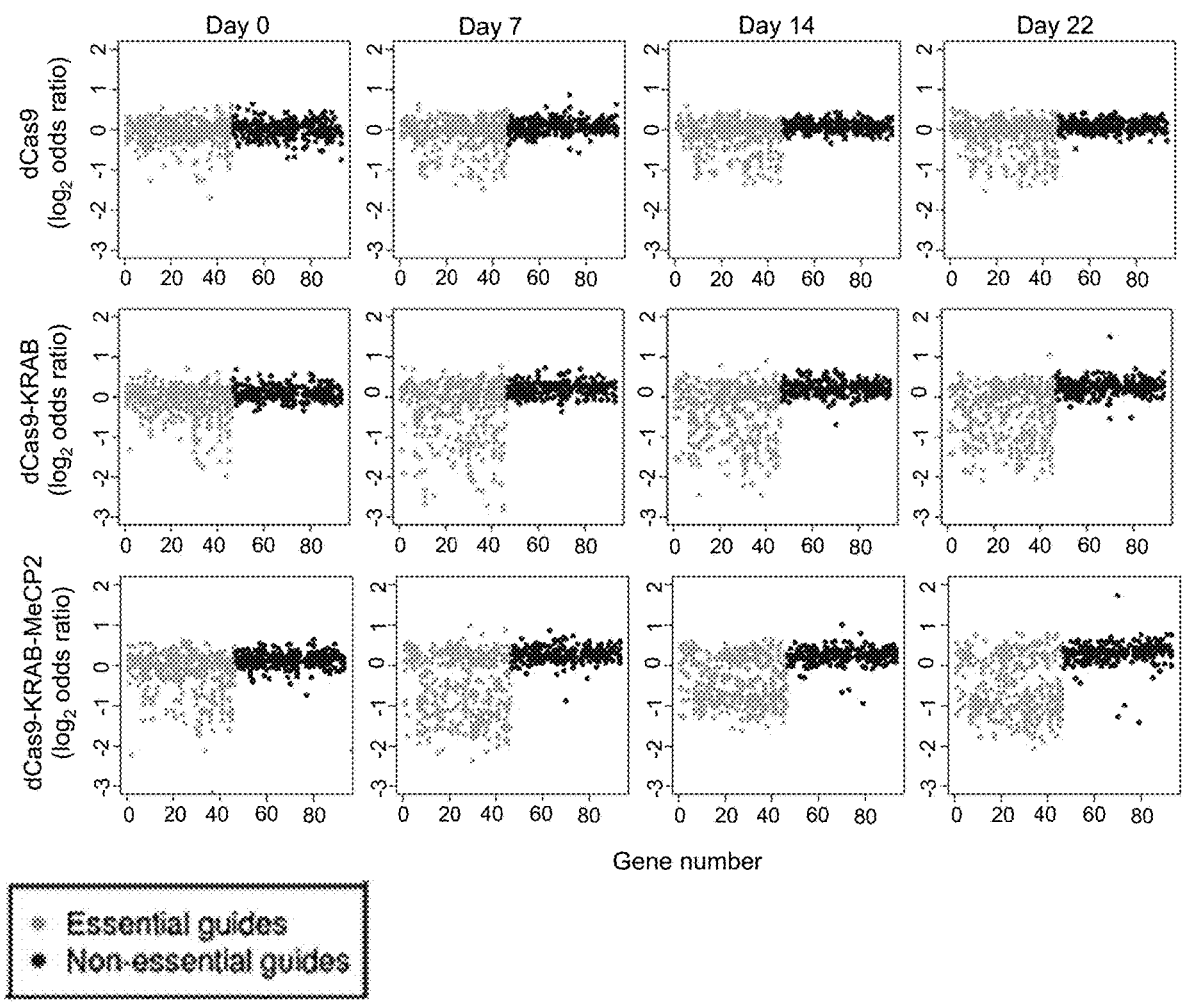
FIG. 19 depicts a repressor screen identifying essential genes in SH-SY5Y cells. SH-SY5Y stably expressing dCas9 repressors were infected with the lentiviral sgRNA library and treated with puromycin at 3 day after infection. Cells were collected for DNA extraction immediately after drug selection (day 0), day 7, day 14, and day 22 for sequencing analyses. Shown are $Log_2$ odd ratios of all sgRNA constructs as compared to the SH-SY5Y wild-type cells at days 0, 7, 14, and 22. While all three repressor-containing cell lines showed the expected depletion of sgRNAs targeting essential genes, dCas9-KRAB-MeCP2 consistently achieved stronger relative separation between essential and non-essential genes at all time points (i.e., at day 22, p=3.08×$10^{-70}$ using dCas9-KRAB-MeCP2 vs. 2.24×$10^{-52}$ using dCas9-KRAB and 1.31×$10^{-23}$ using dCas9, see Table 4 for all statistical comparisons). sgRNAs targeting essential genes are marked in yellow and sgRNAs targeting non-essential genes are marked in blue.
Figure 20:
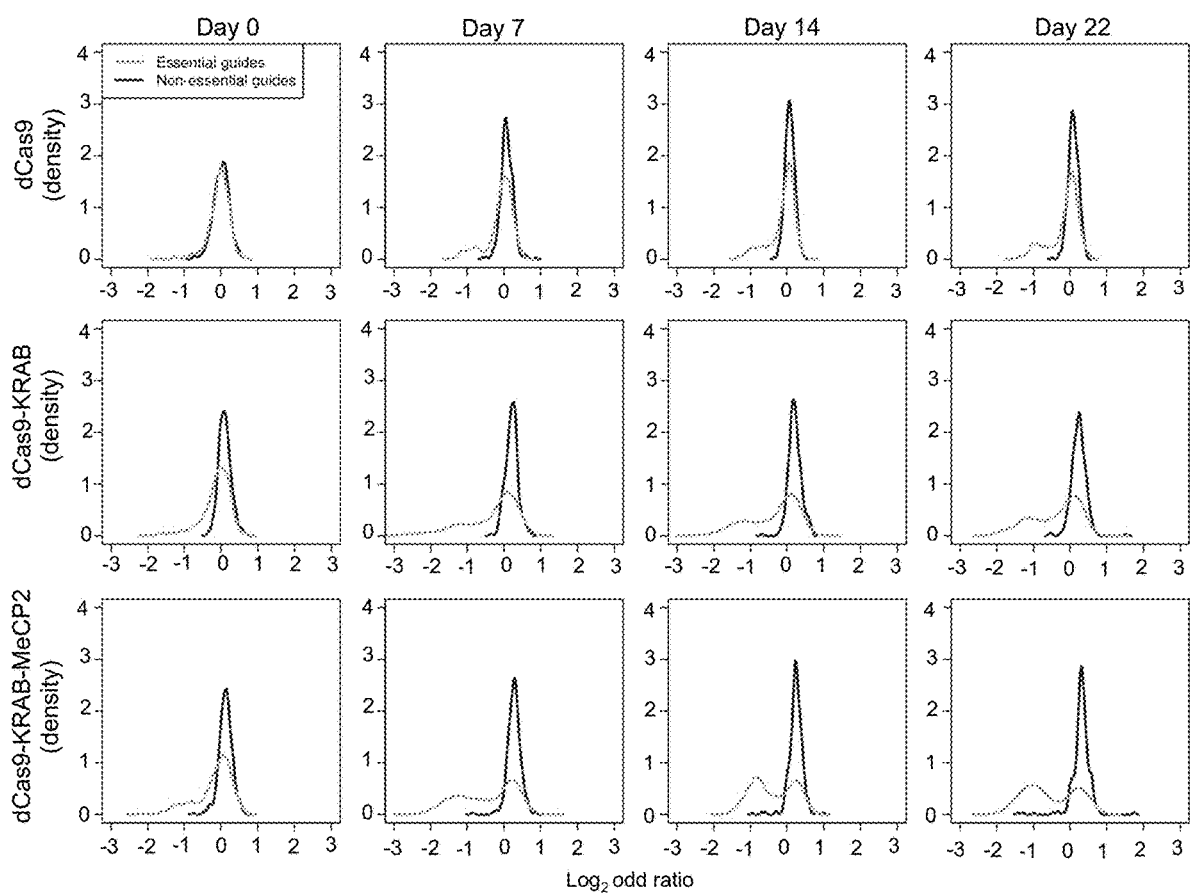
FIG. 20 depicts a histogram of sgRNAs targeting essential genes (yellow) and non-essential genes (blue) in SH-SY5Y lethality screen. While the overall depletion signal was not as strong as that observed in HAP1 cells, dCas9-KRAB-MeCP2-containing SH-SY5Y cells overall showed greater levels of depletion for sgRNAs targeting essential genes than the previous repressors. A greater depletion was observed with dCas9-KRAB-MeCP2 as early as day 7 and this effect remains consistent throughout the rest of the study time points.
Figure 21:
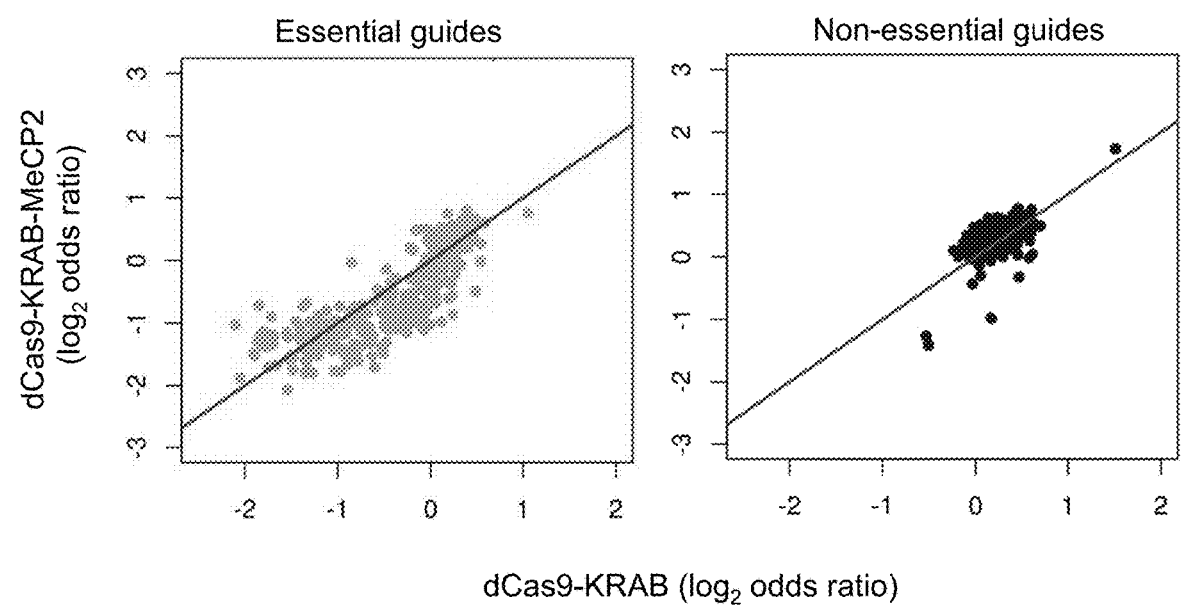
FIG. 21 depicts a comparison of the $Log_2$ odd ratio between dCas9-KRAB-MeCP2 and dCas9-KRAB at 22 day-post drug selection. In the screen using dCas9-KRAB-MeCP2, a greater portion of essential gene-targeting sgRNA constructs showed negative log 2 odds ratio indicating depletion as compared to that observed with dCas9-KRAB.

To test the generality of the system, the above screen was repeated in SH-SY5Y cells, a near-diploid human neuroblastoma cell line. While the overall depletion signal was not as strong as that observed in HAP1 cells, SH-SY5Y containing dCas9-KRAB-MeCP2 showed a greater degree of depletion for sgRNAs targeting essential genes at all times of measurement compared to previous technologies (FIGS. 19-21 and Table 4).

Example V

Methods

Repressor and gRNA Plasmid Construction

Repressor domains were cloned into the same dCas9 plasmid backbone (Addgene #47316) using a combination of Gibson and/or Golden Gate assembly methods. For bipartite and tripartite repressors, a glycine-serine-rich linker was placed in between the different domains. All sgRNAs for endogenous gene repression were selected to bind within −50 to +200 bp around the gene TSS, unless the position was specified otherwise. To generate sgRNA expression plasmids, oligonucleotides containing sgRNA sequence were cloned into a pSB700 vector (Addgene #64046) or variants with different selection markers downstream of a U6 promoter using Golden Gate assembly methods.

Cell Culture and Transfections

HEK293T cells (gift from P. Mali, University of California, Dan Diego) were maintained in Dulbecco's Modified Eagle's Medium (DMEM) (Life Technologies) with 10% heat-inactivated fetal bovine serum (PBS) (Life Technologies) and penicillin-streptomycin (Life Technologies) as previously described (Chavez A, Tuttle M, Pruitt B W, Ewen-Campen B, Chari R, Ter-Ovanesyan D, Haque S J, Cecchi R J, Kowal E J K, Buchthal J, Housden B E, Perrimon N, Collins J J, Church G, "Comparison of Cas9 activators in multiple species," Nat Methods. 2016 July; 13(7):563-567, Epub 2016 May 23). Approximately 50,000 cells were seeded per well in 24-well plates and next day transfected using lipofectamine 2000 (Life Technologies) as previously described (Chavez A, Tuttle M, Pruitt B W, Ewen-Campen B, Chari R, Ter-Ovanesyan D, Haque S J, Cecchi R J, Kowal E J K, Buchthal J, Housden B E, Perrimon N, Collins J J, Church G, "Comparison of Cas9 activators in multiple species," Nat Methods. 2016 July; 13(7):563-567, Epub 2016 May 23). 200 ng of dCas9 repressors, 50 ng of sgRNA, and 60 ng of EYFP reporter along with 50 ng of Gal4-VP1.6 (reporter assay only) were delivered to each well of cells. 50 ng of puromycin-resistant plasmids (endogenous gene study) or 25 ng EBFP-expressing plasmids (reporter assay) were co-transfected to select for transfected cells. 10 ng of each sgRNA per gene were used during multiplex repression. For endogenous gene study, cells were treated with 3 ug/ml of puromycin at 24 h post transfection to enrich for transfected cells. 48 or 72 h after transfection cells were collected to assay by flow cytometry or lysed for RNA purification, for reporter and endogenous experiments, respectively. Cells were tested every 3 months for mycoplasma contamination and consistently tested negative.

Flow Cytometry for Reporter Assays

Reporter assays were performed by targeting dCas9 fusion proteins to a Gal4-VP16 regulated EYFP reporter gene. The reporter plasmid contains an sgRNA-binding sequence (tacctcatcaggaacatgt) followed by a PAM (tgg) (SEQ ID NO: 1). HEK293T cells were transfected with the reporter, Gal4-VP16 activator, sgRNA, and the indicated dCas9 fusion proteins along with an EBFP-expressing plasmid to aide in analyzing only cells that were transfected. Cells were assayed using flow cytometry 48 h after transfection. Analysis was performed on cells expressing >$10^3$ arbitrary units of EBFP2 and the median of EYFP intensity within the gated population was quantified using FlowJo.

Quantitative Real-Time Polymerase Chain Reaction (qPCR) to Analyze Endogenous Gene Expression Total RNA was extracted using RNAeasy Plus mini kit (Qiagen). 500 ng of RNA was used to make cDNA using qScript cDNA synthesis kit (Quanta Bio). KAPA SYBR Fast universal 2× quantitative PCR master mix (KAPA Biosystems) with 0.5 ul of cDNA and 0.4 ul of each forward and reverse primers at 10 uM were used for qPCR, with cycling conditions: 95° C. for 3 min, and 40 cycles of 95° C. for 10 sec, 55° C. for 20 sec, and 72° C. for 30 sec. RNA expression was normalized to the housekeeping gene ACTB and relative gene expression was calculated using $2^{-\Delta\Delta CT}$ method (Livak K J, Schmittgen T D, "Analysis of relative gene expression data using real-time quantitative PCR and the 2(−Delta Delta C(T)) Method," Methods. 2001 December; 25(4):402-8).

Statistical Analysis

For reporter and qPCR studies, statistical comparison was performed using one-tailed t-tests. All sample numbers listed indicate the number of independent biological replicates (wells transfected) in each experiment. Statistical analyses for RNA-seq and repressor guide library screening are described in separate sections below.

Whole Transcriptome RNA Sequencing (RNA-Seq) for Analyzing Repressor Specificity For each sample, total RNA was extracted using RNeasy mini kit (Qiagen) and treated with on-column RNase-free DNase I (Qiagen) following manufacturer's instructions. 1 ug of RNA from each sample was used for library preparation. RNA-seq libraries were constructed using TruSeq Stranded Total RNA Library Prep Kit with Ribo-Zero Gold (Illumina) designed for cytoplasmic and mitochondrial rRNA depletion. All coding RNA and certain forms of noncoding RNA were isolated using bead-based rRNA depletion, followed by cDNA synthesis, and PCR amplification as per manufacturer's protocol. Final libraries were analyzed on TapeStation, quantified with qPCR, pooled together, and run on one lane of an Illumina HiSeq 2500 using 2×100-bp paired-end reads. The Illumina paired-end adapter sequences were removed from the raw reads using Cutadapt v1.8.1. The TruSeq adaptor sequence 5'-AGATCGGAAGAGCACACGTCTGAACTCCAGTCAC-3' (SEQ ID NO: 2) was used for read 1, and its reverse complement, 3'-AGATCGGAAGAGCGTCGTGTAGGGAAAGAGTGTAGATCTCGGTGGTCGCCGTAT CATT-5' (SEQ ID NO: 3) was used for read 2.

Next, RNA libraries were processed using a pipeline which includes STAR-HtSeq-EdgeR for alignment, count generation, and gene expression. Briefly, STAR aligner (v. 2.4.0j) was used to map the reads to hg19, and HtSeq was used to generate gene expression counts. For gene expression and differential expression (DE) analyses, edgeR, limma, and custom R scripts were used to filter out very lowly expressed genes (with a cutoff of 1 count in at least 2 samples), calculate normalization factors, and compute effective library sizes using Trimmed Mean of M Values (TMM) normalization. Gene count is then reported in counts per million (CPM) and correlations are calculated on log 2-transformed data. Finally, to determine the most biologically significant differentially expressed genes, relative gene expression was performed by fold-change thresholding (of log 2(1.5)) and ranking by p-value (FIGS. 11A-11B and FIGS. 12A-12D and Table 2, which describe the strategy used to identify and analyze genes with differential expression (DE) in the RNA-seq experiments details in DE analysis). A small set of genes in addition to the target gene CXCR4 showed small decreases (<log 2(1.5)) in their transcript expression. These genes were further analyzed to assess whether the observed DE was caused by non-specific binding of our sgRNA. Genomic sequences of 2 kb upstream and downstream from TSS of those genes were examined by searching for the presence of a full-length sgRNA binding site (up to 4 mismatches for near matches) as well as seed region of the sgRNA (8 bp in proximal to PAM).

To analyze raw reads from RNA-sequencing experiments and profile whole transcriptome activity induced by dCas9, dCas9-KRAB and dCAS9-KRAB-MeCP2 repressors, edgeR quasi-likelihood (edgeR-quasi) pipeline was implemented for DE. EdgeR-quasi uses negative binomial generalized linear model (McCarthy, D. J., Y. Chen, and G. K. Smyth. 2012. "Differential Expression Analysis of Multifactor RNA-Seq Experiments with Respect to Biological Variation." Nucleic Acids Research 40 (10): 4288-97) with F-tests (Lund, S. P., D. Nettleton, D. J. McCarthy, and G. K. Smyth. 2012. "Detecting Differential Expression in RNA-Sequence Data Using Quasi-Likelihood with Shrunken Dispersion Estimates." Statistical Applications in Genetics and Molecular Biology 11 (5): Article 8), and holds advantages over other methods as it provides speed and reliable error rate control. For the DE analyses, we utilize edgeR-quasi and limma-voom pipelines for two independent biological replicates of dCas9, dCas9-KRAB and dCAS9-KRAB-MeCP2 repressors. The sample size of n=2 in each repressor group is reasonable due to the low biological variability characteristic of cell culture experiments. The analysis involves importing of raw counts, filtering of lowly expressed counts, normalization due to library size bias, DE, and clustering testing.

Figure 12A:
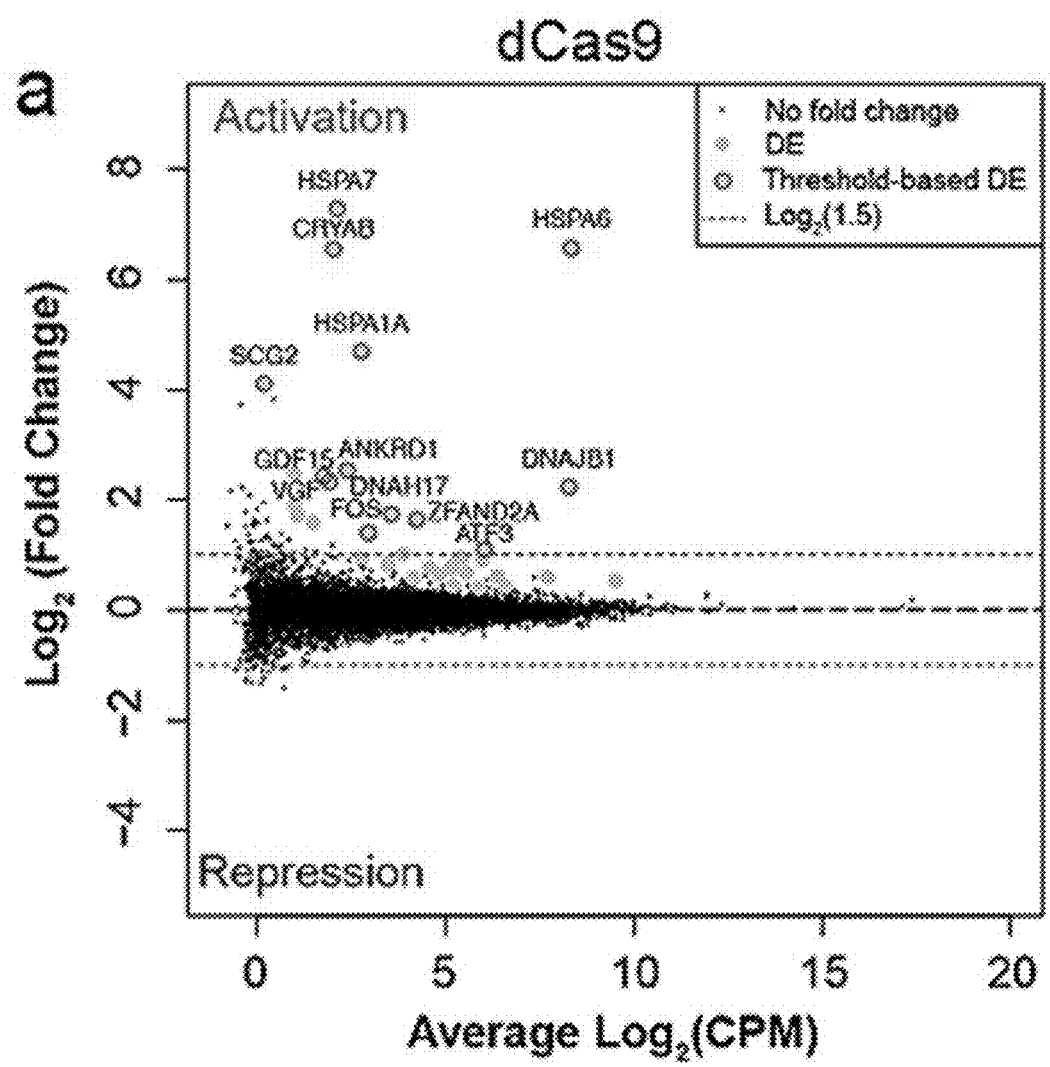
Figure 12B:
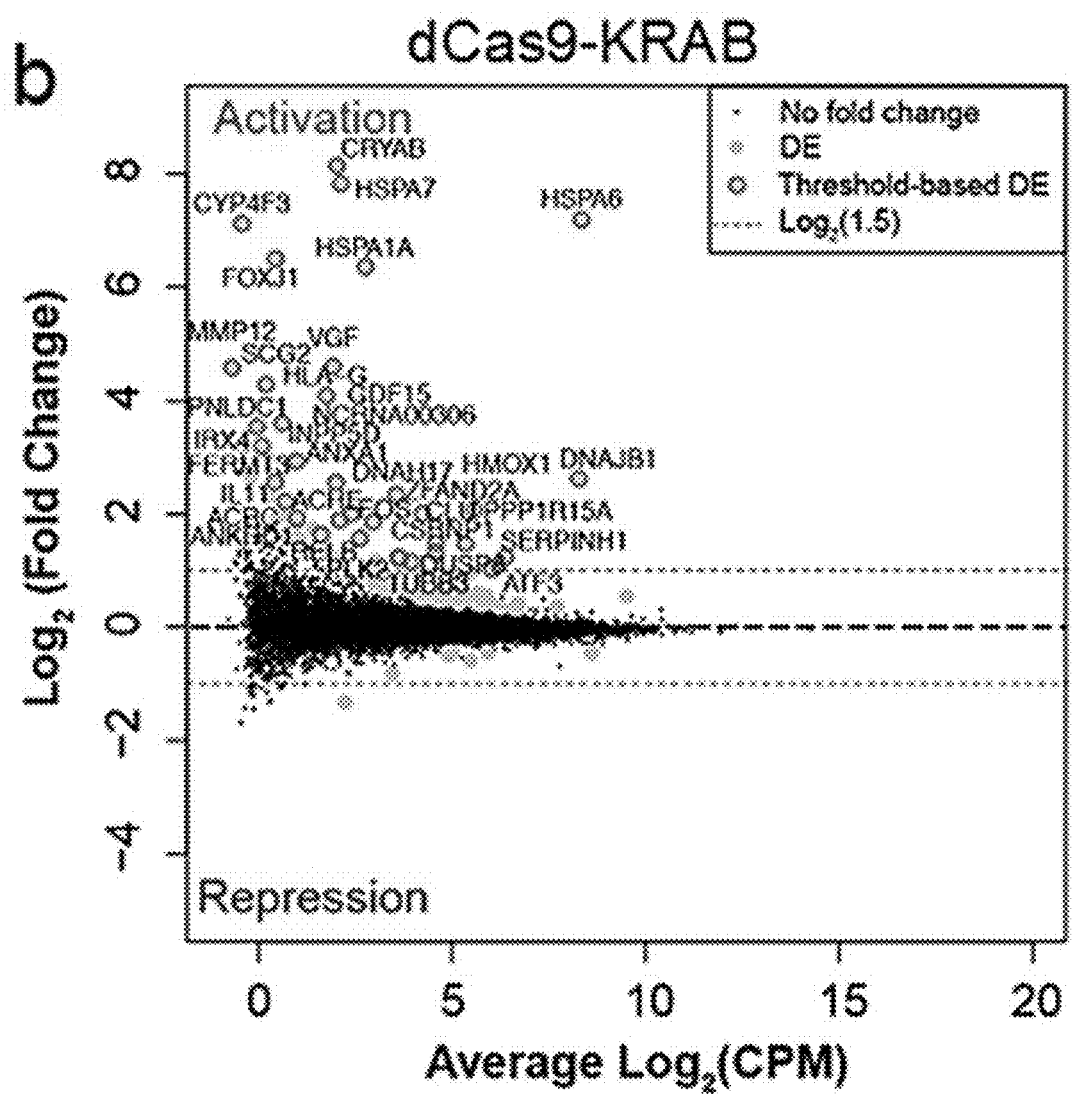
Figure 12C:
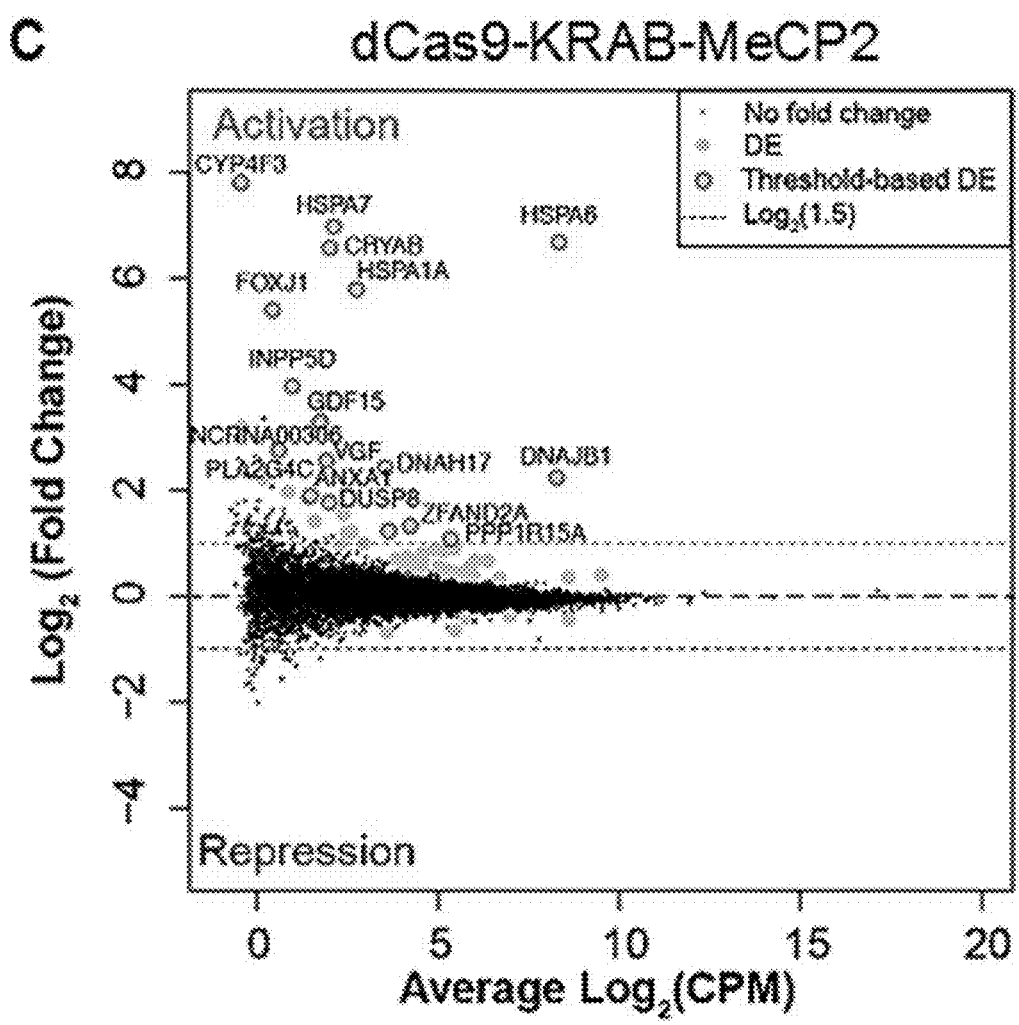

First, DE was tested between each repressor group relative to a control group (delivered sgRNA only) using the edgeR QL functions set to robust=TRUE in glmQLFit to reduce the number of false positives from genes with extreme dispersions (very low and very high). In FIGS. 12A-12C, these results were plotted on two axes—log fold change, $Log_2(FC)$ versus averaged values for log counts per million, $Log_2(CPM)$ where positive $Log_2(FC)$ indicates upregulated genes while negative $Log_2(FC)$ represent downregulated genes relative to the control sample. DE genes at FDR of 5% and corrected using Benjamini-Hochberg method are shown in grey, whereas genes with no significant fold change are shown in black. glmQLFTest function identifies all DE only based on statistical significance including genes with small fold changes. To remove such bias, the TREAT method was applied (McCarthy, D. J., and G. K. Smyth. 2009. "Testing Significance Relative to a Fold-Change Threshold Is a TREAT." Bioinformatics 25 (6): 765-71) which leverages a negative binomial framework using the edgeR's glmTreat function, and simultaneously tests for significance and differential fold change at a cutoff of $Log_2(1.5)$. This method is more stringent as it requires larger p-values for calling genes and leads to fewer detected genes. It therefore provides better specificity in recognizing genes with true biological function. The resulting genes are plotted in red on FIGS. 12A-12C and summarized in the table on FIG. 12D. All genes with DE were listed in Table 2. It is noted that all of these genes have positive $Log_2(FC)$ and correspond to activation in transcriptional activity.

Figure 13A:
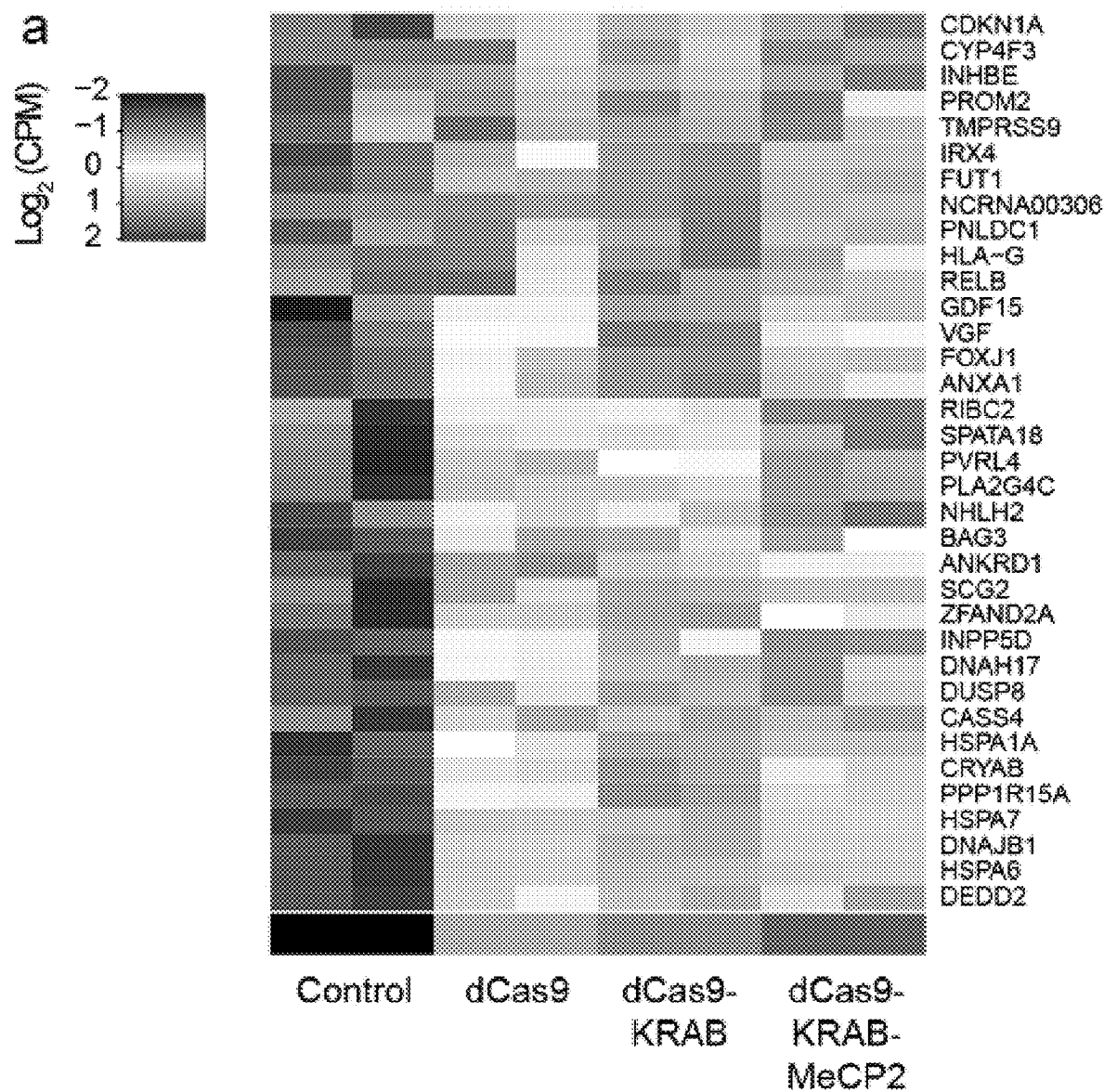
FIGS. 13A-13C depict cluster analysis for control, dCas9, dCas9-KRAB and dCAS9-KRAB-MeCP2 groups.

Expression patterns of transcriptional changes were displayed by plotting the top 35 genes with DE in the control, dCas9, dCas9-KRAB and dCas9-KRAB-MeCP2 groups. Clustering of genes with correlated expression provides insights into biological effects of repressor activity. To display relative changes in genes across the four groups, scaling was performed such that each gene has a mean of zero and standard deviation of 1. The displayed gene clusters are based on Euclidean distance, $(1-R)^2/2$ between each gene pair where R is the Pearson's correlation of the two genes. A scale bar key of normalized $Log_2(CPM)$ represent large negative (colored blue) and positive (colored red) correlations, respectively, where genes with large positive correlations correspond to small Euclidean distances and cluster together (FIG. 13A).

Figure 13B:
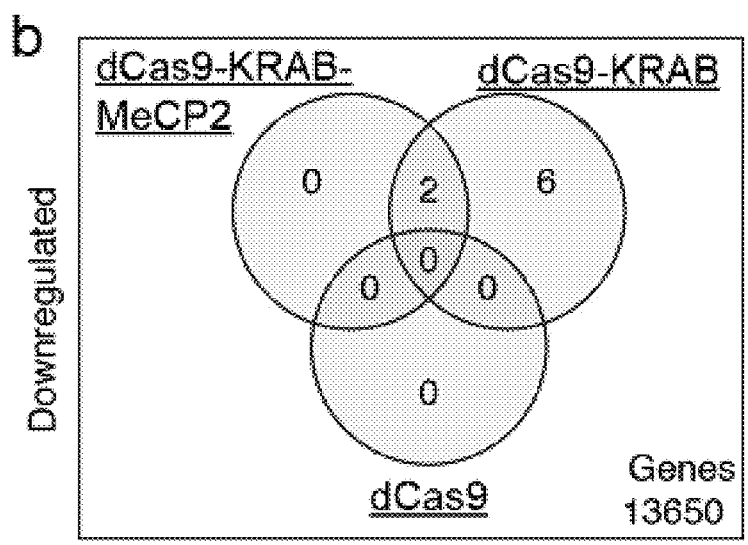
Figure 13C:
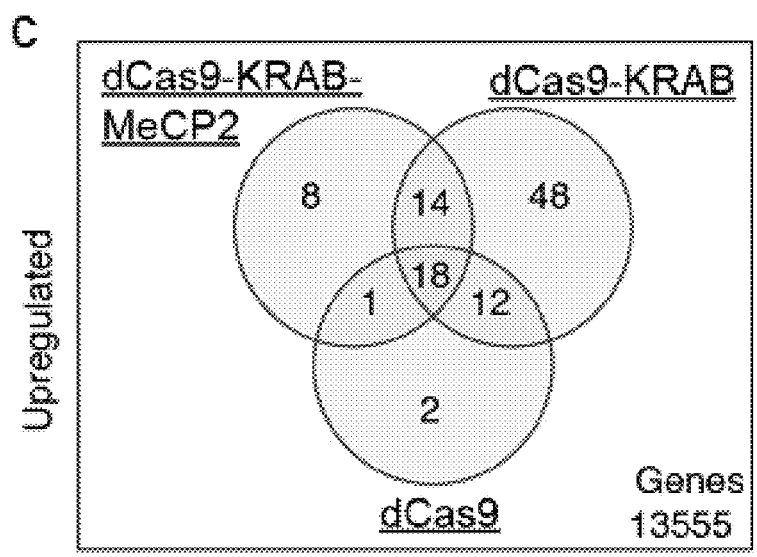

Lastly, activated and repressed genes were examined across all three repressor groups (all normalized to the control group) by applying the limma-voom workflow. Linear modelling was performed in limma, and used lmFit and contrasts.fit functions followed by empirical Bayes model, eBayes. This workflow removes variance-associated dependencies on the mean. In FIGS. 13B-13C, genes were plotted on Venn diagrams for downregulation and upregulation where we define significance at 5% p-value with no log fold change cutoff as a less stringent method for examining transcriptome-wide transcriptional offsets for the different repressors. Furthermore, application of log fold change cutoff of $Log_2(1.5)$ results in no downregulated genes, and significantly reduces the number of upregulated genes. Based on these results, dCas9-KRAB repressor shows the largest clusters of activated genes followed by dCas9-KRAB-MeCP2, and dCas9.

Cell Culture and Generation Repressor-Expressing Stable Cell Lines

HAP1 cells (Horizon Discovery) were maintained in Iscove's Modified Dulbecco's Medium (IMDM) with 10% FBS (Life Technologies) and penicillin-streptomycin (Life Technologies) following manufacturer's instructions. SH-SY5Y (ATCC) was maintained in 1:1 mixture of Eagle's Minimum Essential Medium (EMEM) and F12 Medium (ATCC) with 10% FBS and penicillin-streptomycin following manufacturer's instructions. To generate stable dCas9 repressor expressing cell lines, approximately 30,000-50,000 cells were transfected in 24-well plates with 400 ng of dCas9 repressor-containing PiggBae expression plasmids and 100 ng of transposase vector using lipofectamine 3000 (Life Technologies) as previously described (Chavez A, Tuttle M, Pruitt B W, Ewen-Campen B, Chari R, Ter-Ovanesyan D, Haque S J, Cecchi R J, Kowal E J K, Buchthal J, Housden B E, Perrimon N, Collins J J, Church G, "Comparison of Cas9 activators in multiple species," Nat Methods. 2016 July; 13(7):563-567, Epub 2016 May 23). Media was changed after 2.4 h. Cells were allowed to recover for 2 d and then treated with 5 µg/ml blasticidin. Cells were passaged regularly in drug media for more than 2 weeks to select for heterogeneous populations of dCas9 repressor integrant-containing cells.

Production of single gene-targeting sgRNA lentivirus and cell transduction

HEK293T cells were seeded at 200,000 cells per well in 6-well plates a day prior to transfection. Cells were transfected with 450 ng of pSB700 sgRNA expression plasmid (with puromycin-resistant marker), 600 ng of psPAX2 (Addgene, #12260), and 150 ng of pCMV-VSV-G (Addgene, #8454) using lipofectamine 2000 (Life Technologies). Viral supernatants were collected at 72 h after transfection by centrifuging the medium at 400 g for 5 min to remove cell debris. HAP1 and SH-SY5Y repressor stable cell lines were seeded at ~15,000 and 35,000 cells, respectively, per well in 24-well plates. The following day each sample was infected with 100 µl of sgRNA-containing lentiviruses. Cells were treated with 0.5 µg/ml (HAP1) or 2.5 µg/ml (SH-SY5Y) of puromycin to select for transductants at 48 h after transduction. Cells stably expressing sgRNA were passaged for 2 weeks and collected for RNA extraction and qPCR analysis.

Production of Lentiviral Guide RNA (gRNA) Libraries

The plasmid containing single guide RNA library targeting essential genes was a gift from Dr. Rene Bernards (Evers B, Jastrzebski K, Heijmans J P, Grernrum W, Beijersbergen R L, Bernards R, "CRISPR knockout screening outperforms shRNA and CRISPRi in identifying essential genes," Nat Biotechnol. 2016 June; 34(6):631-3, Epub 2016 Apr. 25). To produce lentiviruses expressing each gRNA library, approximately 1 million of HEK293T cells were plated on a 10 cm dish. The following day cells were transfected with each of the gRNA library plasmids mixed with psPAX2 and pCMV-VSV-G at 4:3:2 ratio using a total of 7-8 µg of DNA using the following protocol. Total plasmid DNA was diluted in 1 ml of serum-free media. Polyethylenimine or PEI (Polysciences) was added to the diluted DNA based on 3:1 ratio of PEI (µg):total DNA (µg). Mixtures were incubated for 15 min at room temperature and then added on the cells. Viral supernatants were collected at 72 h and concentrated using PEG Virus Precipitation Kit (BioVision) according to manufacturer's instructions.

CRISPR Repressor Screens

To compare the ability of different repressors in screening, a series of stable cell lines each containing a unique repressor along with a control cell line without a repressor integrated into the genome were seeded in 6 well plates and allowed to grow to 30-50% confluency to prepare for transduction the following day. Lentiviruses expressing each guide RNA library were produced and used to infect experimental cells so the multiplicity of infection (MOI) was <0.5. Cells were treated with 0.5 ug/ml (HAP1) or 2.5 ug/ml (SH-SY5Y) of puromycin at 48 h (HAP1) or 72 h (SY-SH5Y) post virus transduction. After drug selection, 50% of the cells were collected immediately for DNA extraction using Epicentre Quick Extract Solution, and 50% of the cells were seeded into a set of 15 cm dishes for subsequent passaging. Cells were regularly passaged using standard protocols and collected again at 7-, 14-, and 22-day (SH-SY5Y screen only) post drug selection for DNA extraction. The number of cells manipulated were kept sufficiently large such that we maintained a ~500 to 1000-fold coverage of the library at each stage of passaging. For PCR, 25 μg of genomic DNA divided over 25 reactions were amplified using KAPA2G Robust PCR kit (KAPA Biosystems) along with primer set, PCR 1. The products of all first round PCR reactions from the same sample were then pooled. 1 μl of the pooled product was used for a sample indexing in preparation for next generation sequencing using either Illumina Trueseq indexing primers or a modified series of Trueseq compatible Nextera barcoded primers. Methods and bioinformatics analyses that were used to analyze the repressor screens in HAP1 and SH-SY5Y cell lines are described herein.

Alignment of Sequencing Reads to Reference Contig

The sequencing reads were aligned to a reference contig sequence (NNNNNNccttggagaaaagccttgtttNNNNNNNN-NNNNNNNNNNNNNgtttaagagctagaaatagcaa gtttaaataa-ggctagtccgttatcaacttgaaaaagtggcaccgagtcggtgcttttttcta-gacccagctttcttgtacaaaaaaagaa ttcctgcagccccgataaaataaaag (SEQ ID NO: 4)) using the alignment software BWA-MEM (version 0.7.8) (Li, H. Aligning sequence reads, clone sequences and assembly contigs with BWA-MEM. ArXiv13033997 Q-Bio (2013)). Samtools was used (version 1.2) to extract aligned sequences that have a mapping quality score >=30 (Li, H. et al. The Sequence Alignment/Map format and SAMtools. *Bioinforma. Oxf. Engl.* 25, 2078-2079 (2009)). The 20-nucleotide variable sequence was then match to the 20-nucleotide sgRNA library with 683 guide sequences. Sequences that do not match any of the 683 guide sequences were discarded from the analysis.

Analysis of the Repressor sgRNA Library

The sgRNA library was first sequenced to determine the distribution of the guide sequences. A total 129,362 sequences map to a guide sequence within the library of 683 guides. However, 53 of the guides were severely underrepresented, i.e. less than 50 reads mapped to the guide (<0.04%) and they were removed from all further analysis.

Comparing the Guide Sequences for all the Conditions

For all the conditions, the mapped guides were compared against the corresponding control experiment. The control experiment for all the conditions is the experiment performed without any repressor, i.e. without dCas9, dCas9-Krab or dCas9-Krab-Mecp2. For each guide, its frequency for the condition was compared against its frequency for the control. This is done by calculating the odds-ratio (OR) for each guide using the formula, $$OR_i = \frac{\frac{test_i}{testTotal}}{\frac{control_i}{controlTotal}}$$

where $test_i$ is the number of reads that map to guide i for the test condition and $control_i$ is the number of reads that map to guide i for the control while testTotal and controlTotal are the total number of reads for the test condition and control, respectively. If the guide is enriched in the test condition, the OR would be >1 while if the guide is depleted, the OR would be <1.

Determining if the Essential Guides are Depleted

Out of the 630 guides from the library, 370 target essential genes (essential guides) while the remaining 260 target non-essential genes. To determine if the essential guides were significantly depleted, we performed a 1-tailed Welch T-test between the $log_2$ OR of the essential guides versus the $log_2$ OR of the non-essential guides (Tables 3 and 4). Also, for the dCas9-Krab-Mecp2 for Hap1 day 7 and day 14, there were a number of guides that were completely depleted, ie. they had 0 reads for the test condition. This presents a problem as the $log_2$ OR for those guides would be $-\infty$. To allow for the T-test, we replaced the $log_2$ OR for those guides to the minimal finite $log_2$ OR for that condition, which is -7.61 for day 7 and -8.87 for day 14.

Cell Culture

All transfections were performed on HEK293 ft cells using polyethylenemine (PEI). Cells were cultured in Debulcco's Modified Eagle Medium (DMEM), with 10% Fetal Bovine Serum (FBS), non-essential amino acids (NEAA), glutamine, sodium pyruvate, and penicillin/streptomycin. The day prior to transfection, cells were passaged and split into 24-well plates, then allowed to grow to 70-90% confluence. Mixes totaling 600 ng of DNA were used with a 2:1 PEI:DNA ratio to transfect the confluent cells using standard transfection protocols. All conditions were transfected in quadruplicate. Media were changed daily post-transfection until flow cytometry was performed ~72h later.

Data Analysis 72h after transfection, cells were trypsinized, washed with Hank's Balanced Salt Solution (HBSS) with 2% FBS, then resuspended in 200 uL HBSS+FBS. Then flow cytometry was performed using a BD FACSCelesta flow cytometer. 200,000 events were collected, measuring forward scatter (FSC), side scatter (SSC), EBFP expression (BV421), and EYFP expression (BB515). Data were analyzed using FlowJo (FlowJo, LLC). For analysis, all data were compensated using single color and non-transfected controls. Cells were then gated by FSC and SSC to separate healthy, living cells from dead cells and debris. Living cells were further gated by EBFP; laser voltage was set in such a way as to make non-fluorescing cells express at $10^2$ or lower, so the BV421 gate was set at $10^2$.

Cells with above $10^2$ a.u of EBFP expression were considered transfected and were further analyzed by taking the geometric mean of the population's EYFP (BB515) expression. The geometric means of all samples were exported and further analyzed in Excel (Microsoft) or Prism (GraphPad Software).

TABLE 1

Sequences of dCas9-Krab and dCas9-KRAB-MeCP2

>dCas9-KRAB
Labels: {SV40 nucleus localization signal (NLS)}; KRAB; glycine
serine-rich linker (bold); stop codon (italic)
[ATGGACAAGAAGTACTCCATTGGGCTCGCTATCGGCACAAACAGCGTCGGCTGG

GCCGTCATTACGGACGAGTACAAGGTGCCGAGCAAAAAATTCAAAGTTCTGGGCA

ATACCGATCGCCACAGCATAAAGAAGAACCTCATTGGCGCCCTCCTGTTCGACTC

TABLE 1-continued

Sequences of dCas9-Krab and dCas9-KRAB-MeCP2

CGGGGAGACGGCCGAAGCCACGCGGCTCAAAAGAACAGCACGGCGCAGATATAC

CCGCAGAAAGAATCGGATCTGCTACCTGCAGGAGATCTTTAGTAATGAGATGGCT

AAGGTGGATGACTCTTTCTTCCATAGGCTGGAGGAGTCCTTTTTGGTGGAGGAGG

ATAAAAAGCACGAGCGCCACCCAATCTTTGGCAATATCGTGGACGAGGTGGCGTA

CCATGAAAAGTACCCAACCATATATCATCTGAGGAAGAAGCTTGTAGACAGTACT

GATAAGGCTGACTTGCGGTTGATCTATCTCGCGCTGGCGCATATGATCAAATTTCG

GGGACACTTCCTCATCGAGGGGGACCTGAACCCAGACAACAGCGATGTCGAtAAA

CTCTTTATCCAACTGGTTCAGACTTACAATCAGCTTTTCGAAGAGAACCCGATCAA

CGCATCCGGAGTTGACGCCAAAGCAATCCTGAGCGCTAGGCTGTCCAAATCCCGG

CGGCTCGAAAACCTCATCGCACAGCTCCCTGGGGAGAAGAAGAACGGCCTGTTTG

GTAATCTTATCGCCCTGTCACTCGGGCTGACCCCCAACTTTAAATCTAACTTCGAC

CTGGCCGAAGATGCCAAGCTTCAACTGAGCAAAGACACCTACGATGATGATCTCG

ACAATCTGCTGGCCCAGATCGGCGACCAGTACGCAGACCTTTTTTTGGCGGCAAA

GAACCTGTCAGACGCCATTCTGCTGAGTGATATTCTGCGAGTGAACACGGAGATC

ACCAAAGCTCCGCTGAGCGCTAGTATGATCAAGCGCTATGATGAGCACCACCAAG

ACTTGACTTTGCTGAAGGCCCTTGTCAGACAGCAACTGCCTGAGAAGTACAAGGA

AATTTTCTTCGATCAGTCTAAAAATGGCTACGCCGGATACATTGACGGCGGAGCA

AGCCAGGAGGAATTTTACAAATTTATTAAGCCCATCTTGGAAAAAATGGACGGCA

CCGAGGAGCTGCTGGTAAAGCTTAACAGAGAAGATCTGTTGCGCAAACAGCGCAC

TTTCGACAATGGAAGCATCCCCCACCAGATTCACCTGGGCGAACTGCACGCTATC

CTCAGGCGGCAAGAGGATTTCTACCCCTTTTTGAAAGATAACAGGGAAAAGATTG

AGAAAATCCTCACATTTCGGATACCCTACTATGTAGGCCCCCTCGCCCGGGGAAA

TTCCAGATTCGCGTGGATGACTCGCAAATCAGAAGAGACCATCACTCCCTGGAAC

TTCGAGGAAGTCGTGGATAAGGGGGCCTCTGCCCAGTCCTTCATCGAAAGGATGA

CTAACTTTGATAAAAATCTGCCTAACGAAAAGGTGCTTCCTAAACACTCTCTGCTG

TACGAGTACTTCACAGTTTATAACGAGCTCACCAAGGTCAAATACGTCACAGAAG

GGATGAGAAAGCCAGCATTCCTGTCTGGAGAGCAGAAGAAAGCTATCGTGGACCT

CCTCTTCAAGACGAACCGGAAAGTTACCGTGAAACAGCTCAAAGAAGACTATTTC

AAAAAGATTGAATGTTTCGACTCTGTTGAAATCAGCGGAGTGGAGGATCGCTTCA

ACGCATCCCTGGGAACGTATCACGATCTCCTGAAAATCATTAAAGACAAGGACTT

CCTGGACAATGAGGAGAACGAGGACATTCTTGAGGACATTGTCCTCACCCTTACG

TTGTTTGAAGATAGGGAGATGATTGAAGAACGCTTGAAAACTTACGCTCATCTCTT

CGACGACAAAGTCATGAAACAGCTCAAGAGGCGCCGATATACAGGATGGGGGCG

GCTGTCAAGAAAACTGATCAATGGGATCCGAGACAAGCAGAGTGGAAAGACAAT

CCTGGATTTTCTTAAGTCCGATGGATTTGCCAACCGGAACTTCATGCAGTTGATCC

ATGATGACTCTCTCACCTTTAAGGAGGACATCCAGAAAGCACAAGTTTCTGGCCA

GGGGGACAGTCTTCACGAGCACATCGCTAATCTTGCAGGTAGCCCAGCTATCAAA

AAGGGAATACTGCAGACCGTTAAGGTCGTGGATGAACTCGTCAAAGTAATGGGAA

GGCATAAGCCCGAGAATATCGTTATCGAGATGGCCCGAGAGAACCAAACTACCCA

TABLE 1-continued

Sequences of dCas9-Krab and dCas9-KRAB-MeCP2

GAAGGGACAGAAGAACAGTAGGGAAAGGATGAAGAGGATTGAAGAGGGTATAA

AAGAACTGGGGTCCCAAATCCTTAAGGAACACCCAGTTGAAAACACCCAGCTTCA

GAATGAGAAGCTCTACCTGTACTACCTGCAGAACGGCAGGGACATGTACGTGGAT

CAGGAACTGGACATCAATCGGCTCTCCGACTACGACGTGGCTGCTATCGTGCCCC

AGTCTTTTCTCAAAGATGATTCTATTGATAATAAAGTGTTGACAAGATCCGATAAA gcTAGAGGGAAGAGTGATAACGTCCCCTCAGAAGAAGTTGTCAAGAAAATGAAAA

ATTATTGGCGGCAGCTGCTGAACGCCAAACTGATCACACAACGGAAGTTCGATAA

TCTGACTAAGGCTGAACGAGGTGGCCTGTCTGAGTTGGATAAAGCCGGCTTCATC

AAAAGGCAGCTTGTTGAGACACGCCAGATCACCAAGCACGTGGCCCAAATTCTCG

ATTCACGCATGAACACCAAGTACGATGAAAATGACAAACTGATTCGAGAGGTGAA

AGTTATTACTCTGAAGTCTAAGCTGGTCTCAGATTTCAGAAAGGACTTTCAGTTTT

ATAAGGTGAGAGAGATCAACAATTACCACCATGCGCATGATGCCTACCTGAATGC

AGTGGTAGGCACTGCACTTATCAAAAAATATCCCAAGCTTGAATCTGAATTTGTTT

ACGGAGACTATAAAGTGTACGATGTTAGGAAAATGATCGCAAAGTCTGAGCAGG

AAATAGGCAAGGCCACCGCTAAGTACTTCTTTTACAGCAATATTATGAATTTTTTC

AAGACCGAGATTACACTGGCCAATGGAGAGATTCGGAAGCGACCACTTATCGAAA

CAAACGGAGAAACAGGAGAAATCGTGTGGGACAAGGGTAGGGATTTCGCGACAG

TCCGGAAGGTCCTGTCCATGCCGCAGGTGAACATCGTTAAAAAGACCGAAGTACA

GACCGGAGGCTTCTCCAAGGAAAGTATCCTCCCGAAAAGGAACAGCGACAAGCT

GATCGCACGCAAAAAAGATTGGGACCCCAAGAAATACGGCGGATTCGATTCTCCT

ACAGTCGCTTACAGTGTACTGGTTGTGGCCAAAGTGGAGAAAGGGAAGTCTAAAA

AACTCAAAAGCGTCAAGGAACTGCTGGGCATCACAATCATGGAGCGATCAAGCTT

CGAAAAAAACCCCATCGACTTTCTCGAGGCGAAAGGATATAAAGAGGTCAAAAA

AGACCTCATCATTAAGCTTCCCAAGTACTCTCTCTTTGAGCTTGAAAACGGCCGGA

AACGAATGCTCGCTAGTGCGGGCGAGCTGCAGAAAGGTAACGAGCTGGCACTGCC

CTCTAAATACGTTAATTTCTTGTATCTGGCCAGCCACTATGAAAAGCTCAAAGGGT

CTCCCGAAGATAATGAGCAGAAGCAGCTGTTCGTGGAACAACACAAACACTACCT

TGATGAGATCATCGAGCAAATAAGCGAATTCTCCAAAAGAGTGATCCTCGCCGAC

GCTAACCTCGATAAGGTGCTTTCTGCTTACAATAAGCACAGGGATAAGCCCATCA

GGGAGCAGGCAGAAAACATTATCCACTTGTTTACTCTGACCAACTTGGGCGCGCC

TGCAGCCTTCAAGTACTTCGACACCACCATAGACAGAAAGCGGTACACCTCTACA

AAGGAGGTCCTGGACGCCACACTGATTCATCAGTCAATTACGGGGCTCTATGAAA

CAAGAATCGACCTCTCTCAGCTCGGTGGAGACAGCAGGGCTGAC]{CCCAAGAAG

AAGAGGAAGGTG}AGTGGTGGAGGAAGTGGCGGGTCAGGGTCGATGGACGCG

AAATCACTTACGGCATGGTCGAGAACACTGGTTACGTTCAAGGACGTGTTTGTGG

ACTTTACACGTGAGGAGTGGAAATTGCTGGATACTGCGCAACAAATTGTGTATCG

AAATGTCATGCTTGAGAATTACAAGAACCTCGTCAGTCTCGGATACCAGTTGACG

AAACCGGATGTGATCCTTAGGCTCGAAAAGGGGGAAGAACCTTGGCTGGTA*TAG*

TABLE 1-continued

Sequences of dCas9-Krab and dCas9-KRAB-MeCP2

>dCas9-KRAB-MeCP2
Labels: [dCas9]; {SV40 nucleus localization signal (NLS)}; KRAB;
(TRD domain of MeCP2); glycine serine-rich linker (bold); stop
codon (italic)

[ATGGACAAGAAGTACTCCATTGGGCTCGCTATCGGCACAAACAGCGTCGGCTGG

GCCGTCATTACGGACGAGTACAAGGTGCCGAGCAAAAAATTCAAAGTTCTGGGCA

ATACCGATCGCCACAGCATAAAGAAGAACCTCATTGGCGCCCTCCTGTTCGACTC

CGGGGAGACGGCCGAAGCCACGCGGCTCAAAAGAACAGCACGGCGCAGATATAC

CCGCAGAAAGAATCGGATCTGCTACCTGCAGGAGATCTTTAGTAATGAGATGGCT

AAGGTGGATGACTCTTTCTTCCATAGGCTGGAGGAGTCCTTTTTGGTGGAGGAGG

ATAAAAAGCACGAGCGCCACCCAATCTTTGGCAATATCGTGGACGAGGTGGCGTA

CCATGAAAAGTACCCAACCATATATCATCTGAGGAAGAAGCTTGTAGACAGTACT

GATAAGGCTGACTTGCGGTTGATCTATCTCGCGCTGGCGCATATGATCAAATTCG

GGGACACTTCCTCATCGAGGGGGACCTGAACCCAGACAACAGCGATGTCGAtAAA

CTCTTTATCCAACTGGTTCAGACTTACAATCAGCTTTTCGAAGAGAACCCGATCAA

CGCATCCGGAGTTGACGCCAAAGCAATCCTGAGCGCTAGGCTGTCCAAATCCCGG

CGGCTCGAAAACCTCATCGCACAGCTCCCTGGGGAGAAGAAGAACGGCCTGTTTG

GTAATCTTATCGCCCTGTCACTCGGGCTGACCCCCAACTTTAAATCTAACTTCGAC

CTGGCCGAAGATGCCAAGCTTCAACTGAGCAAAGACACCTACGATGATGATCTCG

ACAATCTGCTGGCCCAGATCGGCGACCAGTACGCAGACCTTTTTTTGGCGGCAAA

GAACCTGTCAGACGCCATTCTGCTGAGTGATATTCTGCGAGTGAACACGGAGATC

ACCAAAGCTCCGCTGAGCGCTAGTATGATCAAGCGCTATGATGAGCACCACCAAG

ACTTGACTTTGCTGAAGGCCCTTGTCAGACAGCAACTGCCTGAGAAGTACAAGGA

AATTTTCTTCGATCAGTCTAAAAATGGCTACGCCGGATACATTGACGGCGGAGCA

AGCCAGGAGGAATTTTACAAATTTATTAAGCCCATCTTGGAAAAAATGGACGGCA

CCGAGGAGCTGCTGGTAAAGCTTAACAGAGAAGATCTGTTGCGCAAACAGCGCAC

TTTCGACAATGGAAGCATCCCCCACCAGATTCACCTGGGCGAACTGCACGCTATC

CTCAGGCGGCAAGAGGATTTCTACCCCTTTTTGAAAGATAACAGGGAAAAGATTG

AGAAAATCCTCACATTTCGGATACCCTACTATGTAGGCCCCCTCGCCCGGGGAAA

TTCCAGATTCGCGTGGATGACTCGCAAATCAGAAGAGACCATCACTCCCTGGAAC

TTCGAGGAAGTCGTGGATAAGGGGGCCTCTGCCCAGTCCTTCATCGAAAGGATGA

CTAACTTTGATAAAAATCTGCCTAACGAAAAGGTGCTTCCTAAACACTCTCTGCTG

TACGAGTACTTCACAGTTTATAACGAGCTCACCAAGGTCAAATACGTCACAGAAG

GGATGAGAAAGCCAGCATTCCTGTCTGGAGAGCAGAAGAAAGCTATCGTGGACCT

CCTCTTCAAGACGAACCGGAAAGTTACCGTGAAACAGCTCAAAGAAGACTATTTC

AAAAAGATTGAATGTTTCGACTCTGTTGAAATCAGCGGAGTGGAGGATCGCTTCA

ACGCATCCCTGGGAACGTATCACGATCTCCTGAAAATCATTAAAGACAAGGACTT

CCTGGACAATGAGGAGAACGAGGACATTCTTGAGGACATTGTCCTCACCCTTACG

TTGTTTGAAGATAGGGAGATGATTGAAGAACGCTTGAAAACTTACGCTCATCTCTT

CGACGACAAAGTCATGAAACAGCTCAAGAGGCGCCGATATACAGGATGGGGGCG

GCTGTCAAGAAAACTGATCAATGGGATCCGAGACAAGCAGAGTGGAAAGACAAT

TABLE 1-continued

Sequences of dCas9-Krab and dCas9-KRAB-MeCP2

CCTGGATTTTCTTAAGTCCGATGGATTTGCCAACCGGAACTTCATGCAGTTGATCC

ATGATGACTCTCTCACCTTTAAGGAGGACATCCAGAAAGCACAAGTTTCTGGCCA

GGGGGACAGTCTTCACGAGCACATCGCTAATCTTGCAGGTAGCCCAGCTATCAAA

AAGGGAATACTGCAGACCGTTAAGGTCGTGGATGAACTCGTCAAAGTAATGGGAA

GGCATAAGCCCGAGAATATCGTTATCGAGATGGCCCGAGAGAACCAAACTACCCA

GAAGGGACAGAAGAACAGTAGGGAAAGGATGAAGAGGATTGAAGAGGGTATAA

AAGAACTGGGGTCCCAAATCCTTAAGGAACACCCAGTTGAAAACACCCAGCTTCA

GAATGAGAAGCTCTACCTGTACTACCTGCAGAACGGCAGGGACATGTACGTGGAT

CAGGAACTGGACATCAATCGGCTCTCCGACTACGACGTGGCTGCTATCGTGCCCC

AGTCTTTTCTCAAAGATGATTCTATTGATAATAAAGTGTTGACAAGATCCGATAAA gcTAGAGGGAAGAGTGATAACGTCCCCTCAGAAGAAGTTGTCAAGAAAATGAAAA

ATTATTGGCGGCAGCTGCTGAACGCCAAACTGATCACACAACGGAAGTTCGATAA

TCTGACTAAGGCTGAACGAGGTGGCCTGTCTGAGTTGGATAAAGCCGGCTTCATC

AAAAGGCAGCTTGTTGAGACACGCCAGATCACCAAGCACGTGGCCCAAATTCTCG

ATTCACGCATGAACACCAAGTACGATGAAAATGACAAACTGATTCGAGAGGTGAA

AGTTATTACTCTGAAGTCTAAGCTGGTCTCAGATTTCAGAAAGGACTTTCAGTTTT

ATAAGGTGAGAGAGATCAACAATTACCACCATGCGCATGATGCCTACCTGAATGC

AGTGGTAGGCACTGCACTTATCAAAAAATATCCCAAGCTTGAATCTGAATTTGTTT

ACGGAGACTATAAAGTGTACGATGTTAGGAAAATGATCGCAAAGTCTGAGCAGG

AAATAGGCAAGGCCACCGCTAAGTACTTCTTTTACAGCAATATTATGAATTTTTTC

AAGACCGAGATTACACTGGCCAATGGAGAGATTCGGAAGCGACCACTTATCGAAA

CAAACGGAGAAACAGGAGAAATCGTGTGGGACAAGGGTAGGGATTTCGCGACAG

TCCGGAAGGTCCTGTCCATGCCGCAGGTGAACATCGTTAAAAAGACCGAAGTACA

GACCGGAGGCTTCTCCAAGGAAAGTATCCTCCCGAAAAGGAACAGCGACAAGCT

GATCGCACGCAAAAAAGATTGGGACCCCAAGAAATACGGCGGATTCGATTCTCCT

ACAGTCGCTTACAGTGTACTGGTTGTGGCCAAAGTGGAGAAAGGGAAGTCTAAAA

AACTCAAAAGCGTCAAGGAACTGCTGGGCATCACAATCATGGAGCGATCAAGCTT

CGAAAAAAACCCCATCGACTTTCTCGAGGCGAAAGGATATAAAGAGGTCAAAAA

AGACCTCATCATTAAGCTTCCCAAGTACTCTCTCTTTGAGCTTGAAAACGGCCGGA

AACGAATGCTCGCTAGTGCGGGCGAGCTGCAGAAAGGTAACGAGCTGGCACTGCC

CTCTAAATACGTTAATTTCTTGTATCTGGCCAGCCACTATGAAAAGCTCAAAGGGT

CTCCCGAAGATAATGAGCAGAAGCAGCTGTTCGTGGAACAACACAAACACTACCT

TGATGAGATCATCGAGCAAATAAGCGAATTCTCCAAAAGAGTGATCCTCGCCGAC

GCTAACCTCGATAAGGTGCTTTCTGCTTACAATAAGCACAGGGATAAGCCCATCA

GGGAGCAGGCAGAAAACATTATCCACTTGTTTACTCTGACCAACTTGGGCGCGCC

TGCAGCCTTCAAGTACTTCGACACCACCATAGACAGAAAGCGGTACACCTCTACA

AAGGAGGTCCTGGACGCCACACTGATTCATCAGTCAATTACGGGGCTCTATGAAA

CAAGAATCGACCTCTCTCAGCTCGGTGGAGACAGCAGGGCTGAC]{CCCAAGAAG

AAGAGGAAGGTG}AGTGGTGGAGGAAGTGGCGGGTCAGGGTCG<u>ATGGACGCG</u>

TABLE 1-continued

Sequences of dCas9-Krab and dCas9-KRAB-MeCP2

<u>AAATCACTTACGGCATGGTCGAGAACACTGGTTACGTTCAAGGACGTGTTTGTGG</u>

<u>ACTTTACACGTGAGGAGTGGAAATTGCTGGATACTGCGCAACAAATTGTGTATCG</u>

<u>AAATGTCATGCTTGAGAATTACAAGAACCTCGTCAGTCTCGGATACCAGTTGACG</u>

<u>AAACCGGATGTGATCCTTAGGCTCGAAAAGGGGGAAGAACCTTGGCTGGTA</u>TCG

GGAGGTGGTTCGGGTGGCTCTGGATCA (AGCCCAAAGAAGAAACGGAAGGTGG

AAGCCTCAGTGCAGGTGAAAAGGGTGCTGGAAAAATCCCCCGGCAAACTCCTCGT

GAAGATGCCCTTCCAGGCTTCCCCTGGCGAAAAGGTGAAGGGGGTGGCGCAACC

ACATCTGCCCAGGTCATGGTCATCAAGCGACCTGGAAGGAAAAGAAAGGCCGAG

GCTGACCCTCAGGCCATTCCAAAGAAACGGGGACGCAAGCCAGGGTCCGTGGTCG

CAGCTGCAGCAGCTGAGGCTAAGAAAAAGGCAGTGAAGGAAAGCTCCATCCGCA

GTGTGCAGGAGACTGTCCTGCCCATCAAGAAGAGGAAGACTAGGGAGACCGTGTC

CATCGAGGTCAAAGAAGTGGTCAAGCCCCTGCTCGTGTCCACCCTGGGCGAAAAA

TCTGGAAAGGGGCTCAAAACATGCAAGTCACCTGGACGGAAAAGCAAGGAGTCT

AGTCCAAAGGGGCGCTCAAGCTCCGCTTCTAGTCCCCCTAAAAAGGAACACCATC

ACCATCACCATCACGCCGAGTCTCCTAAGGCTCCTATGCCACTGCTCCCACCACCT

CCACCACCTGAGCCACAGTCAAGCGAAGACCCCATCAGCCCACCCGAGCCTCAGG

ATCTGTCCTCTAGTATTTGCAAAGAGGAAAAGATGCCCAGAGCAGGCAGCCTGGA

GAGTGATGGCTGTCCAAAAGAACCCGCCAAGACCCAGCCTATGGTGGCAGCCGCT

GCAACTACCACCACAACCACAACTACCACAGTGGCCGAAAAATACAAGCATCGCG

GCGAGGGCGAACGAAAGGACATTGTGTCAAGCTCCATGCCCAGACCTAACCGGG

AGGAACCAGTCGATAGTAGGACACCCGTGACTGAGAGAGTCTCA) TAG

TABLE 2

Log$_2$(FC), Log$_2$(CPM), P-value, and FDR for DE genes associated with dCas9, dCas9-KRAB and dCAS9-KRAB-MeCP2 repressors.

| | Log$_2$FC | Log$_2$CPM | P-Value | FDR |
|---|---|---|---|---|
| dCas9 | | | | |
| HSPA6 | 6.57 | 8.3400 | 2.00E−25 | 2.74E−21 |
| DNAJB1 | 2.24 | 8.2800 | 6.09E−23 | 4.16E−19 |
| HSPA7 | 7.28 | 2.1290 | 9.68E−16 | 4.41E−12 |
| HSPA1A | 4.69 | 2.7660 | 4.75E−13 | 1.62E−09 |
| CRYAB | 6.55 | 2.0320 | 4.09E−12 | 1.12E−08 |
| ANKRD1 | 2.54 | 2.3950 | 4.02E−11 | 9.16E−08 |
| ZFAND2A | 1.65 | 4.2370 | 3.74E−10 | 7.29E−07 |
| ATF3 | 1.11 | 6.0300 | 2.30E−07 | 3.93E−04 |
| DNAH17 | 1.74 | 3.5590 | 2.92E−07 | 4.44E−04 |
| SCG2 | 4.11 | 0.1960 | 1.35E−05 | 1.75E−02 |
| VGF | 2.33 | 1.9290 | 1.41E−05 | 1.75E−02 |
| FOS | 1.41 | 2.9560 | 1.65E−05 | 1.88E−02 |
| GDF15 | 2.43 | 1.7580 | 2.68E−05 | 2.82E−02 |
| dCas9-KRAB | | | | |
| HSPA6 | 7.19 | 8.3398 | 2.26E−26 | 2.65E−22 |
| DNAJB1 | 2.62 | 8.2801 | 3.88E−26 | 2.65E−22 |
| HSPA1A | 6.36 | 2.7657 | 8.82E−21 | 4.02E−17 |
| HMOX1 | 2.07 | 5.5632 | 1.31E−20 | 4.48E−17 |
| CRYAB | 8.14 | 2.0315 | 2.86E−18 | 7.82E−15 |
| HSPA7 | 7.82 | 2.1293 | 5.79E−18 | 1.32E−14 |
| VGF | 4.6 | 1.9288 | 4.29E−16 | 8.37E−13 |
| ZFAND2A | 2 | 4.2367 | 6.13E−14 | 1.05E−10 |
| PPP1R15A | 1.47 | 5.3442 | 2.88E−12 | 4.36E−09 |
| GDF15 | 4.08 | 1.7576 | 6.69E−12 | 9.13E−09 |
| DNAH17 | 2.34 | 3.5595 | 2.04E−11 | 2.53E−08 |
| CLU | 1.49 | 4.588 | 6.38E−11 | 7.26E−08 |
| SERPINH1 | 1.24 | 6.3749 | 1.08E−10 | 1.14E−07 |
| FOXJ1 | 6.5 | 0.4447 | 1.47E−10 | 1.43E−07 |
| ANXA1 | 2.55 | 1.9991 | 1.02E−09 | 9.33E−07 |
| FOS | 1.86 | 2.9564 | 3.62E−09 | 3.09E−06 |
| NCRNA00306 | 3.6 | 0.6114 | 1.87E−08 | 1.50E−05 |
| CSRNP1 | 1.32 | 4.5789 | 2.82E−08 | 2.14E−05 |
| ANKRD1 | 2 | 2.3946 | 1.28E−07 | 9.22E−05 |
| ACHE | 1.89 | 2.0935 | 2.28E−06 | 1.56E−03 |
| SCG2 | 4.28 | 0.1963 | 4.42E−06 | 2.75E−03 |
| ATF3 | 1.02 | 6.0304 | 4.42E−06 | 2.75E−03 |
| HLA-G | 3.54 | −0.0433 | 5.02E−06 | 2.98E−03 |
| INPP5D | 2.93 | 0.983 | 5.69E−06 | 3.24E−03 |
| RELB | 1.56 | 2.6216 | 6.66E−06 | 3.64E−03 |
| PNLDC1 | 3.2 | 0.0906 | 8.19E−06 | 4.15E−03 |
| CYP4F3 | 7.12 | −0.4274 | 8.21E−06 | 4.15E−03 |
| MMP12 | 4.58 | −0.6846 | 9.52E−06 | 4.64E−03 |
| TUBB3 | 1.15 | 3.9455 | 1.39E−05 | 6.53E−03 |
| PLK2 | 1.23 | 3.6057 | 1.52E−05 | 6.92E−03 |
| IRX4 | 2.55 | 0.425 | 2.43E−05 | 1.07E−02 |
| DUSP8 | 1.22 | 3.6476 | 3.69E−05 | 1.57E−02 |
| FERMT3 | 2.22 | 0.6882 | 5.66E−05 | 2.34E−02 |
| ACRC | 1.63 | 1.6191 | 7.17E−05 | 2.88E−02 |
| IL11 | 1.92 | 0.9971 | 9.89E−05 | 3.86E−02 |

TABLE 2-continued

Log₂(FC), Log₂(CPM), P-value, and FDR for DE genes associated with dCas9, dCas9-KRAB and dCAS9-KRAB-MeCP2 repressors.

| | Log₂FC | Log₂CPM | P-Value | FDR |
|---|---|---|---|---|
| dCas9-KRAB-MeCP2 | | | | |
| HSPA6 | 6.7 | 8.34 | 1.27E−25 | 1.73E−21 |
| DNAJB1 | 2.24 | 8.28 | 6.26E−23 | 4.28E−19 |
| HSPA1A | 5.8 | 2.766 | 4.26E−18 | 1.94E−14 |
| HSPA7 | 6.99 | 2.129 | 2.26E−14 | 7.71E−11 |
| CRYAB | 6.59 | 2.032 | 4.73E−12 | 1.29E−08 |
| DNAH17 | 2.43 | 3.559 | 8.96E−12 | 2.04E−08 |
| INPP5D | 3.96 | 0.983 | 1.65E−09 | 3.23E−06 |
| GDF15 | 3.29 | 1.758 | 2.00E−08 | 3.41E−05 |
| CYP4F3 | 7.81 | −0.427 | 3.40E−07 | 5.16E−04 |
| FOXJ1 | 5.41 | 0.445 | 4.53E−07 | 6.19E−04 |
| ZFAND2A | 1.33 | 4.237 | 1.24E−06 | 1.54E−03 |
| PPP1R15A | 1.09 | 5.344 | 1.46E−06 | 1.66E−03 |
| VGF | 2.55 | 1.929 | 2.43E−06 | 2.56E−03 |
| NCRNA00306 | 2.75 | 0.611 | 2.56E−05 | 2.50E−02 |
| DUSP8 | 1.23 | 3.648 | 3.32E−05 | 2.92E−02 |
| PLA2G4C | 1.89 | 1.495 | 3.55E−05 | 2.92E−02 |
| ANXA1 | 1.76 | 1.999 | 3.64E−05 | 2.92E−02 |

TABLE 3

Mean fold changes of all essential gene-targeting sgRNAs and p-values for statistical comparison between essential and non-essential guides in HAP1 lethality screen.

| Experiment | Mean essential guides log₂ OR | P-value[#] |
|---|---|---|
| dCas9_day0 | −0.008 | 0.1329 |
| dCas9_day7 | 0.001 | 0.669 |
| dCas9_day14 | −0.001 | 0.6289 |
| dCas9-KRAB_day0 | −0.015 | 0.005708 |
| dCas9-KRAB_day7 | −0.056 | 1.83E−07 |
| dCas9-KRAB_day14 | −0.081 | 5.41E−19 |
| dCas9-KRAB-MeCP2_day0 | 0.031 | 0.9996 |
| dCas9-KRAB-MeCP2_day7* | −2.358 | 4.87E−78 |
| dCas9-KRAB-MeCP2_day14** | −2.586 | 3.52E−80 |

[#]p-value is derived from Welch 2 sample t-test comparing essential guides versus non-essential guides (1-tailed test)
*Log₂ Odds-ratio (log₂ OR) that was -Infinity, i.e. complete depletion, were replaced by the least finite OR for day 7, i.e. −7.607176
**log₂ Odds-ratio (log₂ OR) that were -Infinity, i.e. complete depletion, were replaced by the least finite OR for day 14, i.e. −8.867043

TABLE 4

Mean fold changes of all essential gene-targeting sgRNAs and p-values for statistical comparison between essential and non-essential guides in SH-SY5Y lethality screen.

| Experiment | mean essential guides log2 OR | P-value[#] |
|---|---|---|
| dCas9_day0 | −0.0517 | 0.0009321 |
| dCas9_day7 | −0.10179 | 9.92E−16 |
| dCas9_day14 | −0.12011 | 3.76E−20 |
| dCas9_day22 | −0.149066 | 1.31E−23 |
| dCas9-KRAB_day0 | −0.1341297 | 3.79E−22 |
| dCas9-KRAB_day7 | −0.3476919 | 4.72E−37 |
| dCas9-KRAB_day14 | −0.3733395 | 2.16E−44 |
| dCas9-KRAB_day22 | −0.386887 | 2.24E−52 |
| dCas9-KRAB-MeCP2_day0 | −0.1937839 | 5.27E−26 |
| dCas9-KRAB-MeCP2_day7 | −0.4740388 | 2.55E−55 |
| dCas9-KRAB-MeCP2_day14 | −0.3774654 | 1.19E−63 |
| dCas9-KRAB-MeCP2_day22 | −0.525382 | 3.08E−70 |

[#]p-value is derived from Welch 2 sample t-test comparing essential guides versus non-essential guides (1-tailed test).

TABLE 5

Sequence of sgRNAs used in the studies

| Target gene | sgRNA sequence |
|---|---|
| EYFP reporter[1] | TACCTCATCAGGAACATGT |
| NEAT1 sgRNA1 | GCGACAGGGAGGGATGCGCGCC |
| NEAT1 sgRNA2 | GCGCGCCTGGGTGTAGTTGT |
| NEAT1 sgRNA3 | GAAGTGGCTAGCTCAGGGCTTC |
| CXCR4 | CAGGTAGCAAAGTGACGCCGA |
| SEL1L sgRNA1 | GCAGGAAGAGCAGCGGCGAGG |
| SEL1L sgRNA2 | GGGGGCGGATACTGACCCG |
| SEL1L sgRNA3[2] | GATACTGACCCGAGGACGCCG |
| ARPC2 sgRNA1[2] | TGTCGGTGAAGCGGCAGTGG |
| ARPC2 sgRNA2 | CAGGCGGGTTCAGGCTTCGG |
| ERK1 sgRNA1[2] | GGGAGCCCCGTAGAACCGAG |
| ERK1 sgRNA2 | CACCGCCCTCCTCCCCACGG |
| BRCA1 sgRNA1 | GGATTTCCGAAGCTGACAGA |
| BRCA1 sgRNA2[2] | GCTCGCTGAGACTTCCTGGA |
| BLM sgRNA1 | AGGAAACGGAAGAACCCGAG |
| BLM sgRNA2 | CCTCGCACGCAGACTCCTAG |
| MET1 sgRNA1 | TGAGCAGATGCGGAGCCGAG |
| MET1 sgRNA2 | ACTGGTTCCTGGGCACCGAA |
| RHOA sgRNA1 | AGTTCCCGTGATGCCCCACG |
| RHOA sgRNA2 | GCGCGCCTCCGAGTGCCCAG |
| CHK2 sgRNA1 | GGAGAGTGTGCGGCTCCAGG |
| CHK2 sgRNA2 | CGCAGCCTCAGCCAGCAGAG |
| CHK1 sgRNA1 | GGTGGAGGAATGGTACCAGG |
| CHK1 sgRNA2[2] | GGGTCTAGATTAGTGAGGGA |
| CANX_-700* | TGAAGTGAGATTAGGTGTCA |
| CANX_-335* | GTTGGGTTGGAACGCCCCGA |
| CANX_-505* | GGTTCTGCTCACGCCCGTAG |
| CANX_-22* | GCTCGCTCGCGCGGCAGCGG |
| CANX_-1[2]* | GGCCGAGGCCTCTTGGTTCTG |
| CANX_47* | GCGCCGCAGTAAAGAGAGAGG |
| CANX_155* | TCGGGCCTGTGAGGACCTCG |
| CANX_263* | CGACGCGCCCGCCGTGAGCG |
| CANX_472* | GAGTAACTGGGTAAAAGTAT |
| CANX_642* | ACCAGAAGGAGAACACGCAG |
| SYVN1_-1032* | GGAAAACGCAAGGCACAAAG |
| SYVN1_-734* | AACGTTCCCGGAGGCCAGCC |
| SYVN1_-601* | ACCTTTGCTGGCCTATAGAA |
| SYVN1_-555* | AACTTATCGCAACCAATCAG |

TABLE 5-continued

Sequence of sgRNAs used in the studies

| Target gene | sgRNA sequence |
| --- | --- |
| SYVN1_-339* | CAGGTGGTACAGCCCGCAAG |
| SYVN1_-194* | ATTACCTTCCGACCACCTCT |
| SYVN1_-116* | CCTACGTGGGCCCATAGCAA |
| SYVN1_43* | ACACCTCACTTCCGGCGGCG |
| SYVN1_19* | CCGCTCAATCCGCGCGACTG |
| SYVN1_45* | GGCGCTGGGTTCCTGGTGAGT |
| SYVN1_183* | GCACCGGCGTCTGAGGTCTC |
| SYVN1_228[2]* | GTTGCGGGCGTCGCAGGCA |
| SYVN1_292* | GAGAGCAGCAGCGGGACGGG |
| SYVN1_480* | TGAGAGCAGCCAAGGCACAG |
| SYVN1_702* | TAAGTGATCACACTGACGCA |
| SYVN1_844* | TCGTGCTGTGCAAAATAGCC |

[1]Guide RNA targeting EYFP reporter in the reporter screen assay
[2]Guide RNA used in single gene targeting experiments
*The numerical number indicates the position of spacer relative to transcription start site of the target gene.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method of modulating expression of a target nucleic acid in a eukaryotic cell comprising providing to the cell a guide RNA complementary to the target nucleic acid sequence, providing to the cell a fusion protein, wherein the fusion protein comprises a nuclease null Cas9 protein (dCas9) and an effector domain, wherein the effector domain comprises a fusion of two or more transcriptional repressor domains selected from the group consisting of Kruppel-associated box (KRAB), MeCP2, SIN3A, HDT1, MBD2B, NIPP1, and HP1A, and wherein the nuclease null Cas9 protein interacts with the guide RNA and binds to the target nucleic acid sequence in a site specific manner and wherein the effector domain modulates expression of the target nucleic acid.

2. The method of claim 1
   wherein the guide RNA is provided to the cell by introducing to the cell a nucleic acid encoding the guide RNA, wherein the fusion protein is provided to the cell by introducing to the cell a nucleic acid encoding the fusion protein, and wherein the cell expresses the guide RNA and the fusion protein.

3. The method of claim 1 wherein the eukaryotic cell is a yeast cell, a plant cell or a mammalian cell.

4. The method or claim 3 wherein the eukaryotic cell is a human cell.

5. The method of claim 1 wherein the effector domain comprises a fusion of two transcriptional repressor domains selected from the group consisting of Kruppel-associated box (KRAB), MeCP2, SIN3A, HDT1, MBD2B, NIPP1, and HP1A.

6. The method of claim 1 wherein the effector domain comprises a fusion of three or more transcriptional repressor domains selected from the group consisting of Krüppel-associated box (KRAB), MeCP2, SIN3A, HDT1, MBD2B, NIPP1, and HP1A.

7. The method of claim 1 wherein the effector domain comprises a bipartite fusion of KRAB-MeCP2.

8. The method of claim 1 wherein the fusion protein comprises a fusion of dCas9-KRAB-MeCP2.

9. The method of claim 8 wherein the dCas9-KRAB-MeCP2 fusion exhibited at least two fold stronger repression of target gene expression compared to nuclease null Cas9 or nuclease null Cas9 fused to KRAB.

* * * * *

SEQUENCE LISTING

<160> NUMBER OF SEQ ID NOS: 56

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
tacctcatca ggaacatgtt gg                                              22

<210> SEQ ID NO 2
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
agatcggaag agcacacgtc tgaactccag tcac                                 34

<210> SEQ ID NO 3
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ttactatgcc gctggtggct ctagatgtga gaaagggatg tgctgcgaga aggctaga     58

<210> SEQ ID NO 4
<211> LENGTH: 188
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base

```
<222> LOCATION: (1)..(6)
<223> OTHER INFORMATION: a, c, t, g, unknown or other
<220> FEATURE:
<221> NAME/KEY: modified_base
<222> LOCATION: (29)..(48)
<223> OTHER INFORMATION: a, c, t, g, unknown or other

<400> SEQUENCE: 4
nnnnnnccct tggagaaaag ccttgttttnn nnnnnnnnnn nnnnnnnngt ttaagagcta      60
gaaatagcaa gtttaaataa ggctagtccg ttatcaactt gaaaaagtgg caccgagtcg     120 gtgcttttt ctagacccag ctttcttgta caaaaaaag aattcctgca gccccgataa     180
aataaaag                                                             188

<210> SEQ ID NO 5
<211> LENGTH: 4395
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
atggacaaga agtactccat tgggctcgct atcggcacaa acagcgtcgg ctgggccgtc      60
attacggacg agtacaaggt gccgagcaaa aaattcaaag ttctgggcaa taccgatcgc     120
cacagcataa agaagaacct cattggcgcc ctcctgttcg actccgggga cggccgaa      180 gccacgcggc tcaaaagaac agcacggcgc agatataccc gcagaaagaa tcggatctgc     240
tacctgcagg agatctttag taatgagatg gctaaggtgg atgactcttt cttccatagg     300
ctggaggagt cctttttggt ggaggaggat aaaaagcacg agcgccaccc aatctttggc     360
aatatcgtgg acgaggtggc gtaccatgaa agtacccaa ccatatatca tctgaggaag     420
aagcttgtag acagtactga taaggctgac ttgcggttga tctatctcgc gctggcgcat     480
atgatcaaat tcggggaca cttcctcatc gaggggacc tgaacccaga caacagcgat     540
gtcgataaac tctttatcca actggttcag acttacaatc agcttttcga agagaacccg     600
atcaacgcat ccggagttga cgccaaagca atcctgagcg ctaggctgtc caaatcccgg     660
cggctcgaaa acctcatcgc acagctccct ggggagaaga gaacggcct gtttggtaat     720 cttatcgccc tgtcactcgg gctgaccccc aactttaaat ctaacttcga cctggccgaa     780
gatgccaagc ttcaactgag caaagacacc tacgatgatg atctcgacaa tctgctggcc     840
cagatcggcg accagtacgc agaccttttt ttggcggcaa agaacctgtc agacgccatt     900
ctgctgagtg atattctgcg agtgaacacg gagatcacca agctccgct gagcgctagt     960 atgatcaagc gctatgatga gcaccaccaa gacttgactt tgctgaaggc ccttgtcaga    1020
cagcaactgc ctgagaagta caaggaaatt ttcttcgatc agtctaaaaa tggctacgcc    1080
ggatacattg acggcggagc aagccaggag gaatttttaca aatttattaa gcccatcttg    1140 gaaaaatgg acggcaccga ggagctgctg gtaaagctta acagagaaga tctgttgcgc    1200
aaacagcgca ctttcgacaa tggaagcatc ccccaccaga ttcacctggg cgaactgcac    1260
gctatcctca gcggcaaga ggatttctac ccctttttga agataacag ggaaaagatt    1320 gagaaaatcc tcacatttcg gatacccctac tatgtaggcc ccctcgcccg ggaaaattcc    1380
agattcgcgt ggatgactcg caaatcagaa gagaccatca ctcctggaa cttcgaggaa    1440 gtcgtggata aggggggcctc tgcccagtcc ttcatcgaaa ggatgactaa ctttgataaa    1500
aatctgccta acgaaaaggt gcttcctaaa cactctctgc tgtacgagta cttcacagtt    1560
```

```
tataacgagc tcaccaaggt caaatacgtc acagaaggga tgagaaagcc agcattcctg    1620
tctggagagc agaagaaagc tatcgtggac ctcctcttca agacgaaccg gaaagttacc    1680
gtgaaacagc tcaaagaaga ctatttcaaa aagattgaat gtttcgactc tgttgaaatc    1740
agcggagtgg aggatcgctt caacgcatcc ctgggaacgt atcacgatct cctgaaaatc    1800
attaaagaca aggacttcct ggacaatgag gagaacgagg acattcttga ggacattgtc    1860
ctcaccctta cgttgtttga agatagggag atgattgaag aacgcttgaa aacttacgct    1920
catctcttcg acgacaaagt catgaaacag ctcaagaggc gccgatatac aggatggggg    1980
cggctgtcaa gaaaactgat caatgggatc cgagacaagc agagtggaaa gacaatcctg    2040
gattttctta agtccgatgg atttgccaac cggaacttca tgcagttgat ccatgatgac    2100
tctctcacct ttaaggagga catccagaaa gcacaagttt ctggccaggg ggacagtctt    2160
cacgagcaca tcgctaatct tgcaggtagc ccagctatca aaaagggaat actgcagacc    2220
gttaaggtcg tggatgaact cgtcaaagta atgggaaggc ataagcccga gaatatcgtt    2280
atcgagatgg cccgagagaa ccaaactacc cagaagggac agaagaacag tagggaaagg    2340
atgaagagga ttgaagaggg tataaaagaa ctggggtccc aaatccttaa ggaacaccca    2400
gttgaaaaca cccagcttca gaatgagaag ctctacctgt actacctgca gaacggcagg    2460
gacatgtacg tggatcagga actggacatc aatcggctct ccgactacga cgtggctgct    2520
atcgtgcccc agtctttcct caaagatgat tctattgata ataaagtgtt gacaagatcc    2580
gataaagcta gagggaagag tgataacgtc ccctcagaag aagttgtcaa gaaaatgaaa    2640
aattattggc ggcagctgct gaacgccaaa ctgatcacac aacggaagtt cgataatctg    2700
actaaggctg aacagaggtgg cctgtctgag ttggataaag ccggcttcat caaaaggcag    2760
cttgttgaga cacgccagat caccaagcac gtggcccaaa ttctcgattc acgcatgaac    2820
accaagtacg atgaaaatga caaactgatt cgagaggtga agttattac tctgaagtct    2880 aagctggtct cagatttcag aaaggacttt cagttttata aggtgagaga gatcaacaat    2940
taccaccatg cgcatgatgc ctacctgaat gcagtggtag gcactgcact tatcaaaaaa    3000
tatcccaagc ttgaatctga atttgtttac ggagactata agtgtacga tgttaggaaa    3060 atgatcgcaa agtctgagca ggaaatggc aaggccaccg ctaagtactt cttttacagc    3120
aatattatga attttttcaa gaccgagatt acactggcca atggagagat tcggaagcga    3180
ccacttatcg aaacaaacgg agaaacagga gaaatcgtgt gggacaaggg tagggatttc    3240
gcgacagtcc ggaaggtcct gtccatgccg caggtgaaca tcgttaaaaa gaccgaagta    3300
cagaccggag gcttctccaa ggaaagtatc ctcccgaaaa ggaacagcga caagctgatc    3360
gcacgcaaaa aagattggga ccccaagaaa tacgccggat tcgattctcc tacagtcgct    3420
tacagtgtac tggttgtggc caaagtggag aaagggaagt ctaaaaaact caaaagcgtc    3480
aaggaactgc tgggcatcac aatcatggag cgatcaagct tcgaaaaaaa ccccatcgac    3540
tttctcgagg cgaaaggata taagaggtc aaaaaagacc tcatcattaa gcttcccaag    3600
tactctctct ttgagcttga aaacggccgg aaacgaatgc tcgctagtgc gggcgagctg    3660
cagaaaggta acgagctggc actgcccctct aaatacgtta atttcttgta tctgccagc    3720 cactatgaaa agctcaaagg gtctcccgaa gataatgagc agaagcagct gttcgtggaa    3780
caacacaaac actaccttga tgagatcatc gagcaaataa gcgaattctc caaaagagtg    3840
atcctcgccg acgctaaccct cgataaggtg ctttctgctt acaataagca cagggataag    3900
```

| | |
|---|---:|
| cccatcaggg agcaggcaga aaacattatc cacttgttta ctctgaccaa cttgggcgcg | 3960 |
| cctgcagcct tcaagtactt cgacaccacc atagacagaa agcggtacac ctctacaaag | 4020 |
| gaggtcctgg acgccacact gattcatcag tcaattacgg ggctctatga acaagaatc | 4080 |
| gacctctctc agctcggtgg agacagcagg gctgacccca agaagaagag gaaggtgagt | 4140 |
| ggtggaggaa gtggcgggtc agggtcgatg gacgcgaaat cacttacggc atggtcgaga | 4200 |
| acactggtta cgttcaagga cgtgtttgtg gactttacac gtgaggagtg gaaattgctg | 4260 |
| gatactgcgc aacaaattgt gtatcgaaat gtcatgcttg agaattacaa gaacctcgtc | 4320 |
| agtctcggat accagttgac gaaaccggat gtgatcctta ggctcgaaaa gggggaagaa | 4380 |
| ccttggctgg tatag | 4395 |

<210> SEQ ID NO 6
<211> LENGTH: 5316
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 6

| | |
|---|---:|
| atggacaaga agtactccat tgggctcgct atcggcacaa acagcgtcgg ctgggccgtc | 60 |
| attacggacg agtacaaggt gccgagcaaa aaattcaaag ttctgggcaa taccgatcgc | 120 |
| cacagcataa agaagaacct cattggcgcc ctcctgttcg actccgggga cggccgaa | 180 |
| gccacgcggc tcaaaagaac agcacggcgc agatataccc gcagaaagaa tcggatctgc | 240 |
| tacctgcagg agatctttag taatgagatg gctaaggtgg atgactcttt cttccatagg | 300 |
| ctggaggagt ccttttttggt ggaggaggat aaaaagcacg agcgccaccc aatctttggc | 360 |
| aatatcgtgg acgaggtggc gtaccatgaa aagtacccaa ccatatatca tctgaggaag | 420 |
| aagcttgtag acagtactga taaggctgac ttgcggttga tctatctcgc gctggcgcat | 480 |
| atgatcaaat tcggggaca cttcctcatc gagggggacc tgaacccaga caacagcgat | 540 |
| gtcgataaac tctttatcca actggttcag acttacaatc agcttttcga agagaacccg | 600 |
| atcaacgcat ccggagttga cgccaaagca atcctgagcg ctaggctgtc caaatcccgg | 660 |
| cggctcgaaa acctcatcgc acagctccct ggggagaaga gaacggcct gtttggtaat | 720 |
| cttatcgccc tgtcactcgg gctgacccc aactttaaat ctaacttcga cctggccgaa | 780 |
| gatgccaagc ttcaactgag caaagacacc tacgatgatg atctcgacaa tctgctggcc | 840 |
| cagatcggcg accagtacgc agacctttt ttggcggcaa agaacctgtc agacgccatt | 900 |
| ctgctgagtg atattctgcg agtgaacacg gagatcacca agctccgct gagcgctagt | 960 |
| atgatcaagc gctatgatga gcaccaccaa gacttgactt tgctgaaggc ccttgtcaga | 1020 |
| cagcaactgc ctgagaagta caaggaaatt ttcttcgatc agtctaaaaa tggctacgcc | 1080 |
| ggatacattg acggcggagc aagccaggag gaatttttaca aatttattaa gcccatcttg | 1140 |
| gaaaaaatgg acggcaccga ggagctgctg gtaaagctta acagagaaga tctgttgcgc | 1200 |
| aaacagcgca ctttcgacaa tggaagcatc ccccaccaga ttcacctggg cgaactgcac | 1260 |
| gctatcctca ggcggcaaga ggatttctac ccctttttga aagataacag ggaaaagatt | 1320 |
| gagaaaatcc tcacatttcg gataccctac tatgtaggcc ccctcgcccg ggaaaattcc | 1380 |
| agattcgcgt ggatgactcg caaatcagaa gagaccatca ctcccctgga acttcgaggaa | 1440 |
| gtcgtggata agggggcctc tgcccagtcc ttcatcgaaa ggatgactaa ctttgataaa | 1500 |

```
aatctgccta acgaaaaggt gcttcctaaa cactctctgc tgtacgagta cttcacagtt    1560
tataacgagc tcaccaaggt caaatacgtc acagaaggga tgagaaagcc agcattcctg    1620
tctggagagc agaagaaagc tatcgtggac ctcctcttca agacgaaccg gaaagttacc    1680
gtgaaacagc tcaaagaaga ctatttcaaa aagattgaat gtttcgactc tgttgaaatc    1740
agcggagtgg aggatcgctt caacgcatcc ctgggaacgt atcacgatct cctgaaaatc    1800
attaaagaca aggacttcct ggacaatgag gagaacgagg acattcttga ggacattgtc    1860
ctcacccttn cgttgtttga agatagggag atgattgaag aacgcttgaa aacttacgct    1920
catctcttcg acgacaaagt catgaaacag ctcaagaggc gccgatatac aggatggggg    1980
cggctgtcaa gaaaactgat caatgggatc cgagacaagc agagtggaaa gacaatcctg    2040
gatttcttta agtccgatgg atttgccaac cggaacttca tgcagttgat ccatgatgac    2100
tctctcacct ttaaggagga catccagaaa gcacaagttt ctggccaggg ggacagtctt    2160
cacgagcaca tcgctaatct tgcaggtagc ccagctatca aaagggaat actgcagacc    2220 gttaaggtcg tggatgaact cgtcaaagta atgggaaggc ataagcccga gaatatcgtt    2280
atcgagatgg cccgagagaa ccaaactacc cagaagggac agaagaacag tagggaaagg    2340
atgaagagga ttgaagaggg tataaaagaa ctggggtccc aaatccttaa ggaacaccca    2400
gttgaaaaca cccagcttca gaatgagaag ctctacctgt actacctgca gaacggcagg    2460
gacatgtacg tggatcagga actggacatc aatcggctct ccgactacga cgtggctgct    2520
atcgtgcccc agtcttttct caaagatgat tctattgata taaagtgtt gacaagatcc    2580 gataaagcta gagggaagag tgataacgtc ccctcagaag aagttgtcaa gaaaatgaaa    2640
aattattggc ggcagctgct gaacgccaaa ctgatcacac aacggaagtt cgataatctg    2700
actaaggctg aacgaggtgg cctgtctgag ttggataaag ccggcttcat caaaaggcag    2760
cttgttgaga cacgccagat caccaagcac gtggcccaaa ttctcgattc acgcatgaac    2820
accaagtacg atgaaaatga caaactgatt cgagaggtga agttattac tctgaagtct    2880 aagctggtct cagatttcag aaaggacttt cagttttata aggtgagaga gatcaacaat    2940
taccaccatg cgcatgatgc ctacctgaat gcagtggtag gcactgcact tatcaaaaaa    3000
tatcccaagc ttgaatctga atttgtttac ggagactata agtgtacga tgttaggaaa    3060 atgatcgcaa agtctgagca ggaaataggc aaggccaccg ctaagtactt cttttacagc    3120
aatattatga attttttcaa gaccgagatt acactggcca atggagagat tcggaagcga    3180
ccacttatcg aaacaaacgg agaaacagga gaaatcgtgt gggacaaggg tagggatttc    3240
gcgacagtcc ggaaggtcct gtccatgccg caggtgaaca tcgttaaaaa gaccgaagta    3300
cagaccggag gcttctccaa ggaaagtatc ctcccgaaaa ggaacagcga caagctgatc    3360
gcacgcaaaa aagattggga ccccaagaaa tacggcggat tcgattctcc tacagtcgct    3420
tacagtgtac tggttgtggc caagtggag aaagggaagt ctaaaaaact caaaagcgtc    3480
aaggaactgc tgggcatcac aatcatggag cgatcaagct tcgaaaaaaa ccccatcgac    3540
tttctcgagg cgaaaggata taagaggtc aaaaaagacc tcatcattaa gcttcccaag    3600
tactctctct ttgagcttga aaacggccgg aaacgaatgc tcgctagtgc gggcgagctg    3660
cagaaaggta acgagctggc actgccctct aaatacgtta atttcttgta tctggccagc    3720
cactatgaaa agctcaaagg gtctcccgaa gataatgagc agaagcagct gttcgtggaa    3780
caacacaaac actaccttga tgagatcatc gagcaaataa gcgaattctc caaaagagtg    3840
atcctcgccg acgctaacct cgataaggtg ctttctgctt acaataagca cagggataag    3900
```

```
cccatcaggg agcaggcaga aaacattatc cacttgttta ctctgaccaa cttgggcgcg    3960
cctgcagcct tcaagtactt cgacaccacc atagacagaa agcggtacac ctctacaaag    4020
gaggtcctgg acgccacact gattcatcag tcaattacgg ggctctatga aacaagaatc    4080
gacctctctc agctcggtgg agacagcagg gctgacccca agaagaagag gaaggtgagt    4140
ggtggaggaa gtggcgggtc agggtcgatg gacgcgaaat cacttacggc atggtcgaga    4200
acactggtta cgttcaagga cgtgtttgtg gactttacac gtgaggagtg gaaattgctg    4260
gatactgcgc aacaaattgt gtatcgaaat gtcatgcttg agaattacaa gaacctcgtc    4320
agtctcggat accagttgac gaaaccggat gtgatcctta ggctcgaaaa gggggaagaa    4380
ccttggctgg tatcgggagg tggttcgggt ggctctggat caagcccaaa gaagaaacgg    4440
aaggtggaag cctcagtgca ggtgaaaagg gtgctgaaaa atccccggg caaactcctc    4500 gtgaagatgc ccttccaggc ttcccctggc ggaaaaggtg aaggggtgg cgcaaccaca    4560 tctgcccagg tcatggtcat caagcgacct ggaaggaaaa gaaaggccga ggctgaccct    4620
caggccattc aaagaaacg gggacgcaag ccagggtccg tggtcgcagc tgcagcagct    4680
gaggctaaga aaaaggcagt gaaggaaagc tccatccgca gtgtgcagga gactgtcctg    4740
cccatcaaga agaggaagac tagggagacc gtgtccatcg aggtcaaaga agtggtcaag    4800
cccctgctcg tgtccaccct gggcgaaaaa tctggaaagg ggctcaaaac atgcaagtca    4860
cctggacgga aaagcaagga gtctagtcca aaggggcgct caagctccgc ttctagtccc    4920
cctaaaaagg aacaccatca ccatcaccat cacgccgagt ctcctaaggc tcctatgcca    4980
ctgctcccac cacctccacc acctgagcca cagtcaagcg aagaccccat cagcccaccc    5040
gagcctcagg atctgtcctc tagtatttgc aaagaggaaa agatgcccag agcaggcagc    5100
ctggagagtg atggctgtcc aaaagaaccc gccaagaccc agcctatggt ggcagccgct    5160
gcaactacca ccacaaccac aactaccaca gtggccgaaa aatacaagca tcgcggcgag    5220
ggcgaacgaa aggacattgt gtcaagctcc atgcccagac taaccgggga ggaaccagtc    5280
gatagtagga cacccgtgac tgagagagtc tcatag                             5316
```

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
tacctcatca ggaacatgt                                                    19

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gcgacaggga gggatgcgcg cc                                                22

<210> SEQ ID NO 9
<211> LENGTH: 20
<212> TYPE: DNA

<213> ORGANISM: Artificial Sequence
<220> FEATURE:
<223> OTHER INFORMATION: Description of Artificial Sequence: Synthetic
      oligonucleotide

<400> SEQUENCE: 9
gcgcgcctgg gtgtagttgt                                              20

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gaagtggcta gctcagggct tc                                           22

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
caggtagcaa agtgacgccg a                                            21

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gcaggaagag cagcggcgag g                                            21

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gggggcggat actgacccg                                               19

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gatactgacc cgaggacgcc g                                            21

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
tgtcggtgaa gcggcagtgg                                                   20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
caggcgggtt caggcttcgg                                                   20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gggagccccg tagaaccgag                                                   20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
caccgccctc ctccccacgg                                                   20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
ggatttccga agctgacaga                                                   20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gctcgctgag acttcctgga                                                   20

<210> SEQ ID NO 21
<211> LENGTH: 20
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 21
aggaaacgga agaacccgag                                                    20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
cctcgcacgc agactcctag                                                    20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
tgagcagatg cggagccgag                                                    20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
actggttcct gggcaccgaa                                                    20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
agttcccgtg atgccccacg                                                    20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
gcgcgcctcc gagtgcccag                                                    20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 27
ggagagtgtg cggctccagg                                          20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
cgcagcctca gccagcagag                                          20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
ggtggaggaa tggtaccagg                                          20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
gggtctagat tagtgaggga                                          20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
tgaagtgaga ttaggtgtca                                          20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
gttgggttgg aacgccccga                                          20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
ggttctgctc acgcccgtag				20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
gctcgctcgc gcggcagcgg				20

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
ggccgaggcc tcttggttct g				21

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
gcgccgcagt aaagagagag g				21

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
tcgggcctgt gaggacctcg				20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
cgacgcgccc gccgtgagcg				20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
gagtaactgg gtaaaagtat                                                     20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
accagaagga gaacacgcag                                                     20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
ggaaaacgca aggcacaaag                                                     20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
aacgttcccg gaggccagcc                                                     20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
acctttgctg gcctatagaa                                                     20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
aacttatcgc aaccaatcag                                                     20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45

```
caggtggtac agcccgcaag                                                     20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
attaccttcc gaccacctct                                                     20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
cctacgtggg cccatagcaa                                                     20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
acacctcact tccggcggcg                                                     20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
ccgctcaatc cgcgcgactg                                                     20

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
ggcgctgggt tcctggtgag t                                                   21

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
```

```
gcaccggcgt ctgaggtctc                                                    20

<210> SEQ ID NO 52
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
gttgcgggcg tcgcaggca                                                     19

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
gagagcagca gcgggacggg                                                    20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
tgagagcagc caaggcacag                                                    20

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
taagtgatca cactgacgca                                                    20

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
tcgtgctgtg caaaatagcc                                                    20
```